US012325788B2

(12) United States Patent
Chang et al.

(10) Patent No.: US 12,325,788 B2
(45) Date of Patent: *Jun. 10, 2025

(54) PLASTICIZED PVC ADMIXTURES WITH SURFACE MODIFYING MACROMOLECULES AND ARTICLES MADE THEREFROM

(71) Applicant: EVONIK CANADA INC., Burlington (CA)

(72) Inventors: Weilun Chang, Toronto (CA); Jeannette Ho, Toronto (CA); J. Paul Santerre, Toronto (CA); Sanjoy Mullick, Brampton (CA)

(73) Assignee: Evonik Canada Inc., Burlington (CA)

( * ) Notice: Subject to any disclaimer, the term of this patent is extended or adjusted under 35 U.S.C. 154(b) by 279 days.

This patent is subject to a terminal disclaimer.

(21) Appl. No.: 16/724,792

(22) Filed: Dec. 23, 2019

(65) Prior Publication Data

US 2020/0123367 A1 Apr. 23, 2020

Related U.S. Application Data

(63) Continuation of application No. 16/386,409, filed on Apr. 17, 2019, now Pat. No. 10,557,030, which is a continuation of application No. PCT/US2017/057226, filed on Oct. 18, 2017.

(60) Provisional application No. 62/409,759, filed on Oct. 18, 2016.

(51) Int. Cl.
| | | |
|---|---|---|
| C08L 27/06 | (2006.01) | |
| A61L 27/48 | (2006.01) | |
| A61L 27/50 | (2006.01) | |
| C08J 3/18 | (2006.01) | |
| C08K 5/00 | (2006.01) | |

(52) U.S. Cl.
CPC .............. *C08L 27/06* (2013.01); *A61L 27/48* (2013.01); *A61L 27/502* (2013.01); *C08J 3/18* (2013.01); *A61L 2420/02* (2013.01); *C08J 2327/06* (2013.01); *C08J 2475/08* (2013.01); *C08K 5/0016* (2013.01); *C08L 2201/10* (2013.01); *C08L 2205/06* (2013.01)

(58) Field of Classification Search
CPC ..................................................... A61L 27/48
See application file for complete search history.

(56) References Cited

U.S. PATENT DOCUMENTS

| | | |
|---|---|---|
| 3,392,183 A | 7/1968 | Windemuth et al. |
| 3,427,366 A | 2/1969 | Verdol et al. |
| 3,759,788 A | 9/1973 | Gajewski et al. |
| 3,872,058 A | 3/1975 | Gresham |
| 3,933,557 A | 1/1976 | Pall |
| 4,312,907 A | 1/1982 | Hiraoka et al. |
| 4,424,311 A | 1/1984 | Nagaoka et al. |
| 4,465,480 A | 8/1984 | Tanaka et al. |
| 4,552,707 A | 11/1985 | How |
| 4,584,362 A | 4/1986 | Eckart et al. |
| 4,661,530 A | 4/1987 | Gogolewski et al. |
| 4,742,090 A | 5/1988 | Hunter et al. |
| 4,743,629 A | 5/1988 | Karakelle et al. |
| 4,788,083 A | 11/1988 | Dammann et al. |
| 4,792,354 A | 12/1988 | Matsuo et al. |
| 4,816,339 A | 3/1989 | Tu et al. |
| 4,861,830 A | 8/1989 | Ward, Jr. |
| 4,879,032 A | 11/1989 | Zemlin |
| 4,966,699 A | 10/1990 | Sasaki et al. |
| 4,994,503 A | 2/1991 | Harris et al. |
| 4,996,054 A | 2/1991 | Pietsch et al. |
| 5,064,871 A | 11/1991 | Sciangola |
| 5,100,992 A | 3/1992 | Cohn et al. |
| 5,145,727 A | 9/1992 | Potts et al. |
| 5,149,576 A | 9/1992 | Potts et al. |
| 5,242,995 A | 9/1993 | Kim et al. |
| 5,264,572 A | 11/1993 | Endo et al. |
| 5,322,659 A | 6/1994 | Walder et al. |
| 5,395,525 A | 3/1995 | Takano et al. |
| 5,428,123 A | 6/1995 | Ward et al. |
| 5,468,365 A | 11/1995 | Menchen et al. |
| 5,486,570 A | 1/1996 | St. Clair |
| 5,498,377 A | 3/1996 | Ozaki et al. |
| 5,543,200 A | 8/1996 | Hargis et al. |
| 5,563,056 A | 10/1996 | Swan et al. |
| 5,589,563 A | 12/1996 | Ward et al. |
| 5,720,969 A | 2/1998 | Gentile et al. |
| 5,779,897 A | 7/1998 | Kalthod et al. |
| 5,795,326 A | 8/1998 | Siman |

(Continued)

FOREIGN PATENT DOCUMENTS

| | | |
|---|---|---|
| CA | 2228505 A1 | 2/1997 |
| CA | 2439225 A1 | 9/2002 |

(Continued)

OTHER PUBLICATIONS

Fang, "Separation of liquid mixtures by membranes," Doctor of Philosophy, School of Graduate Studies and Research, Department of Chemical Engineering, University of Ottawa (1996) (216 pages).
Ho, "The effects of surface modifying macromolecules on the blood compatibility of polyethersulfone membranes Intended for biomedical applications," Master of Applied Science, Graduate Department of Chemical Engineering and Applied Chemistry, University of Toronto (1997) (167 pages).
Khayet et al., "Study on surface modification by surface-modifying macromolecules and its applications in membrane- separation processes," J. Appl Polym Sci. 89(11 ):2902-16 (2003).

(Continued)

*Primary Examiner* — Michael F Pepitone
(74) *Attorney, Agent, or Firm* — Linda S. Li; Jason S. Ngui; Andrew H. Chung

(57) ABSTRACT

The present invention relates to polyvinvyl chloride (PVC) admixtures with plasticizers and surface modifying macromolecules. In accordance with embodiments, articles formed from the compositions disclosed herein may reduce leaching of plasticizers.

21 Claims, 34 Drawing Sheets

(56) References Cited

U.S. PATENT DOCUMENTS

| | | |
|---|---|---|
| 5,879,499 A | 3/1999 | Corvi |
| 5,908,701 A | 6/1999 | Jennings et al. |
| 5,910,557 A | 6/1999 | Audenaert et al. |
| 5,929,201 A | 7/1999 | Gibbons et al. |
| 5,954,966 A | 9/1999 | Matsuura et al. |
| 5,969,082 A | 10/1999 | Kuwahara et al. |
| 6,111,049 A | 8/2000 | Sendijarevic et al. |
| 6,127,485 A | 10/2000 | Klun et al. |
| 6,127,507 A | 10/2000 | Santerre |
| 6,254,645 B1 | 7/2001 | Kellis, Jr. et al. |
| 6,348,152 B1 | 2/2002 | Kawahara et al. |
| 6,353,057 B1 | 3/2002 | He et al. |
| 6,416,838 B1 | 7/2002 | Arney et al. |
| 6,448,364 B1 | 9/2002 | Clatty et al. |
| 6,551,267 B1 | 4/2003 | Cohen et al. |
| 6,685,832 B2 | 2/2004 | Mahendran et al. |
| 6,890,321 B2 | 5/2005 | Luther et al. |
| 7,228,159 B2 | 6/2007 | Petersson et al. |
| 7,323,435 B1 | 1/2008 | Turri et al. |
| 8,071,683 B2 | 12/2011 | Mullick et al. |
| 8,178,620 B2 | 5/2012 | Mullick et al. |
| 2003/0064003 A1 | 4/2003 | Takehisa et al. |
| 2010/0133170 A1 | 6/2010 | Satoh et al. |
| 2011/0207893 A1 | 8/2011 | Mullick et al. |
| 2012/0148774 A1 | 6/2012 | Mullick et al. |
| 2012/0220724 A1 | 8/2012 | Mullick et al. |
| 2015/0344748 A1 | 12/2015 | Wohl et al. |
| 2016/0096936 A1 | 4/2016 | Swenor et al. |
| 2016/0228616 A1 | 8/2016 | Lareau et al. |
| 2016/0228632 A1 | 8/2016 | Mullick et al. |
| 2016/0310641 A1 | 10/2016 | Santerre et al. |

FOREIGN PATENT DOCUMENTS

| | | |
|---|---|---|
| CA | 2349989 A1 | 12/2002 |
| CA | 2604696 A1 | 1/2007 |
| CA | 2672593 C | 6/2008 |
| CA | 2701186 A1 | 4/2009 |
| CA | 2703017 A1 | 4/2009 |
| CA | 2716502 A1 | 11/2010 |
| CA | 2971113 A1 | 6/2016 |
| GB | 1600600 A | 10/1981 |
| JP | H03-244649 A | 10/1991 |
| JP | H04-72341 A | 3/1992 |
| JP | 2006-117804 A | 5/2006 |
| JP | 2009-504851 A | 2/2009 |
| JP | 2010-513596 A | 4/2010 |
| JP | 2012-501377 A | 1/2012 |
| JP | 2016-52525 A | 4/2016 |
| WO | 199526993 A1 | 10/1995 |
| WO | 199706195 A1 | 2/1997 |
| WO | 199834718 A1 | 8/1998 |
| WO | 199851725 A1 | 11/1998 |
| WO | 0149925 A1 | 7/2001 |
| WO | 2004056459 A1 | 7/2004 |
| WO | 2005058999 A1 | 6/2005 |
| WO | 2007084514 A2 | 7/2007 |
| WO | 2008076345 A1 | 6/2008 |
| WO | 2010009191 A2 | 1/2010 |
| WO | 2010025398 A1 | 3/2010 |
| WO | 2011072398 A1 | 6/2011 |
| WO | 2013180531 A1 | 12/2013 |
| WO | 2015/124236 A1 | 8/2015 |
| WO | 2016054733 A1 | 4/2016 |
| WO | 2016095042 A1 | 6/2016 |
| WO | 2016154034 A1 | 9/2016 |
| WO | 2017195035 A1 | 11/2017 |
| WO | 2018218347 A1 | 12/2018 |
| WO | 2018218348 A1 | 12/2018 |

OTHER PUBLICATIONS

Shimizu et al., "Synthesis and characterization of fluorine-containing aromatic polyethers from tetrafluoroisophthalonitrile and bisphenols," J Polym Sci A Polym Chem. 25:2385-2393 (1987).

Snaterse et al., "Antibiotic-based catheter lock solutions for prevention of catheter-related bloodstream infection: a systematic review of randomised controlled trials," J Hosp Infect. 75(1):1-11 (2010).

Suk et al., "Effects of surface modifying macromolecule (SMM) on the properties of polyethersulfone membranes," Desalination. 149:303-307 (2002).

Sherertz et al., "Education of physicians-in-training can decrease the risk for vascular catheter infection," Ann Intern Med. 132(8):641-8 (2000).

Sukumar et al., "Synthesis and thermal studies of block copolymers from NR and MDI-based polyurethanes," J Appl Polym Sci. 111:19-28 (2009).

Tang et al., "Application of macromolecular additives to reduce the hydrolytic degradation of polyurethanes by lysosomal enzymes," Biomaterials. 18(1):37-45 (1997).

Tang et al., "Surface modifying macromolecules for improved resistance of polyurethanes to biodegradation," Annual Meeting of the Canadian Biomaterials Society, July 10-12, Quebec City, Canada (1994) (3 pages).

Tang et al., "Synthesis of surface-modifying macromolecules for use in segmented polyurethanes," J Appl Polym Sci. 62:1133-45 (1996).

Tang et al., "The use of surface modifying macromolecules to inhibit biodegradation of segmented polyurethanes," Trans 20th Annual Meeting Soc Biomater. 62. Apr. 5-9, Boston, MA (1994) (2 pages).

Tang et al., "Use of surface-modifying macromolecules to enhance the biostability of segmented polyurethanes," J Biomed Mater Res. 35(3):371-81 (1997).

Tang, "Surface modifying macromolecules for biomaterials," Master of Applied Science, Department of Chemical Engineering, University of Ottawa (1995) (172 pages).

Teichgraber et al., "Central venous access catheters: radiological management of complications," Cardiovasc Intervent Radiol. 26(4):321-33 (2003).

Urquhart et al., "TOF-SIMS analysis of a 576 micropatterned copolymer array to reveal surface moieties that control wettability," Anal Chem. 80(1): 135-42 (2008).

Winnett et al., "Trisodium citrate 46.7% selectively and safely reduces staphylococcal catheter-related bacteraemia," Nephrol Dial Transplant. 23(11):3592-8 (2008).

Boyer et al., "Severe clotting during extracorporeal dialysis procedures," Seminars in Dialysis, 4(2):69-71 (1991).

Dwyer, "Surface-treated catheters-a review," Seminars in Dialysis, 21(6):542-6 (2008).

Siegman-Igra et al., "Diagnosis of vascular catheter-related bloodstream infection: a meta-analysis," J Clin Microbiol. 35(4):928-36 (1997).

Compound 1
PPO = poly(propylene oxide)

Compound 2
HLBH = hydrogenated polybutadiene

Compound 3

Compound 4
PEB = poly(ethylene-co-butylene)

Compound 5

PCN = poly(2,2-dimethyl-1,3-propylenecarbonate)

Compound 6

Compound 7

Compound 8
LBHP = polybutadiene

Compound 9
PEGA = poly(diethylene glycol)adipate

Compound 10
PDP = (diethylene glycol-ortho phthalic anhydride) polyester

Compound 11
PTMO = polytetramethylene oxide

Compound 12

Compound 13

Compound 14

Compound 15

Compound 16

Compound 20

Compound 21

Compound 25

Compound 27 (m = 25)

Compound 28

Compound 29

Compound 30

Compound 31

Compound 32

Compound 33

Compound 34

Compound 35

Compound 36

Compound 37

Compound 38

Compound 39
MW of the diol = 8000 Da, PEG = 80%, PPG = 20%
PLN8K-1246E

Compound 40
MW of the diol = 8000 Da, PEG = 80%, PPG = 20%

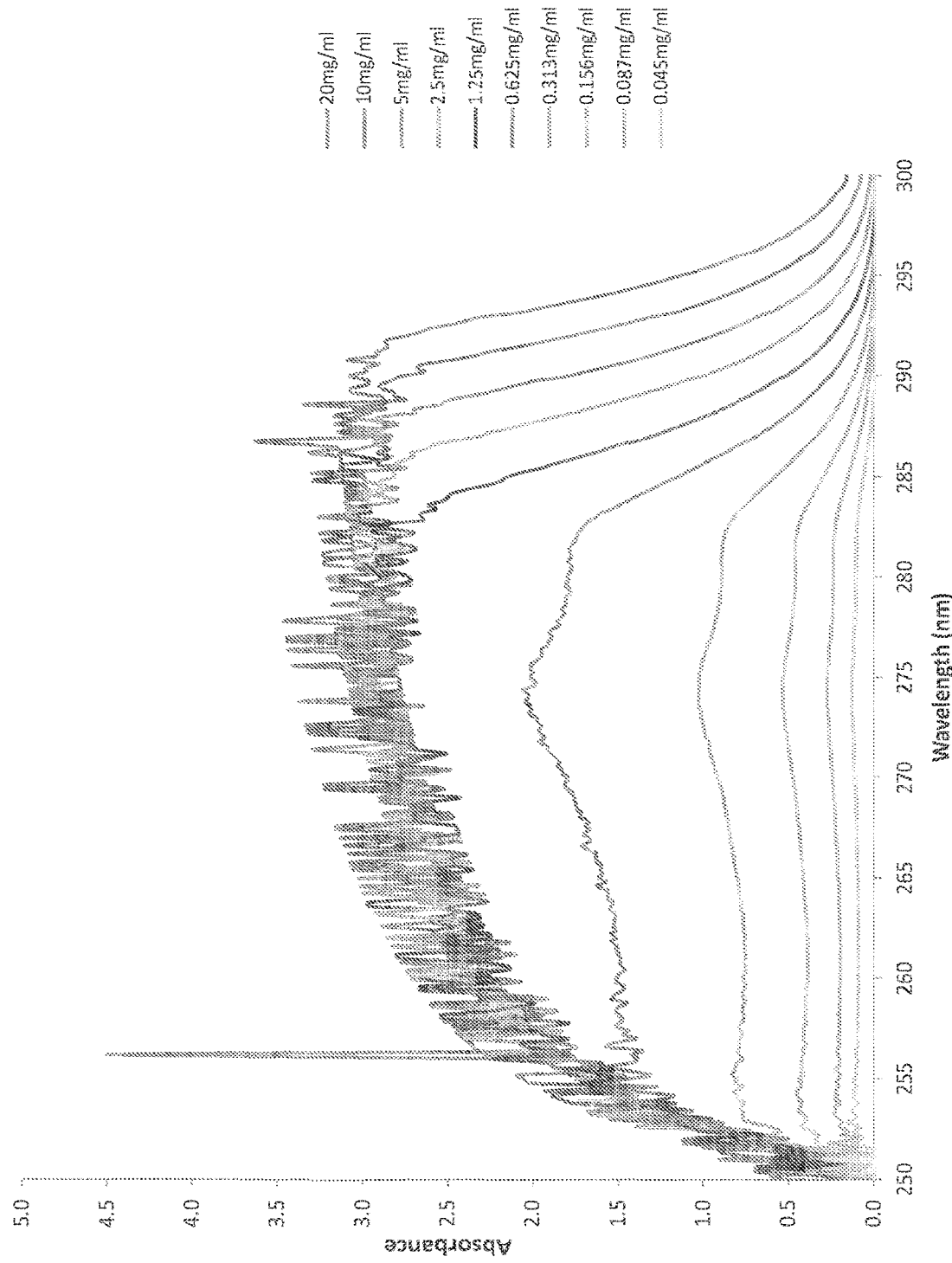
Figure 31. Absorbance spectrum of DEHP in hexane at different concentrations Figure 32A. Absorbance of DEHP at 275nm in hexane at different concentrations.

| Abs @ 275nm | DEHP (mg/ml) | |
|---|---|---|
| | Empirical | Theoretical |
| 2.445 | 0.800 | 0.764 |
| 2.548 | 0.800 | 0.796 |
| 2.548 | 0.800 | 0.796 |
| 1.323 | 0.400 | 0.413 |
| 1.344 | 0.400 | 0.420 |
| 1.399 | 0.400 | 0.437 |
| 0.635 | 0.200 | 0.198 |
| 0.687 | 0.200 | 0.215 |
| 0.721 | 0.200 | 0.225 |
| 0.508 | 0.100 | 0.159 |
| 0.327 | 0.100 | 0.102 |
| 0.344 | 0.100 | 0.107 |
| 0.149 | 0.050 | 0.047 |
| 0.166 | 0.050 | 0.052 |
| 0.151 | 0.050 | 0.047 |
| 0.054 | 0.025 | 0.017 |
| 0.067 | 0.025 | 0.021 |
| 0.075 | 0.025 | 0.023 |

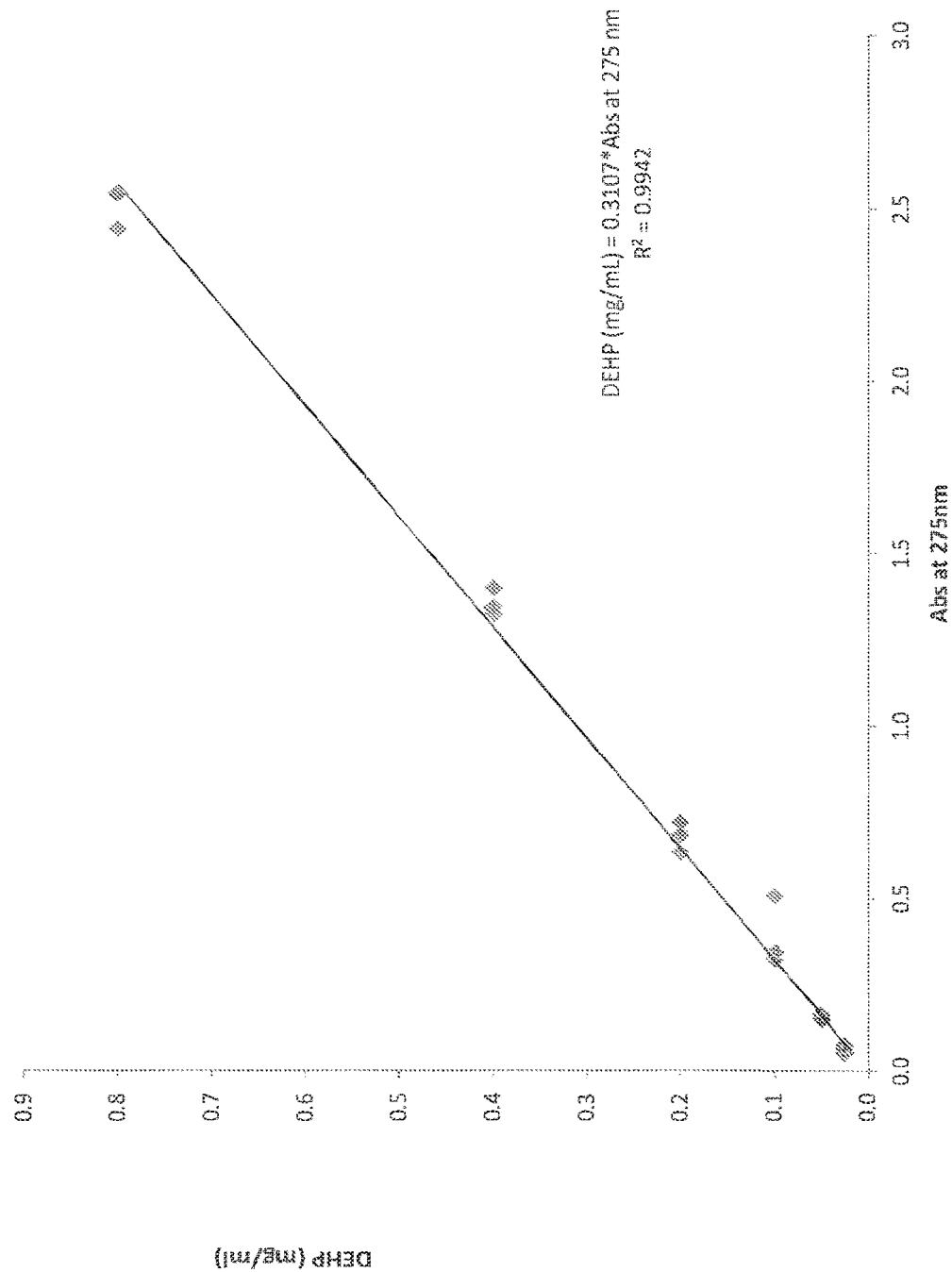
Figure 32B. DEHP concentration vs. absorbance at 275nm

PLASTICIZED PVC ADMIXTURES WITH SURFACE MODIFYING MACROMOLECULES AND ARTICLES MADE THEREFROM

This application is a continuation of and claims priority to U.S. application Ser. No. 16/386,409, filed on Apr. 17, 2019, which claims the benefit of U.S. Provisional Application Ser. No. 62/409,759, filed on Oct. 18, 2016, applications which are incorporated by reference herein in their entirety

FIELD OF THE INVENTION

The present invention relates to polyvinvyl chloride (PVC) admixtures with plasticizers and surface modifying macromolecules, and compositions and methods of preparing articles made from the admixtures.

BACKGROUND

One of the most common base polymers used in molded articles (e.g., medical devices, tubing) is polyvinylchloride (PVC). However, PVC is hard and brittle, and thus plasticizers are often added to make the PVC flexible and more appropriate for a particular use. Di-(2-ethylhexyl)-phthalate (DEHP) is the most widely used plasticizer in PVC and medical devices made from PVC. However, DEHP is not chemically bound to PVC and leaches from the PVC with time and use. The potential for DEHP to produce adverse effects in humans has been the subject of considerable discussion and debate in the scientific community, and thus there exists a need for PVC admixtures that exhibit reduced leaching of plasticizers.

SUMMARY OF THE INVENTION

The invention is directed to PVC admixtures including one or more plasticizers and surface modifiers that reduce the amount of the leaching of plasticizing agent from the admixture. In particular embodiments, the admixtures are transparent.

In a first aspect, the invention features a blended composition including from 20% to 99.9% (w/w) of a polyvinyl chloride base polymer (e.g. 30%±10%, 40%±10%, 50%±10%, 60%±10%, 70%±10%, 80%±10%, or 90%±10% (w/w)), from 1% to 80% (w/w) of a plasticize (e.g., 5%±4%, 15%±10%, 20%±15%, 30%±10%, 40%±10%, 50%±10%, 60%±10%, 70%±10%, or 80%±10% (w/w)), and from 0.01% to 20% (w/w) of a surface modifying macromolecule (SMM) (e.g., 0.2%±0.1%, 0.3%±0.1%, 0.4%±0.2%, 1.0%±0.5%, 1.5%±0.5%, 2.0%±0.5%, 3.0%±0.5%, 3.5%±0.5%, 4.0%±0.5%, 4.5%±1.5%, 5%±2.0%, 6%±2%, 7%±4%, 8%±4%, 10%±3%, 12%±3%, 14%±3%, or 16%±4% (w/w)). In some embodiments, the blended composition includes from 10% to 50% (w/w) plasticizer. In still other embodiments, the blended composition includes from 20% to 45% (w/w) plasticizer. In some embodiments, the amounts of the polyvinyl chloride base polymer, the plasticizer, and the SMM in the blended composition produce a miscible admixture. The plasticizer in the blended composition can be selected from the group consisting of phthalates, trimellitates, and adipates. For example, the plasticizer can be an orthophthalate, such as di-(2-ethyl hexyl)phthalate (DEHP). Alternatively, the plasticizer can be tri-(2-ethylhexyl)trimellitate (TOTM) or dioctyl terepththalate (DENT).

In certain embodiments, the SMM in the blended composition is described by the formula:

wherein: (i) A comprises poly(diethylene glycol)adipate, (neopentyl glycol-ortho phthalic anhydride) polyester, (diethylene glycol-ortho phthalic anhydride) polyester, (1,6-hexanediol-ortho phthalic anhydride) polyester, polypropylene oxide, polyethylene oxide, or polytetramethylene oxide; (ii) B comprises a urethane; (iii) $F_T$ is a polyfluoroorgano group, and (iv) n is an integer from 1 to 10.

In some embodiments, the blended composition includes from 60% to 80% (w/w) of the polyvinyl chloride base polymer, from 20% to 40% (w/w) of the plasticizer, and from 0.5% to 5% (w/w) of the SMM.

In some embodiments, the blended composition includes one or more additives selected from the group consisting of a heat stabilizer, an impact modifier, a process aid, a lubricant, a filler, a flame retardant, a pigment, a blowing agent, a biocide, a viscosity modifier, an antistatic agent, an antioxidant, a UV absorber, an antifogging agent, and a bonding agent.

In a related aspect, the invention features an article is made from the blended composition of the invention. In some embodiments, the article is transparent. In some embodiments, the article is an implantable device (e.g., an implantable device that contacts body fluids or a device in contact with fluids that enter the body). In particular embodiments, the article is PVC tubing or a PVC bag (e.g., a bag for infusing saline, plasma, or blood into a subject).

In some embodiments, the article exhibits reduced leaching of the plasticizing agent.

In certain embodiments, the article has a hardness value on the shore A scale or the shore D scale. For example, the article can have a hardness of between 60A and 85D (e.g., 60A to 95 A, 75A to 90A, 85A to 100A, 5D to 50D, or 25D to 85D).

The invention further features a method for making an article of the invention by preparing a blended composition of the invention and processing the composition to form or to coat the article. In some embodiments of the method, processing includes one or more of extruding, injection molding, calendaring, mixing, spraying, dipping, or casting the blended composition. In some embodiments of the method, wherein the article is transparent. In some embodiments of the method the article exhibits reduced leaching of the plasticizing agent.

Definitions

The term "about," as used herein, refers to a value that is ±10% of the recited number.

The term "base polymer," as used herein, refers to a polymer having a theoretical molecular weight of greater than or equal to 20 kDa (e.g., greater than or equal to 50 kDa, greater than or equal to 75 kDa, greater than or equal to 100 kDa, greater than or equal to 150 kDa, or greater than 200 kDa). The base polymers of the present invention are polyvinyl chlorides (PVCs).

As used herein the term "surface modifying macromolecule" or "SMM" refers to a segmented compound of any one of formulae (I), (II), (III), (IV), (V), (VI), (VII), (VIII), (IX), (X), (XI), (XII), (XIII), (XIV), (XV), (XVI), and (XVII). Certain SMMs can have a theoretical molecular weight of less than or equal to 20 kDa (e.g., less than or equal to 10 kDa). Certain SMMs can have a theoretical molecular weight of greater than or equal to 200 Da (e.g., greater than or equal to 300 Da). Non-limiting examples of SMMs include those having a theoretical molecular weight of from 500 to 10,000 Daltons, from 500 to 9,000 Daltons, from 500 to 5,000 Daltons, from 1,000 to 10,000 Daltons, from 1,000

As used herein, "C" refers to a chain terminating group. Exemplary chain terminating groups include monofunctional groups containing an amine, alcohol, or carboxylic acid functionality.

The terms "LinkB," as used herein, refers to a coupling segment linking two oligomeric segments and a surface active group. Typically, LinkB has a molecular weight ranging from 40 to 700. Preferably, The term "LinkB," as used herein, refers to a coupling segment linking two oligomeric segments and a surface-active group. Typically, LinkB has a molecular weight ranging from 40 to 700. Preferably, LinkB can be selected from the group of functionalized diamines, diisocyanates, disulfonic acids, dicarboxylic acids, diacid chlorides, and dialdehydes, where the functionalized component has secondary functional group, through which a surface-active group is attached. Such secondary functional groups can be esters, carboxylic acid salts, sulfonic acid salts, phosphonic acid salts, thiols, vinyls, and primary or secondary amines. Terminal hydroxyls, amines, or carboxylic acids of an oligomeric segment intermediate can react with a diamine to form an oligo-amide; react with a diisocyanate to form an oligo-urethane, an oligo-urea, or an oligo-amide; react with a disulfonic acid to form an oligo-sulfonate or an oligo-sulfonamide; react with a dicarboxylic acid to form an oligo-ester or an oligo-amide; react with a diacyl dichloride to form an oligo-ester or an oligo-amide; or react with a dicarboxaldehyde to form an oligo-acetal or an oligo-imine.

The term "linker with two terminal carbonyls," as used herein, refers to a divalent group having a molecular weight of between 56 Da and 1,000 Da, in which the first valency belongs to a first carbonyl, and a second valency belongs to a second carbonyl. Within this linker, the first carbonyl is bonded to a first carbon atom, and the second carbonyl is bonded to a second carbon atom. The linker with two terminal carbonyls can be a small molecule dicarbonyl (e.g., norbornene-dicarbonyl, benzene-dicarbonyl, biphenyl-dicarbonyl, alkylene-dicarbonyl (e.g., succinoyl, glutaryl, adipoyl, pimeloyl, suberoyl, etc.)

The term "molecular weight," as used herein, refers to a theoretical weight of an Avogadro number of molecules of identical composition. As preparation of a SMM can involve generation of a distribution of compounds, the term "molecular weight" refers to a molar mass of an idealized structure determined by the stoichiometry of the reactive ingredients. Thus, the term "molecular weight," as used herein, refers to a theoretical molecular weight.

The term "oligomeric linker," as used herein, refers to a divalent group containing from two to fifty bonded to each other identical chemical moieties. The chemical moiety can be an alkylene oxide (e.g., ethylene oxide).

The term "oligomeric segment," as used herein, refers to a relatively short length of a repeating unit or units, generally less than about 50 monomeric units and theoretical molecular weights less than 10,000 Daltons, but preferably <7,000 Daltons and in some examples, <5,000 Daltons. In certain embodiments, oligo is selected from the group consisting of polyurethane, polyurea, polyamide, polyalkylene oxide, polycarbonate, polyester, polylactone, polysilicone, polyethersulfone, polyolefin, polyvinyl, polypeptide, polysaccharide, and ether and amine linked segments thereof.

The term "oxycarbonyl bond," as used herein, refers to a bond connecting an oxygen atom to a carbonyl group. Exemplary oxycarbonyl bonds can be found in esters and urethanes. Preferably, the oxycarbonyl bond is a bond in an ester.

The term "plasticized resin," or "plasticized PVC," as used herein, refers to the resulting product of a PVC base polymer and plasticizer.

The term "plasticizer," as used herein, refers to a substance that when added to the PVC base polymer, renders the resulting resin, known as a "plasticized resin" more.

The term "polyalkylene," when used herein in reference to a base polymer, refers to a base polymer composed of linear or branched alkylene repeating units having from 2 to 4 carbon atoms and/or optionally a cyclic olefin of 3 to 10 carbon atoms (e.g., norbornene or tetracyclododecene). Each alkylene repeating unit is optionally substituted with one substituent selected from the group consisting of chloro, methoxycarbonyl, ethoxycarbonyl, hydroxyethoxycarbonyl, pyrrolidone, hydroxy, acetoxy, cyano, and phenyl. Non-limiting examples of polyalkylene base polymers include polystyrene, a cyclic olefin polymer (COP), a cyclic olefin copolymer (COC), MABS, SAN, SMMA, MBS, SB, and polyacrylate (e.g., PMMA).

The term "polyfluoroorgano group," as used herein, refers to a hydrocarbon group that may be optionally interrupted by one, two, or three non-contiguous oxygen atoms, in which from two to fifty nine hydrogen atoms were replaced with fluorine atoms. The polyfluoroorgano group contains one to thirty carbon atoms. The polyfluoroorgano group can contain linear alkyl, branched alkyl, or aryl groups, or any combination thereof. The polyfluoroorgano group (e.g., polyfluoroalkyl) can be a "polyfluoroacyl," in which the carbon atom, through which the polyfluoroorgano group (e.g., polyfluoroalkyl) is attached to the rest of the molecule, is substituted with oxo. The alkyl chain within polyfluoroorgano group (e.g., polyfluoroalkyl) can be interrupted by up to nine oxygen atoms, provided that two closest oxygen atoms within polyfluoroorgano are separated by at least two carbon atoms. When the polyfluoroorgano consists of a linear or branched alkyl optionally substituted with oxo and/or optionally interrupted with oxygen atoms, as defined herein, such group can be called a polyfluoroalkyl group. Some polyfluoroorgano groups (e.g., polyfluoroalkyl) can have a theoretical molecular weight of from 100 Da to 1,500 Da. A polyfluoroalkyl can be $CF_3(CF_2)_r(CH_2CH_2)_p-$, where p is 0 or 1, r is from 2 to 20, or $CF_3(CF_2)_s(CH_2CH_2O)_X-$, where X is from 0 to 10, and s is from 1 to 20. Alternatively, polyfluoroalkyl can be $CH_mF_{(3-m)}(CF_2)_rCH_2CH_2-$ or $CH_mF_{(3-m)}(CF_2)_s(CH_2CH_2O)_X-$, where m is 0, 1, 2, or 3; X is from 0 to 10; r is an integer from 2 to 20; and s is an integer from 1 to 20. In particular embodiments, X is 0. In certain embodiments, polyfluoroalkyl is formed from 1H,1H,2H,2H-perfluoro-1-decanol; 1H,1H,2H,2H-perfluoro-1-octanol; 1H,1H,5H-perfluoro-1-pentanol; or 1H,1H, perfluoro-1-butanol, and mixtures thereof. In other embodiments, polyfluoroalkyl is perfluoroheptanoyl. In still other embodiments, polyfluoroalkyl is $(CF_3)(CF_2)_5CH_2CH_2O-$, $(CF_3)(CF_2)_7CH_2CH_2O-$, $(CF_3)(CF_2)_5CH_2CH_2O-$, $CHF_2(CF_2)_3CH_2O-$, $(CF_3)(CF_2)_2CH_2O-$, or $(CF_3)(CF_2)_5-$. In still other embodiments the polyfluoroalkyl group is $(CF_3)(CF_2)_5-$, e.g., where the polyfluoroalkyl group is bonded to a carbonyl of an ester group. In certain embodiments, polyfluoroorgano is $-(O)_q-[C(=O)]_r(CH_2)O(CF_2)_pCF_3$, in which q is 0 and r is 1, or q is 1 and r is 0; o is from 0 to 2; and p is from 0 to 10.

The term "PVC", as used herein, refers to poly(vinyl chloride) base polymers. The PVCs contemplated by the present disclosure have varying properties, and may be graded by manufacturers according to said one or more properties including, but not limited to, molecular weight, degree of polymerization, inherent viscosity, bulk density, and weight percent of volatile matter or fillers.

The term "surface-active group," as used herein, refers to a hydrophobic group bonded to a segment of a SMM. For example, the surface-active group can be positioned to cap two, three, or four termini of the central, segmented polymeric portion of the SMM and/or can be attached to one or more side chains present in the central polymeric portion of the surface modifier. Examples of surface-active groups include, without limitation, polydimethylsiloxanes, polyethylene oxides, hydrocarbons, polyfluoroalkyl, fluorinated polyethers, and combinations thereof.

The term "transparent," as used herein, refers to the plasticized resin material of invention (e.g., an implantable medical device) having a parallel optical transmittance of greater than or equal to 55% when measured using a plate of the thickness of at least 0.5 mm using light having a wavelength of 450 nm. For example, a method of determining a parallel optical transmittance is described in "Test Methods for Plastic Containers for Pharmaceutical Products" in General Tests of the Japanese Pharmacopoeia, 15$^{th}$ Edition, The term "reduced leaching," as used herein, refers to an article of the invention that exhibits reduced leaching of the plasticizing agent at 6 hours following a challenge in hexane using the method described in Example 2. The leaching of the plasticizing agent can be reduced by at least 1%, 3%, 5%, 8%, 10%, 15%, or more.

Other features and advantages of the invention will be apparent from the Drawings, Detailed Description, and the claims.

BRIEF DESCRIPTION OF THE DRAWINGS

FIG. 31 shows an absorption spectrum of DEHP in hexane at differing concentrations
FIG. 32A shows a table of the absorbance of DEHP at 275 nm in hexane at different concentrations.
FIG. 32B shows a calibration curve of DEHP concentration verses absorbance at 275 nm.

DETAILED DESCRIPTION

Figure 1A:
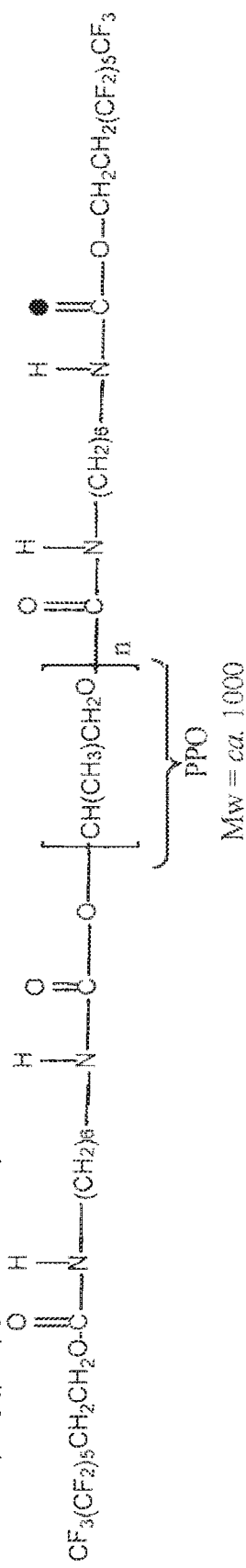
FIG. 1A shows a structure of compound 1.
Figure 1B:
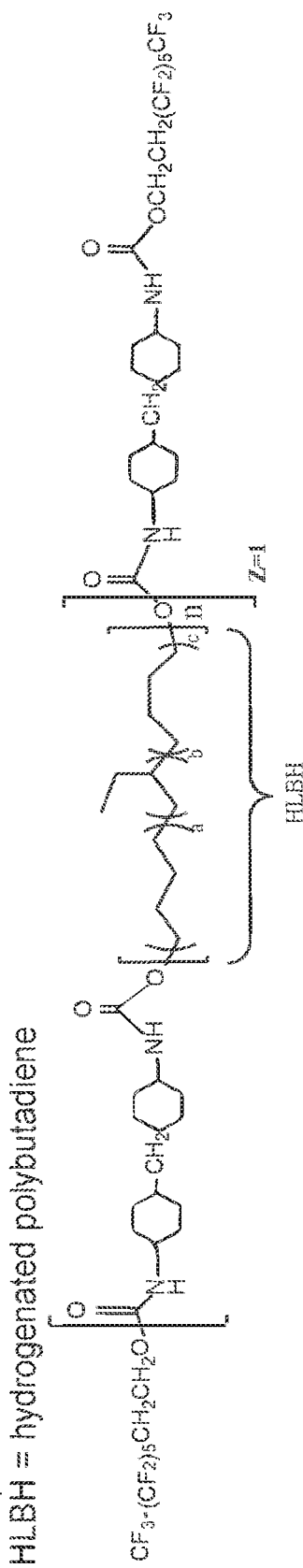
FIG. 1B shows a structure of compound 2.

The present invention relates to articles formed from a plasticized resin formed from a base polymer plasticized with a plasticizer and admixed with one or more SMMs to provide a plasticized resin article exhibiting a reduction in plasticizer leaching. The base polymer contemplated by the present invention is PVC. In accordance with aspects of the invention, articles formed from the modified resin may be medical devices. The formed medical devices, or components of medical devices, may be intended for subcutaneous, intravascular, or transcutaneous use. The devices may, for example, be implantable medical devices used in patient's vasculature, or may be implanted in other blood-contacting and/or intracorporeal and extracorporeal environments.

PVC, absent additional processing, is a white, rigid, brittle solid. Additives are incorporated into the PVC base polymer to modify the resin properties to suit the end use specification. Additives include, but are not limited to, heat stabilizers, impact modifiers, process aids, lubricants, fillers, flame retardants, pigments, blowing agents, biocides, viscosity modifiers, antistatic agents, antioxidants, UV absorbers, antifogging agents, bonding agents, and plasticizers. To render the PVC suitable for medical devices, a plasticizer is incorporated into the base polymer to provide a plasticized resin that is flexible and in some embodiments, translucent. Plasticizers, however, may migrate in the plasticized resin and leach out of the medical device. Certain common plasticizers have been shown to produce adverse effects in experimental animals, and thus reducing the amount of plasticizer leaching into the body from plasticized PVC medical devices is of significant importance.

The articles formed from the modified resin of the present disclosure may be advantageous over known articles fabricated from traditional plasticized PVC (e.g., articles formed from DEHP-plasticized PVC resin). In particular, the articles formed from the modified resin of the present disclosure can exhibit reduced leaching of the plasticizing agent from the article in comparison to articles formed from plasticized resin without SMM.

PVC Base Polymer Resins

PVC base polymer is available from numerous manufacturers in many different formulations and configurations. There are four types of PVC resins grouped according to method of production, e.g., the way in which vinyl chloride monomer is polymerized.

Suspension Grade PVC

Suspension grade PVC is the most prevalent type of PVC, and is made by polymerizing fine dispersed vinyl chloride monomer droplets suspended in water. When polymerization is complete, the resulting slurry is centrifuged and the PVC cake is dried. The particle size of suspension grade PVC resin range from about 50 to about 250 microns and have porous, popcorn-like structures which readily absorb additives, such as plasticizers. The structure of suspension grade PVC particles can be modified by selecting suitable suspending agents and polymerization catalysts. Less porous suspension grade PVC particles are widely used in high volume, rigid, and/or unplasticized applications, including but not limited to, pipes, windows, siding, ducting, and other construction materials. Suspension grades of a coarser particle size and porous structure readily absorb large quantities of plasticizer at temperatures as low as 80° C. and are used in plasticized applications, including but not limited to, injection molding and extrusion applications.

Emulsion Grade PVC

Emulsion/dispersion polymerized PVC, also referred to as paste grade resin, is used almost exclusively in plastisols. Paste grade resin is produced by spray drying an emulsion of PVC in water. The production of paste grade resin is more energy intensive than other PVC production methods and less pure as a result of the emulsifiers and catalysts used in production remaining in the final product. Moreover, its electrical properties and clarity is also poor as a result. Paste grade resin is more compact in structure than suspension grade resin and does not readily absorb plasticizer. Temperatures in excess of 160° C.-180° C. are needed to drive plasticizer into the resin during curing. Vinyl flooring is commonly made from emulsion grade PVC.

Bulk Polymerized PVC

Bulk polymerization provides the purest form of PVC resin as no emulsifying or suspending agents are used in manufacture. Bulk polymerized PVC has high transparency and is mainly made available at low molecular weights and used as unplasticized foils for packaging and other calendered/extruded transparent films.

Copolymer PVC

Vinyl chloride can be copolymerized with co-monomers, e.g., vinyl acetate, to give a range of resins with unique properties. Copolymer of vinyl chloride and vinyl acetate, for example, has good solubility in solvents and is widely used in vinyl printing inks and solvent cements. Copolymers provide the unique ability to manufacture articles comprised of predominantly additives, with the copolymer resin accounting for only a small fraction of the end product.

In addition to the way in which PVC is made, PVC products are also classified by their mechanical properties and uses. For example, unplasticized PVC (U-PVC), also referred to a rigid PVC, is referred to by types. U-PVC Type I grade is most common, and is a high corrosion resistant material with normal impact properties used where chemical attack and degradation are of concern. Type II grade is an impact modified formula which increases the ability of the material to withstand shock or impact, but has lower chemical resistance relative to type I. The physical properties of type I and type II grade rigid PVC generally confirm to ASTM-D-1784 (ISO 1163).

PVC Resin Classification

In addition to polymerization process, resins are classified by their Fikentscher K-value. K value is an indicator of molecular weight and degree of polymerization. The majority of commercial grade PVC resins have a K-value of between about 40 and about 80, with higher K-value resins used for specialty processes. Alternatively, PVC polymers may be identified by their viscosity numbers. The higher the K value, the better are the mechanical and electrical properties of the material, and the higher are its processing temperatures.

Low K value resins, for example, those with K values below 60, have poor mechanical properties but processing is easiest. Low K-value resins are thus often selected for injection molding, blow molding, and clear calendered packaging film applications.

Medium K value resins, for example those with K values between about 60 and 70, are most popular. They have a good balance of mechanical properties and processability. Unplasticized PVC is generally made from less porous grades, while plasticized applications general use more porous grades.

High K value resins, for example, those with a K value of between about 70 and 80 provide the best mechanical properties but are more difficult to process and require more plasticizer to achieve the same flexibility as lower K value resins. Paste grade resin with a high K value is often used in industrial coating and flooring applications, and high K value suspension grade resin is often used in high performance cable insulations.

Specialty grades with differing properties are made by numerous manufacturers. These products are generally named by manufacturer-specific nomenclature. PVC resins can be selected by intended application, bulk density, percent volatiles, degree of molecular dispersion, or other properties. For example, Formosa Plastics makes suspension grade resins with K values ranging from 48-80 having a variety of different properties. They also offer emulsion products having higher K values about 68-80 in a wide range of molecular weights and viscosities for specialty applications. The blended compositions of the invention can include any of the grades of PVC described herein.

Table 1 provides K values of various PVC (plasticized and unplasticized grades).

TABLE 1

| Process | PVC-U | | | PVC-P | | |
|---|---|---|---|---|---|---|
| | Emulsion | Suspension K values | Bulk | Emulsion | Suspension K values | Bulk |
| Calendering | | | | | | |
| General Extrusion (PVC-U) | 75-80 | — | — | 60-80 | 60-70 | — |
| Tubes | 70 | 76-78 | 67-68 | — | — | — |
| Sheets and flat film | 60-65 | 60 | 60 | — | — | — |
| Blown film | 60 | 57-50 | 60 | — | — | — |

TABLE 1-continued

|  | PVC-U | | | PVC-P | | |
|---|---|---|---|---|---|---|
| Process | Emulsion | Suspension K values | Bulk | Emulsion | Suspension K values | Bulk |
| Extrusion (PVC-P) | | | | | | |
| General | — | — | — | 65-70 | 65-70 | 65-70 |
| Blow molding | — | 57-60 | 58-60 | — | 65-80 | 60-65 |
| Injection Molding | — | 55-60 | 56-60 | — | 65-70 | 55-60 |

Plasticizers

There are two main groups of plasticizers, internal and external plasticizers. Internal plasticizers are those that are actually a part of the polymer molecule, e.g., a second monomer copolymerized into the polymer structure, thereby making is less ordered, and therefore more difficult for the chains to fit closely together, thus softening the polymer. External plasticizers are the most important as far as commercial application is concerned. They provide a more satisfactory combination of properties and allow for more formulating flexibility than if the plasticizer were added during the polymerization process. In accordance with embodiments, the plasticizers contemplated by the present invention are external plasticizers.

External plasticizers are compounds of low vapor pressure which, without chemical reaction, interact with the polymer, mainly at elevated temperature, by means of their solvent or swelling power. There are more than 300 different known plasticizers, of which about 100 are in commercial use.

Plasticizers may be phthalates, trimellitates, adipates, and other chemistries.

Trimellitates may be used in applications where resistance to high temperatures is required and include, but are not limited to, trimethyl trimellitate (TMTM), tri-(2-ethylhexyl) trimellitate (TEHTM-MG or TOTM), tri-(n-octyl,n-decyl) trimellitate (ATM), tri-(heptyl,nonyl) trimellitate (LTM), and n-octyl trimellitate (OTM)

Adipate-based plasticizers are used for low temperature applications or resistance to ultraviolet light. Examples of adipates include, but are not limited to, di(2-ethylhexyl) adipate (DEHA), dimethyl adipate, (DMAD), monomethyl adipate (MMAD), dioctyl adipate (DOA), dibutyl sebacate (DBS), dibutyl maleate (DBM), and diisobutyl maleate (DIBM).

Other plasticizers include benxoates, terepththalates such as dioctyl terepththalate (DENT), 1,2-cyclohexane dicarboxylic acid diisononyl ester (BASF trademark: Hexamoll DINCH), epoxidized vegetable oils, alkyl sulphonic acid phenyl ester (ASE), sulfonamides including, but not limited to, N-ethyl toluene sulfonamide (o/p ETSA), ortho and para isomers, N-(2-hydroxypropyl) benzene sulfonamide (HP BSA) and N-(n-butyl) benzene sulfonamide (BBSA-NBBS), organophosphates, including but not limited to tricresyl phosphate (TCP), tributyl phosphate (TBP), glycols/polyethers, triethylene glycol dihexanoate (3G6, 3GH), tetraethylene glycol diheptanoate (4G7), polymeric plasticizers, and polybutene.

Moreover, plasticizers with enhanced biodegradability and fewer chemical effects are being developed and include, but are not limited to, acetylated monoglycerides, alkyl citrates, triethyl citrate (TEC), acetyl triethyl citrate (ATEC), tributyl citrate (TBC), acetyl tributyl citrate (ATBC), which are notably compatible with PVC and vinyl chloride copolymers, trioctyl citrate (TOC), acetyl trioctyl citrate (ATOC), trihexyl citrate (THC), acetyl trihexyl citrate (ATHC), compatible with PVC, butyryl trihexyl citrate (BTHC, trihexyl o-butyryl citrate), compatible with PVC, trimethyl citrate (TMC), compatible with PVC, and epoxidized soybean oil (ESBO)

The most commonly used plasticizers in PVC applications, however, are orthophthalates.

Orthophthalates account for about 80% of the global plasticizer market of which about 95% are used to make plasticized PVC. Orthophthalates are manufactured by reacting phthalic ayhydride with $C_1$-$C_{13}$ alcohols. Notably, phthalates with longer carbon chains are not compatible with PVC. A list of orthophthalates, their commonly used acronyms, and their Chemical Abstract Services number are shown in Table 2.

TABLE 2

| Name | Acronym | Cas |
|---|---|---|
| n-Octyl n-decyl phthalate (ODP) | ODP | 119-07-3 |
| Di(2-Propyl Heptyl) phthalate (DPHP) | DPHP | 53306-54-0 |
| Diundecyl phthalate (DUP) | DUP | 3648-20-2 |
| Diisononyl phthalate (DINP) | DINP | 28553-12-0 |
| Diisodecyl phthalate (DIDP) | DIDP | 68515-49-1 |
| Diisoundecyl phthalate (DIUP) | DIUP | 85507-79-5 |
| Di-n-propyl phthalate (DPP) | DPP | 131-16-8 |
| Di-n-butyl phthalate (DBP) | DBP | 84-74-2 |
| Butyl cyclohexyl phthalate (BCP) | BCP | 84-64-0 |
| Di-n-pentyl phthalate (DNPP) | DNPP | 131-18-0 |
| Benzyl butyl phthalate (BBP) | BBP | 85-68-7 |
| Di-n-hexyl phthalate (DNHP) | DNHP | 84-75-3 |
| Butyl decyl phthalate (BDP) | BDP | 89-19-0 |
| Di(n-octyl) phthalate (DNOP) | DNOP | 117-84-0 |
| Diisohexyl phthalate (DHP) | DHP | 146-50-9 |
| Diisoheptyl phthalate (DIHP) | DIHP | 41451-28-9 |
| Diisooctyl phthalate (DIOP) | DIOP | 27554-26-3 |
| Diisotridecyl phthalate (DTDP) | DTDP | 68515-47-9 |
| Ditridecyl phthalate (DTDP) | DTDP | 119-06-2 |
| Dimethyl phthalate (DMP) | DMP | 131-11-3 |
| Diethyl phthalate (DEP) | DEP | 84-66-2 |
| Diallyl phthalate (DAP) | DAP | 131-17-9 |
| Diisobutyl phthalate (DIBP) | DIBP | 84-69-5 |
| Dicyclohexyl phthalate (DCHP) | DCHP | 84-61-7 |
| Di-isotridecyl phthalate | | 27253-26-5 |
| Di-C16-18 alkyl phthalate | | 90193-76-3 |
| Benzyl 3-isobutyryloxy-1-isopropyl-2,2-dimethylpropyl phthalate | | 16883-83-3 |
| Benzyl C7-9-branched and linear alkyl phthalate | | 68515-40-2 |
| bis(2-ethylhexyl) phthalate (DEHP) | DEHP | 117-81-7 |

Orthophthalates are broadly divided into two groups; high molecular weight orthophthalates and low molecular weight orthophthalates.

High Molecular Weight Orthophthalates

High molecular weight (HMW) or high orthophthalates include those with 7-13 carbon atoms, which gives them increased permanency and durability. The most common types of high orthophthalates include DINP, DIDP, DPHP, DIUP, and DTDP.

Low Molecular Weight Orthophthalates

Low molecular weight (LMW) or low orthophthalates are those with 3-6 carbon atoms in their backbone. The most common low orthophthalates include DEHP, DBP, DIBP and BBP. DEHP is the most commonly used plasticizer in medical devices. However, DHEP and other LMW orthophthalates have been shown to be toxic and carcinogenic in animal studies. Because DEHP migrates in PVC, it can leach out into fluids, including into body fluids from implanted medical devices, or from external medical devices which contact fluids directed into the body.

The blended compositions of the invention can include any of the plasticizers described herein.

PVC Compositions for Medical Devices

Approximately 25% of all plastic medical products are made from PVC. Plasticized PVC can be compounded in a variety of formulations to meet end-product specifications and often has good clarity, such that tubes and other products retain their transparency to allow for continual monitoring of fluid levels and flow. Moreover, PVC can be manufactured in a range of flexibilities and can be used in a wide range of temperatures, and it retains its flexibility, strength, and durability at low temperatures. PVC formulations exhibit excellent strength and toughness, and PVC exhibits good water and chemical resistance and stability, which helps maintain sterility. Plasticized PVC in particular maintains its product integrity under various sterilization environments like steam, radiation, and ethylene oxide. PVC can easily be extruded, thermoformed, blow bolding, and injection molded, to form various medical device components, parts, and packaging. PVC medical devices are fabricated from PVC base polymer and additives to achieve properties desired in the final article.

Plasticized PVC may be characterized by its hardness, for example, by its durometer, also referred to as its shore hardness. There are several scales of durometer, the two most common scales are the ASTM D2240 type A and type D scales. The A scale is for softer plastics, while the D scale is used for harder ones. Each scale results in values between 0 and 100, with higher values indicating a harder material. Durometer measures the depth of an indentation in the material on a given force on a standardized presser foot. This depth is dependent on the hardness of the material, its viscoelastic properties, the shape of the indenting foot, and the duration of the test. The basic test requires applying the force in a consistent manner, without shock, and measuring the depth of indentation. For example, the ASTM D2240 type A scale employs and intenting foot configuration of a 1.1 mm hardened steel rod having a 1.4 mm diameter, with a truncated 35° cone having a 0.79 mm diameter. The applied mass is 0.822 kg and the resulting force is 8.064 N. The type D scale employs and intenting foot configuration of a 1.1 mm hardened steel rod having a 1.4 mm diameter, with a 30° conical point and a 0.1 mm radius tip. The applied mass is 4.550 kg and the resulting force is 44.64 N. For each scale, the depth of indentation is measured after the indenter has been applied on the material for 15 seconds. If the indenter penetrates 2.54 mm (0.100 inch) or more into the material, the durometer, or shore hardness, is 0 for that scale. If it does not penetrate at all, then the shore hardness is 100 for that scale. PVC compositions used in medical devices generally have a shore hardness of type A or type D.

Tables 3 and 4 summarize the typical medical device applications of various types of extrusion and molding grades of PVC, respectively. The blended compositions of the invention can have any of the Shore hardness values described herein.

TABLE 3

Typical applications of PVC Medical Extrusion Compounds

| Shore A Hardness 23° C. | Typical Applications |
|---|---|
| 30/40/50/60 | Soft tubing |
| 65 | Heart/lung bypass tubing |
| 70 | Peristatis pumping tubing |
| 50/60/70 | Medium soft tubing |
| 75 | Blood tubing |
| 80 | endotracheal tubing, catheters, blood bags |
| 80/85 | Medium stiff tubing |
| 97 | Drip chamber components |
| 99 | Post-formable stiff catheter tubing |

TABLE 4

Typical applications of PVC Medical Molding Compounds

| Shore A Hardness 23° C. | Typical Applications |
|---|---|
| 15/35/45 | Soft molding applications |
| 45/55/65 | Face masks |
| 70 | Catheter funnels, enema nozzles |
| 75 | Blood transfusion and dialysis components |
| 80 | Blood transfusion set components |
| 90 | Drip chamber components |
| 95 | Drip chamber components, end caps, luer fittings |

A desired hardness in a given PVC formulation can be achieved by selecting an appropriate amount of plasticizer. Shore A hardness is inversely correlated with plasticizer loading. For example, for a given PVC resin, DEHP loading of about 10 to about 40 parts per hundred (PPH) produces shore A hardness values of between about 99 and 97. DEHP loading of about 40 PPH to about 50 PPH dramatically decreases shore A hardness from between about 97 to about 83. DEHP loading of about 50 to about 70 PPH correlates to shore A hardness values of about 83 to about 73, and DHP loading of about 80 PPH produces a shore A hardness of about 71.

Plasticizers may be about 0.01 wt % to about 80 wt % of a given formulation, 10 wt % to about 50 wt %, and in typical formulations are about 20 wt % to about 45 wt % plasticizer.

Surface Modifying Macromolecules (SMMs)

The SMMs used in the PVC admixture to form the plasticized resins of the invention may be described by the structure of any one of formulae (I), (II), (III), (IV), (V), (VI), (VII), (VIII), (IX), (X), (XI), (XII), (XIII), (XIV), (XV), (XVI), and (XVII) shown below.

(1) Formula (I):

　　　　　　　　　　　　　　　(I)

where
(i) A includes hydrogenated polybutadiene, poly((2,2-dimethyl)-1,3-propylene carbonate), polybutadiene, poly(diethylene glycol)adipate, poly(hexamethylene carbonate), poly(ethylene-co-butylene), (neopentyl glycol-ortho phthalic anhydride) polyester, (diethylene glycol-ortho phthalic anhydride) polyester, (1,6-hexanediol-ortho phthalic anhydride) polyester, or bisphenol A ethoxylate;
(ii) B is a segment including a urethane; and
(iii) $F_T$ is a polyfluoroorgano group, and
(iv) n is an integer from 1 to 10.
(2) Formula (II):

$$F_T-[B-A]_n-B-F_T \quad (II)$$

where
(i) B includes a urethane;
(ii) A includes polypropylene oxide, polyethylene oxide, or polytetramethylene oxide;
(iii) $F_T$ is a polyfluoroorgano group; and
(iv) n is an integer from 1 to 10.
(3) Formula (III) or Formula (IV):

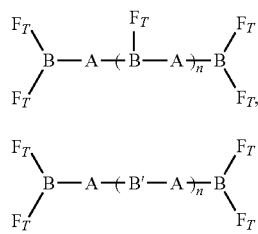

(III)

(IV)

where
(i) A is an oligomeric segment containing an ether linkage, an ester linkage, a carbonate linkage, or a polyalkylene and having a theoretical molecular weight of from 500 to 3,500 Daltons (e.g., from 500 to 2,000 Daltons, from 1,000 to 2,000 Daltons, or from 1,000 to 3,000 Daltons);
(ii) B is a segment including a isocyanurate trimer or biuret trimer; B', when present, is a segment including a urethane;
(iii) each $F_T$ is a polyfluoroorgano group; and
(iv) n is an integer between 0 to 10.
(4) Formula (V):

$$F_T-[B-A]_n-B-F_T \quad (V)$$

where
(i) A is an oligomeric segment including polypropylene oxide, polyethylene oxide, or polytetramethylene oxide and having a theoretical molecular weight of from 500 to 3,000 Daltons (e.g., from 500 to 2,000 Daltons, from 1,000 to 2,000 Daltons, or from 1,000 to 3,000 Daltons);
(ii) B is a segment formed from a diisocyanate;
(iii) $F_T$ is a polyfluoroorgano group; and
(iv) n is an integer from 1 to 10.
(5) Formula (VI):

(VI)

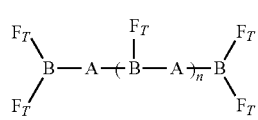

where
(i) A is an oligomeric segment including polyethylene oxide, polypropylene oxide, polytetramethylene oxide, or a mixture thereof, and having a theoretical molecular weight of from 500 to 3,000 Daltons (e.g., from 500 to 2,000 Daltons, from 1,000 to 2,000 Daltons, or from 1,000 to 3,000 Daltons);
(ii) B is a segment including an isocyanurate trimer or biuret trimer;
(iii) $F_T$ is a polyfluoroorgano group; and
(iv) n is an integer from 0 to 10.
(6) Formula (VII):

$$F_T-[B-A]_n-B-F_T \quad (VII)$$

where
(i) A is a polycarbonate polyol having a theoretical molecular weight of from 500 to 3,000 Daltons (e.g., from 500 to 2,000 Daltons, from 1,000 to 2,000 Daltons, or from 1,000 to 3,000 Daltons);
(ii) B is a segment formed from a diisocyanate;
(iii) $F_T$ is a polyfluoroorgano group; and
(iv) n is an integer from 1 to 10.

(VIII)

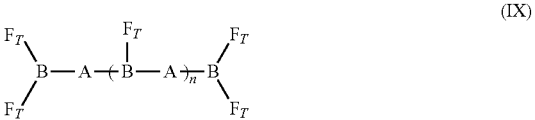

(7) Formula (VIII):
where
(i) A is an oligomeric segment including a polycarbonate polyol having a theoretical molecular weight of from 500 to 3,000 Daltons (e.g., from 500 to 2,000 Daltons, from 1,000 to 2,000 Daltons, or from 1,000 to 3,000 Daltons);
(ii) B is a segment including an isocyanurate trimer or biuret trimer;
(iii) $F_T$ is a polyfluoroorgano group; and
(iv) n is an integer from 0 to 10.
(8) Formula (IX):

(IX)

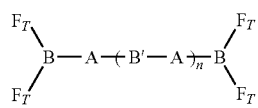

where
(i) A includes a first block segment selected from polypropylene oxide, polyethylene oxide, polytetramethylene oxide, or a mixture thereof, and a second block segment including a polysiloxane or polydimethylsiloxane, where A has a theoretical molecular weight of from 1,000 to 5,000 Daltons (e.g., from 1,000 to 3,000 Daltons, from 2,000 to 5,000 Daltons, or from 2,500 to 5,000 Daltons);
(ii) B is a segment including an isocyanurate trimer or biuret trimer;
(iii) $F_T$ is a polyfluoroorgano group; and
(iv) n is an integer from 0 to 10.
(9) Formula (X):

$$F_T-[B-A]_n-B-F_T \quad (X)$$

where
(i) A is a segment selected from the group consisting of hydrogenated polybutadiene (e.g., HLBH), polybutadiene (e.g., LBHP), hydrogenated polyisoprene (e.g., HHTPI), polysiloxane-polyethylene glycol block copolymer, and polystyrene and has a theoretical molecular weight of from 750 to 3,500 Daltons (e.g., from 750 to 2,000 Daltons, from 1,000 to 2,500 Daltons, or from 1,000 to 3,500 Daltons);
(ii) B is a segment formed from a diisocyanate;
(iii) $F_T$ is a polyfluoroorgano group; and
(iv) n is an integer from 1 to 10.
(10) Formula (XI):

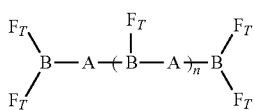
(XI)

where
(i) A is hydrogenated polybutadiene (e.g., HLBH), polybutadiene (e.g., LBHP), hydrogenated polyisoprene (e.g., HHTPI), or polystyrene and has a theoretical molecular weight of from 750 to 3,500 Daltons (e.g., from 750 to 2,000 Daltons, from 1,000 to 2,500 Daltons, or from 1,000 to 3,500 Daltons);
(ii) B is a segment including an isocyanurate trimer or biuret trimer;
(iii) $F_T$ is a polyfluoroorgano group; and
(iv) n is an integer from 0 to 10.
(11) Formula (XII):

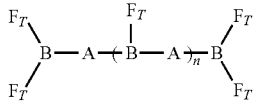
(XII)

where
(i) A is a polyester having a theoretical molecular weight of from 500 to 3,500 Daltons (e.g., from 500 to 2,000 Daltons, from 1,000 to 2,000 Daltons, or from 1,000 to 3,000 Daltons);
(ii) B is a segment including an isocyanurate trimer or biuret trimer;
(iii) $F_T$ is a polyfluoroorgano group; and
(iv) n is an integer from 0 to 10.
(12) Formula (XIII):

 (XIII)

where $F_T$ is a polyfluoroorgano group and A is an oligomeric segment.
(13) Formula (XIV):

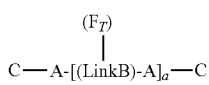
(XIV)

where
(i) $F_T$ is a polyfluoroorgano group covalently attached to LinkB;
(ii) C is a chain terminating group;
(iii) A is an oligomeric segment;
(iv) LinkB is a coupling segment; and
(v) a is an integer greater than 0.
(14) Formula (XV):

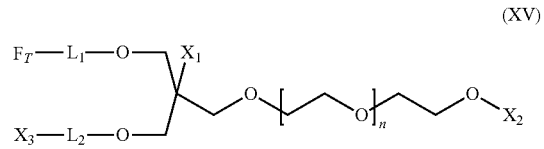
(XV)

where
(i) each $F_T$ is independently a surface-active group selected from polydimethylsiloxanes, hydrocarbons, and polyfluoroorgano groups, and combinations thereof (e.g., each $F_T$ is independently a polyfluoroorgano);
(ii) $X_1$ is H, $CH_3$, or $CH_2CH_3$;
(iii) each of $X_2$ and $X_3$ is independently H, $CH_3$, $CH_2CH_3$, or $F_T$;
(iv) each of $L_1$ and $L_2$ is independently a bond, an oligomeric linker, or a linker with two terminal carbonyls; and
(v) n is an integer from 5 to 50.
(15) Formula (XVI):

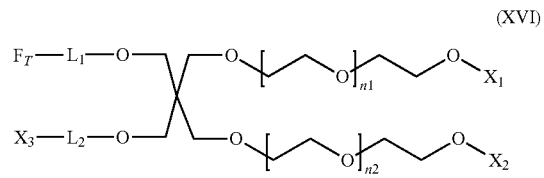
(XVI)

where
(i) each $F_T$ is independently a surface-active group (e.g., a polyfluoroorgano);
(ii) each of $X_1$, $X_2$, and $X_3$ is independently H, $CH_3$, $CH_2CH_3$, or $F_T$;
(iii) each of $L_1$ and $L_2$ is independently a bond, an oligomeric linker, a linker with two terminal carbonyls, or is formed from a diisocyanate; and
(iv) each of n1 and n2 is independently an integer from 5 to 50.
(16) Formula (XVII):

$G\text{-}A_m\text{-}[B\text{-}A]_n\text{-}B\text{-}G$ (XVII)

where
(i) each A comprises hydrogenated polybutadiene, poly ((2,2-dimethyl)-1,3-propylene carbonate), polybutadiene, poly (diethylene glycol)adipate, poly (hexamethylene carbonate), poly (ethylene-co-butylene), (diethylene glycol-ortho phthalic anhydride) polyester, (1,6-hexanediol-ortho phthalic anhydride) polyester, (neopentyl glycol-ortho phthalic anhydride) polyester, a polysiloxane, or bisphenol A ethoxylate;
(ii) each B is independently a bond, an oligomeric linker, or a linker with two terminal carbonyls;
(iii) each G is H or a polyfluoorgrano, provided that at least one G is a polyfluoroorgano;
(iv) n is an integer from 1 to 10; and
(v) m is 0 or 1.

The SMM of formula (I) can include B formed from a diisocyanate (e.g., 3-isocyanatomethyl-3,5,5-trimethyl-cyclohexyl isocyanate; 4,4'-methylene bis(cyclohexyl isocyanate); 4,4'-methylene bis(phenyl isocyanate); toluene-2,4-diisocyanate; m-tetramethylxylene diisocyanate; or hexamethylene diisocyanate). The variable n may be 1 or 2. The PVC admixtures of the invention may include a plasticized PVC base polymer and the SMM of formula (I).

The SMM of formulae (III) and (IV) can include A that is an oligomeric segment containing hydrogenated polybutadiene (HLBH), poly((2,2-dimethyl)-1,3-propylene carbonate) (PCN), polybutadiene (LBHP), polytetramethylene oxide (PTMO), polypropylene oxide (PPO), (diethyleneglycol-orthophthalic anhydride) polyester (PDP), hydrogenated polyisoprene (HHTPI), poly(hexamethylene carbonate), poly((2-butyl-2-ethyl)-1,3-propylene carbonate), or hydroxylterminated polydimethylsiloxane (C22). In the SMM of formulae (III) and (IV), B is formed by reacting a triisocyanate (e.g., hexamethylene diisocyanate (HDI) biuret trimer, isophorone diisocyanate (IPDI) trimer, or hexamethylene diisocyanate (HDI) trimer) with a diol including the oligomeric segment A. The PVC admixtures of the invention may include a plasticized PVC base polymer and the SMM of formula (III). The PVC admixtures of the invention may include a plasticized PVC base polymer and the SMM of formula (IV).

In the SMM of formula (V), B may be a segment formed from 3-isocyanatomethyl-3,5,5-trimethyl-cyclohexyl isocyanate; 4,4'-methylene bis(cyclohexyl isocyanate); 4,4'-methylene bis(phenyl isocyanate); toluene-2,4-diisocyanate; m-tetramethylxylene diisocyanate; and hexamethylene diisocyanate. In the SMM of formula (V), segment A can be poly(ethylene oxide)-b-poly(propylene oxide)-b-poly(ethylene oxide). The variable n may be an integer from 1 to 3. The PVC admixtures of the invention may include a plasticized PVC base polymer and the SMM of formula (V).

In the SMM of formula (VI), B is a segment formed by reacting a triisocyanate with a diol of A. The triisocyanate may be hexamethylene diisocyanate (HDI) biuret trimer, isophorone diisocyanate (IPDI) trimer, or hexamethylene diisocyanate (HDI) trimer. In the SMM of formula (VI), segment A can be poly(ethylene oxide)-b-poly(propylene oxide)-b-poly(ethylene oxide). The variable n may be 0, 1, 2, or 3. The PVC admixtures of the invention may include a plasticized PVC base polymer and the SMM of formula (VI).

In the SMM of formula (VII), Oligo can include poly((2,2-dimethyl)-1,3-propylene carbonate) (PCN). B may be a segment formed from 3-isocyanatomethyl-3,5,5-trimethyl-cyclohexylisocyanate; 4,4'-methylene bis(cyclohexyl isocyanate); 4,4'-methylene bis(phenyl isocyanate); toluene-2,4-diisocyanate; m-tetramethylxylene diisocyanate; and hexamethylene diisocyanate. The variable n may be 1, 2, or 3. The PVC admixtures of the invention may include a plasticized PVC base polymer and the SMM of formula (VII).

In the SMM of formula (VIII), B is a segment formed by reacting a triisocyanate with a diol of A (e.g., the oligomeric segment). The triisocyanate may be hexamethylene diisocyanate (HDI) biuret trimer, isophorone diisocyanate (IPDI) trimer, or hexamethylene diisocyanate (HDI) trimer. The segment A can include poly((2,2-dimethyl)-1,3-propylene carbonate) (PCN) or poly(hexamethylene carbonate) (PHCN). The variable n may be 0, 1, 2, or 3. The PVC admixtures of the invention may include a plasticized PVC base polymer and the SMM of formula (VIII).

In the SMM of formula (IX), B is a segment formed by reacting a triisocyanate with a diol of A. In segment A, the number of first block segments and second block segments can be any integer or non-integer to provide the approximate theoretical molecule weight of the segment. The segment A can include polypropylene oxide and polydimethylsiloxane. The triisocyanate may be hexamethylene diisocyanate (HDI) biuret trimer, isophorone diisocyanate (IPDI) trimer, or hexamethylene diisocyanate (HDI) trimer. The variable n may be 0, 1, 2, or 3. The PVC admixtures of the invention may include a plasticized PVC base polymer and the SMM of formula (IX).

In SMM of formula (X), B is a segment formed from a diisocyanate. The segment A can include hydrogenated polybutadiene. Alternatively, the segment A can include polysiloxane-polyethylene glycol block copolymer (e.g., PEG-PDMS-PEG). The segment B may be formed from 3-isocyanatomethyl-3,5,5-trimethy-cyclohexyl isocyanate; 4,4'-methylene bis(cyclohexyl isocyanate); 4,4'-methylene bis(phenyl isocyanate); toluene-2,4-diisocyanate; m-tetramethylxylene diisocyanate; and hexamethylene diisocyanate. The variable n may be 1, 2, or 3. The PVC admixtures of the invention may include a plasticized PVC base polymer and the SMM of formula (X).

In the SMM of formula (XI), B is a segment formed by reacting a triisocyanate with a diol of A. The segment A may be hydrogenated polybutadiene (HLBH) or hydrogenated polyisoprene (HHTPI). The triisocyanate may be hexamethylene diisocyanate (HDI) biuret trimer, isophorone diisocyanate (IPDI) trimer, or hexamethylene diisocyanate (HDI) trimer. The variable n may be 0, 1, 2, or 3. The PVC admixtures of the invention may include a plasticized PVC base polymer and the SMM of formula (XI).

In the SMM of formula (XII), B is a segment formed by reacting a triisocyanate with a diol of A (e.g., polyester). The segment A may be poly(diethylene glycol)adipate, (neopentyl glycol-ortho phthalic anhydride) polyester, (diethylene glycol-ortho phthalic) anhydride polyester, or (1,6-hexanediol-ortho phthalic anhydride) polyester. The triisocyanate may be hexamethylene diisocyanate (HDI) biuret trimer, isophorone diisocyanate (IPDI) trimer, and hexamethylene diisocyanate (HDI) trimer. The variable n may be 0, 1, 2, or 3. The PVC admixtures of the invention may include a plasticized PVC base polymer and the SMM of formula (XII).

The SMM of formula (XIII) can include a segment A that is a branched or non-branched oligomeric segment of fewer than 20 repeating units (e.g., from 2 to 15 units, from 2 to 10 units, from 3 to 15 units, and from 3 to 10 units). In certain embodiments, the SMM of formula (XIII) include an oligomeric segment selected from polyurethane, polyurea, polyamide, polyalkylene oxide, polycarbonate, polyester, polylactone, polysilicone, polyethersulfone, polyolefin, polyvinyl derivative, polypeptide, polysaccharide, polysiloxane, polydimethylsiloxane, polyethylene-butylene, polyisobutylene, polybutadiene, polypropylene oxide, polyethylene oxide, polytetramethylene oxide, or polyethylenebutylene segments. The PVC admixtures of the invention may include a plasticized PVC base polymer and the SMM of formula (XIII).

The SMM of formula (XIV) can include a segment A that is a branched or non-branched oligomeric segment of fewer than 20 repeating units (e.g., from 2 to 15 units, from 2 to 10 units, from 3 to 15 units, and from 3 to 10 units). In certain embodiments, the SMM of formula (XIV) include an oligomeric segment selected from polyurethane, polyurea, polyamide, polyalkylene oxide, polycarbonate, polyester, polylactone, polysilicone, polyethersulfone, polyolefin, polyvinyl derivative, polypeptide, polysaccharide, polysiloxane, polydimethylsiloxane, polyethylene-butylene, polyisobutylene, polybutadiene, polypropylene oxide, polyethylene oxide, or polytetramethylene oxide. The PVC admixtures of the invention may include a plasticized PVC base polymer and the SMM of formula (XIV).

The SMM of formula (XV) can include a segment $L_1$ that is an oligomeric linker (e.g., of fewer than 50 repeating units (e.g., from 2 to 40 units, from 2 to 30 units, from 3 to 20 units, or from 3 to 10 units)). In some embodiments of formula (XV), $L_2$ is an oligomeric linker (e.g., of fewer than 50 repeating units (e.g., from 2 to 40 units, from 2 to 30 units, from 3 to 20 units, or from 3 to 10 units)). In particular embodiments of formula (XV), each of $L_1$ and $L_2$ is a bond. In certain embodiments of formula (XV), the SMM includes an oligomeric segment (e.g., in any one of $L_1$ and $L_2$) selected from the group consisting of polyurethane, polyurea, polyamide, polyalkylene oxide (e.g., polypropylene oxide, polyethylene oxide, or polytetramethylene oxide), polyester, polylactone, polysilicone, polyethersulfone, polyolefin, polyvinyl derivative, polypeptide, polysaccharide, polysiloxane, polydimethylsiloxane, poly(ethylene-co-butylene), polyisobutylene, and polybutadiene. In some embodiments of formula (XV), the SMM is a compound of formula (XV-A):

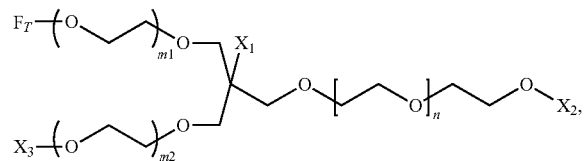

(XV-A)

where each of m1 and m2 is independently an integer from 0 to 50. In particular embodiments of formula (XV-A), m1 is 5, 6, 7, 8, 9, or 10 (e.g., m1 is 6). In some embodiments of formula (XV-A), m2 is 5, 6, 7, 8, 9, or 10 (e.g., m2 is 6).

In certain embodiments of formula (XV) or (XV-A), $X_2$ is $F_T$. In other embodiments, $X_2$ is $CH_3$ or $CH_2CH_3$. In particular embodiments of formula (XV) or (XV-A), $X_3$ is $F_T$. In other embodiments, each $F_T$ is independently a polyfluoroorgano (e.g., a polyfluoroacyl, such as $-(O)_q-[C(=O)]_r(CH_2)_o(CF_2)_pCF_3$, in which q is 0, r is 1; o is from 0 to 2; and p is from 0 to 10). In certain embodiments of formula (XV) or (XV-A), n is an integer from 5 to 40 (e.g., from 5 to 20, such as from 5, 6, 7, 8, 9, or 10). In some embodiments of formula (XV) or (XV-A), each $F_T$ includes $(CF_2)_5CF_3$. The PVC admixtures of the invention may include a plasticized PVC base polymer and the SMM of formula (XV). The PVC admixtures of the invention may include a plasticized PVC base polymer and the SMM of formula (XV-A).

The SMM of formula (XVI) can include a segment $L_1$ that is an oligomeric linker (e.g., of fewer than 50 repeating units (e.g., from 2 to 40 units, from 2 to 30 units, from 3 to 20 units, or from 3 to 10 units)). In some embodiments of formula (XVI), $L_2$ is an oligomeric linker (e.g., of fewer than 50 repeating units (e.g., from 2 to 40 units, from 2 to 30 units, from 3 to 20 units, or from 3 to 10 units)). In particular embodiments of formula (XVI), each of $L_1$ and $L_2$ is a bond. In certain embodiments of formula (XVI), the SMM includes an oligomeric segment (e.g., in any one of $L_1$ and $L_2$) selected from polyurethane, polyurea, polyamide, polyalkylene oxide (e.g., polypropylene oxide, polyethylene oxide, or polytetramethylene oxide), polyester, polylactone, polysilicone, polyethersulfone, polyolefin, polyvinyl derivative, polypeptide, polysaccharide, polysiloxane, polydimethylsiloxane, poly(ethylene-co-butylene), polyisobutylene, or polybutadiene. In some embodiments of formula (XVI), the SMM is a compound of formula (XVI-A):

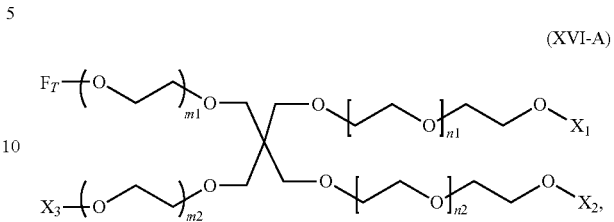

(XVI-A)

where each of m1 and m2 is independently an integer from 0 to 50. In particular embodiments of formula (XV-A), m1 is 5, 6, 7, 8, 9, or 10 (e.g., m1 is 6). In some embodiments of formula (XV-A), m2 is 5, 6, 7, 8, 9, or 10 (e.g., m2 is 6).

In certain embodiments of formula (XVI) or (XVI-A), $X_2$ is $F_T$. In other embodiments of formula (XVI) or (XVI-A), $X_2$ is $CH_3$ or $CH_2CH_3$. In particular embodiments of formula (XVI) or (XVI-A), $X_3$ is $F_T$. In other embodiments of formula (XVI) or (XVI-A), each $F_T$ is independently a polyfluoroorgano (e.g., a polyfluoroacyl, such as $-(O)_q-[C(=O)]_r(CH_2)_o(CF_2)_pCF_3$, in which q is 0, r is 1; o is from 0 to 2; and p is from 0 to 10). In some embodiments of formula (XVI) or (XVI-A), each $F_T$ includes $(CF_2)_5CF_3$. The PVC admixtures of the invention may include a plasticized PVC base polymer and the SMM of formula (XVI). The PVC admixtures of the invention may include a plasticized PVC base polymer and the SMM of formula (XVI-A).

In some embodiments of formula (XVII), m is 1. The SMM of formula (XVII) can be a compound of formula (XVII-A):

G-A-[B-A]$_n$-G     (XVII-A).

In other embodiments of formula (XVII), m is 0. The SMM of formula (XVII) can be a compound of formula (XVII-B):

G-[B-A]$_n$-B-G     (XVII-B).

In particular embodiments of formula (XVII), (XVII-A), or (XVII-B), each B is a linker with two terminal carbonyls. In certain embodiments of formula (XVII), (XVII-A), or (XVII-B), each B is a bond. In some embodiments of Formula (XVII), (XVII-A), or (XVII-B), the bond connecting G and B is an oxycarbonyl bond (e.g., an oxycarbonyl bond in an ester). In other embodiments of formula (XVII), (XVII-A), or (XVII-B), n is 1 or 2.

The SMM of formula (XVII) can be a compound of formula (XVII-C):

G-A-G     (XVII-C).

In formula (XVII), (XVII-A), (XVII-B), or (XVII-C), G can be a polyfluoroorgano group (e.g., a polyfluoroalkyl). In some embodiments of formula (XVII), (XVII-A), (XVII-B), or (XVII-C), G is $F_T$ (e.g., each $F_T$ is independently a polyfluoroorgano (e.g., a polyfluoroacyl, such as $-(O)_q-[C(=O)]_r(CH_2)_o(CF_2)_pCF_3$, in which q is 0, r is 1; o is from 0 to 2; and p is from 0 to 10). In some embodiments of formula (XVII), (XVII-A), (XVII-B), or (XVII-C), each $F_T$ includes $(CF_2)_5CF_3$. The PVC admixtures of the invention may include a plasticized PVC base polymer and the SMM of formula (XVII). The PVC admixtures of the invention may include a plasticized PVC base polymer and the SMM of formula (XVII-A). The PVC admixtures of the invention may include a plasticized PVC base polymer and the SMM of formula (XVII-B). The PVC admixtures of the invention may include a plasticized PVC base polymer and the SMM of formula (XVII-C).

For any of the SMMs of the invention formed from a diisocyanate, the diisocyanate may be 3-isocyanatomethyl-3,5,5-trimethyl-cyclohexylisocyanate; 4,4'-methylene bis(cyclohexyl isocyanate) (HMDI); 2,2'-, 2,4'-, and 4,4'-methylene bis(phenyl isocyanate) (MDI); toluene-2,4-diisocyanate; aromatic aliphatic isocyanate, such 1,2-, 1,3-, and 1,4-xylene diisocyanate; meta-tetramethylxylene diisocyanate (m-TMXDI); para-tetramethylxylene diisocyanate (p-TMXDI); hexamethylene diisocyanate (HDI); ethylene diisocyanate; propylene-1,2-diisocyanate; tetramethylene diisocyanate; tetramethylene-1,4-diisocyanate; octamethylene diisocyanate; decamethylene diisocyanate; 2,2,4-trimethylhexamethylene diisocyanate; 2,4,4-trimethylhexamethylene diisocyanate; dodecane-1,12-diisocyanate; dicyclohexylmethane diisocyanate; cyclobutane-1,3-diisocyanate; cyclohexane-1,2-diisocyanate; cyclohexane-1,3-diisocyanate; cyclohexane-1,4-diisocyanate; methyl-cyclohexylene diisocyanate (HTDI); 2,4-dimethylcyclohexane diisocyanate; 2,6-dimethylcyclohexane diisocyanate; 4,4'-dicyclohexyl diisocyanate; 2,4'-dicyclohexyl diisocyanate; 1,3,5-cyclohexane triisocyanate; isocyanatomethylcyclohexane isocyanate; 1-isocyanato-3,3,5-trimethyl-5-isocyanatomethylcyclohexane; isocyanatoethylcyclohexane isocyanate; bis(isocyanatomethyl)-cyclohexane; 4,4'-bis(isocyanatomethyl) dicyclohexane; 2,4'-bis(isocyanatomethyl) dicyclohexane; isophoronediisocyanate (IPDI); 2,4-hexahydrotoluene diisocyanate; 2,6-hexahydrotoluene diisocyanate; 3,3'-dimethyl-4,4'-biphenylene diisocyanate (TODI); polymeric MDI; carbodiimide-modified liquid 4,4'-diphenylmethane diisocyanate; para-phenylene diisocyanate (PPDI); meta-phenylene diisocyanate (MPDI); naphthylene-1,5-diisocyanate; 2,4'-, 4,4'-, or 2,2'-biphenyl diisocyanate; polyphenyl polymethylene polyisocyanate (PMDI); mixtures of MDI and PMDI; mixtures of PMDI and TDI; dimerized uretdione of any isocyanate described herein, such as uretdione of toluene diisocyanate, uretdione of hexamethylene diisocyanate, or a mixture thereof; or a substituted or isomeric mixture thereof.

For any of the SMMs of the invention formed from an isocyanate trimer, the isocyanate trimer can be hexamethylene diisocyanate (HDI) biuret or trimer, isophorone diisocyanate (IPDI) trimer, hexamethylene diisocyanate (HDI) trimer; 2,2,4-trimethyl-1,6-hexane diisocyanate (TMDI) trimer; a trimerized isocyanurate of any isocyanates described herein, such as isocyanurate of toluene diisocyanate, trimer of diphenylmethane diisocyanate, trimer of tetramethylxylene diisocyanate, or a mixture thereof; a trimerized biuret of any isocyanates described herein; modified isocyanates derived from the above diisocyanates; or a substituted or isomeric mixture thereof.

The SMM can include the group $F_T$ that is a polyfluoroorgano group having a theoretical molecular weight of from 100 Da to 1,500 Da. For example, $F_T$ may be $CF_3(CF_2)_r(CH_2CH_2)_p$— wherein p is 0 or 1, r is 2-20, and $CF_3(CF_2)_s(CH_2CH_2O)_X$, where X is from 0 to 10 and s is from 1 to 20. Alternatively, $F_T$ may be $CH_mF_{(3-m)}(CF_2)_rCH_2CH_2$— or $CH_mF_{(3-m)}(CF_2)_s(CH_2CH_2O)_X$—, where m is 0, 1, 2, or 3; X is an integer from 0 to 10; r is an integer from 2 to 20; and s is an integer from 1 to 20. In certain embodiments, $F_T$ is 1H,1H,2H,2H-perfluoro-1-decanol; 1H,1H,2H,2H-perfluoro-1-octanol; 1H,1H,5H-perfluoro-1-pentanol; or 1H,1H-perfluoro-1-butanol, or a mixture thereof. In particular embodiments, $F_T$ is $(CF_3)(CF_2)_5CH_2CH_2O$—, $(CF_3)(CF_2)_7CH_2CH_2O$—, $(CF_3)(CF_2)_5CH_2CH_2O$—, $F_2(CF_2)_3CH_2O$—, $(CF_3)(CF_2)_2CH_2O$—, or $(CF_3)(CF_2)_5$—. In still other embodiments the polyfluoroalkyl group is $(CF_3)(CF_2)_5$—, e.g., where the polyfluoroalkyl group is bonded to a carbonyl of an ester group. In certain embodiments, polyfluoroorgano is $-(O)_q-[C(=O)]_r(CH_2)O(CF_2)_pCF_3$, in which q is 0 and r is 1, or q is 1 and r is 0; o is from 0 to 2; and p is from 0 to 10.

In some embodiments, the SMM is a structure described by any one of formulae (I)-(XVII). In certain embodiments, the SMM is any one of compounds 1-40. The theoretical structures of compounds 1-40 are illustrated in FIGS. 1-30.

The surface-modifying macromolecules can be prepared according to methods described herein or in U.S. Pat. Nos. 6,127,507; 8,071,683; and 8,318,867; and in U.S. pre-grant publication Nos. 2008/0228253 and 2012/0148774; the preparation procedures for surface-modifying macromolecules disclosed therein are incorporated herein in their entirety.

The following examples are meant to illustrate the invention. They are not meant to limit the invention in any way.

EXAMPLES

Surface-modifying macromolecules of any one of formulae (I), (II), (III), (IV), (V), (VI), (VII), (VIII), (IX), (X), (XI), (XII), (XIII), and (XIV) can be prepared as described in U.S. Pat. Nos. 6,127,507; 8,071,683; and 8,318,867; and in U.S. pre-grant publication Nos. 2008/0228253 and 2012/0148774. Preparation of the surface-modifying macromolecules of formula (XV), (XVI), and (XVII) is described below. FIGS. 1-27 show exemplary surface-modifying macromolecules that were prepared in accordance with procedures described herein or in U.S. Pat. Nos. 6,127,507; 8,071,683; and 8,318,867; and in U.S. pre-grant publication Nos. 2008/0228253 and 2012/0148774.

Example 1. Preparation of SMMs

The SMMs used in the admixtures of the invention can be prepared using methods known in the art from the appropriately selected reagents, such as diisocyanates/triisocyanates, dicarboxylic acids, diols, and fluorinated alcohols to form a wide range of SMMs. The reagents include but are not limited to the component reagents mentioned below.

Diisocyanates
    HMDI=4,4'-methylene bis(cyclohexyl isocyanate)
    IPDI=Isophorone Diisocyanate
    TMXDI=m-tetramethylenexylene diisocyanate
    HDI=Hexamethylene Diisocyanate Triisocyanates
    Desmodur N3200 or Desmodur N-3200=hexamethylene diisocyanate (HDI) biuret trimer
    Desmodur Z4470A or Desmodur Z-4470A=isophorone diisocyanate (IPDI) trimer
    Desmodur N3300=hexamethylene diisocyanate (HDI) trimer Diols/Polyols
    HLBH=Hydrogenated-hydroxyl terminated polybutadiene,
    PCN=Poly(2,2-dimethyl-1-3-propylenecarbonate) diol
    PHCN=Poly(hexamethylene carbonate)diol
    PEB=Poly(Ethylene-co-Butylene)diol
    LBHP=Hydroxyl terminated polybutadiene polyol
    PEGA=Poly(diethylene glycol)adipate
    PTMO=Poly(tetramethylene oxide) diol
    PDP=Diethylene Glycol-Ortho phthalic Anhydride polyester polyol HHTPI=hydrogenated hydroxyl terminated polyisoprene C22=hydroxylterminated polydimethylsiloxanes block copolymer C25 (Diol)=Hydroxy Terminated Polidimethylsiloxane (Ethylene Oxide-PDMS-Ethylene Oxide) block copolymer C10 (Diol)=Hydroxy Terminated Polidimethylsiloxane (Ethylene Oxide-PDMS-Ethylene Oxide) block copolymer PLN=Poly(ethylene glycol)-block-poly(propylene glycol))-block-poly(ethylene glycol) polymer (PEO-PPO-PEO Pluronic polymers)

PLN8K=Poly(ethylene glycol)-block-poly(propylene glycol))-block-poly(ethylene glycol) polymer (PEO-PPO-PEO Pluronic polymers)

DDD=1,12-dodecanediol

SPH=1,6-hexanediol-Ortho Phthalic anhydride polyester polyol

SPN=Neopentyl glycol-Ortho Phthalic Anhydride polyester polyol

BPAE=Bisphenol A Ethoxylate diol

YMer (Diol)=Hydroxy Terminated Polyethylene glycol monomethyl ether

YMerOH (Triol)=Trimethylolpropane Ethoxylate

XMer (Tetraol)=Pentaerythritol Ethoxylate

Fluorinated End-Capping Groups

C6-FOH=$(CF_3)(CF_2)_5CH_2CH_2OH$ (1H,1H,2H,2H Perfluorooctanol)

C8-FOH=1H,1H,2H,2H Perfluorooctanol

C6-C8 FOH=$(CF_3)(CF_2)_7CH_2CH_2OH$ and $(CF_3)(CF_2)_5CH_2CH_2OH$ (Mixtures of C6-FOH and C8-FOH; also designated as BAL-D)

C10-FOH=1H,1H,2H,2H Perfluorodecanol

C8-C10 FOH=mixtures of C8-FOH and C10-FOH

C5-FOH=1H,1H,5H-perfluoro-1-pentanol

C4-FOH=1H,1H-perfluorobutanol

C3-FOH=$(CF_3)(CF_2)_2CH_2OH$ (1H,1H perfluorobutanol)

Non-Tin Based Catalyst

Bi348-Bismuth Carboxylate Type 1

Bi221-Bismuth Carboxylate Type 2

Bi601-Bismuth Carboxylate Type 3

The bismuth catalysts listed above can be purchased from King Industries (Norwalk Conn.). Any bismuth catalyst known in the art can be used to synthesize the SMMs described herein. Also, tin-based catalysts useful in the synthesis of polyurethanes may be used instead of the bismuth-based catalysts for the synthesis of the SMMs described herein.

Compound 1

Compound 1 was synthesized with PPO diol of molecular weight 1000, 1,6-hexamethylene diisocyanate (HDI), and the low boiling fraction of the fluoroalcohol (BA-L). The conditions of the synthesis were as follows: 10 grams of PPO were reacted with 3.36 grams of HDI for two hours, and then 5 grams of BA-L (low boiling fraction) were added to the reaction. The mixture was reacted with 42.5 mg of the catalyst, dibutyltin dilaurate, in 130 mL of dimethylacetamide, and the reaction temperature for the prepolymer step was maintained within 60-70° C. The polystyrene equivalent weight average molecular weight is $1.6+/-0.2\times10^4$ and its total fluorine content is 18.87+/-2.38% by weight. Thermal transitions for compound 1 are detectable by differential scanning calorimetry. Two higher order thermal transitions at approximately 14° C. and 85° C. were observed. The theoretical chemical structure of the compound 1 is shown FIG. 1A.

Compound 2

All glassware used for the synthesis was dried in an oven at 110° C. overnight. To a 3-necked 1000 mL oven dried flask equipped with a stir bar was added 175 g (72 mmol) of hydrogenated-hydroxyl terminated polybutadiene (HLBH polyol, MW=2000). The flask with the polyol was degassed overnight and then purged with dry $N_2$. A 1000 mL graduated cylinder was filled with 525 mL anhydrous Toluene, sealed by a rubber septa and purged with dry $N_2$. The toluene was transferred to the 3-necked flask via a double-edged needle and the polyol stirred vigorously to dissolve in the solvent. The flask was placed in an oil bath at 65-70° C. 39.70 g (151 mmol) of 4,4'-methylene bis(cyclohexyl isocyanate) (HMDI) was added to a degassed 250 mL flask equipped with a stir bar. To this flask was added 150 mL of anhydrous toluene from a degassed, $N_2$ purged 250 mL septa-sealed cylinder also using a double-edged needle and the mixture was stirred to dissolve the HMDI in the solvent. To a degassed 50 mL round bottom flask was added 8.75 g (5.00% w/w based on diol) of the bismuth carboxylate catalyst followed by 26 mL of toluene to dissolve the catalyst. The HMDI solution was transferred to the 1000 mL flask containing the polyol. The bismuth catalyst solution was added (20 mL) immediately following the addition of the HMDI. The reaction mixture was allowed to stir for 5 h at 70° C. to produce a HMDI-HLBH prepolymer.

In another 50 mL round bottom flask 74.95 g (180 mmol) of C8-C10 FOH (mixture of C8-FOH and C10-FOH) was added, capped with a septa, degassed and then purged with $N_2$. This was added to the 1000 mL flask containing prepolymer. All additions and transfers were conducted carefully in an atmosphere of dry $N_2$ to avoid any contact with air. The resulting mixture was heated to 45° C. for 18 hours to produce SMM (1) with the end-capped C8-C10 FOH. The SMM solution was allowed to cool to ambient temperature and formed a milky solution. The milky solution was precipitated in MeOH (methanol) and the resulting precipitate was washed repeatedly with MeOH to form a white viscous material with dough-like consistency. This viscous, semi-solid material was washed twice in THF/EDTA (Ethylene Diamine Tetraacetic Acid) to remove residual catalyst followed by two more successive washes in THF/MeOH to remove unreacted monomers, low molecular weight byproducts, and catalyst residues. The SMM was first dried in a flow oven from at 40-120° C. in a period of 10 hours gradually raising the temperature and finally dried under vacuum at 120° C. (24 hours) and stored in a desiccator as a colorless rubbery semi-solid. The theoretical chemical structure of compound 2 is shown FIG. 1B.

Compound 3

Figure 2A:
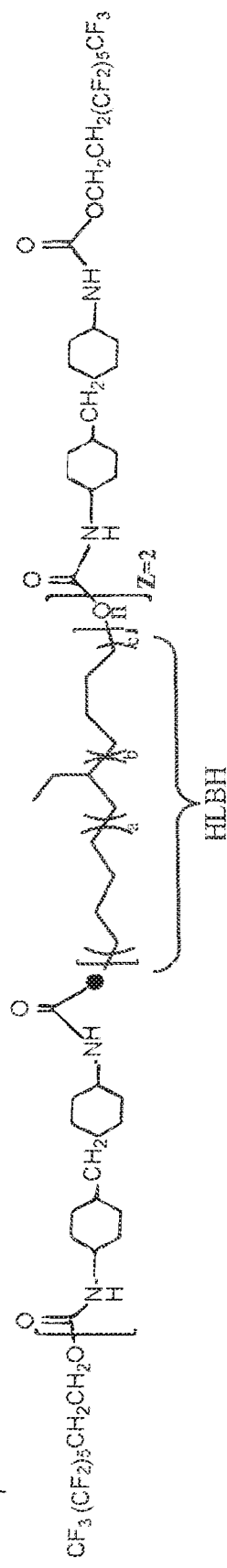
FIG. 2A shows a structure of compound 3.

The reaction was carried out as described for compound 2 using 180 g (74 mmol) hydrogenated-hydroxyl terminated polybutadiene (HLBH polyol, MW=2000) and 30.14 g (115 mmol) of 4,4'-methylene-bis(cyclohexyl isocyanate) (HMDI) to form the prepolymer. The prepolymer was end-capped with 40.48 g (111.18 mmol) of 1H,1H,2H,2H-perfluoro-1-octanol (C8-FOH) to form compound 3 as a colorless rubbery semi-solid. As described above, the couplings were carried out in the presence of bismuth carboxylate catalyst, and compound 3 was washed similarly to compound 2 and dried prior to use. The theoretical chemical structure of compound 3 is shown in FIG. 2a.

Compound 4

Figure 2B:
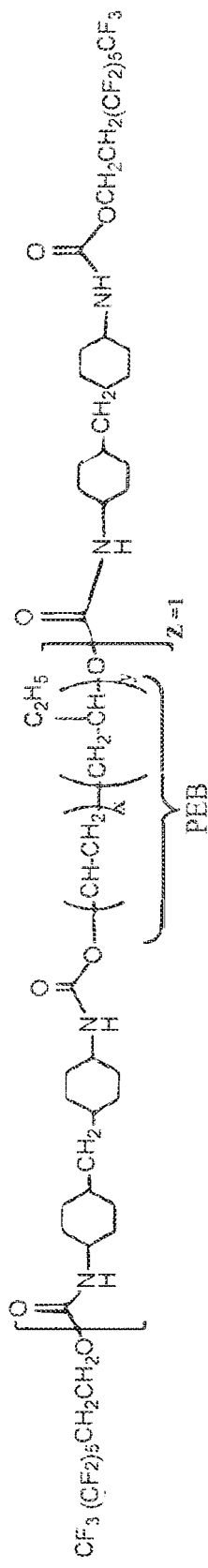
FIG. 2B shows a structure of compound 4.

The reaction was carried out as described for compound 3 using 10 g (4 mmol) poly(ethylene-co-butylene (PEB polyol, MW=2500) and 2.20 g (8.4 mmol) of 4,4'-methylene-bis(cyclohexyl isocyanate) (HMDI) to form the prepolymer. The prepolymer was capped with 3.64 g (10 mmol) of 1H, 1H, 2H, 2H-perfluoro-1-octanol (C8-FOH) to form compound 4. As described above, the couplings were carried out in the presence of bismuth carboxylate catalyst, and the compound 4 was washed similarly to compound 2 and dried prior to use. The theoretical chemical structure of compound 4 is shown in FIG. 2B.

Compound 5

Figure 3A:
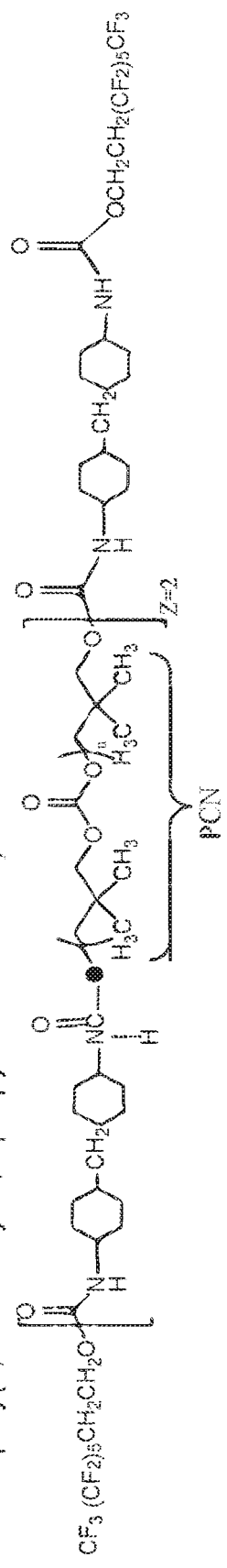
FIG. 3A shows a structure of compound 5.

The reaction was carried out as described for compound 4, except the solvent was changed from toluene to DMAc. Here, 100 g (100 mmol) poly(2,2-dimethyl-1,3-propylenecarbonate) diol (PCN, MW 1000) and 40.7 g (155 mmol) of 4,4'-methylene-bis(cyclohexyl isocyanate) (HMDI) to form a prepolymer. The prepolymer was end-capped with 45.5 g (125 mmol) of 1H,1H,2H,2H-perfluoro-1-octanol (C8-FOH) to form compound 5. The work-up after the reaction and the subsequent washing procedures are modified from the compound 4 synthesis as follows. Compound 5 from the reaction mixture in DMAc was precipitated in distilled water and washed successively in IPA/EDTA (Isopropanol/Ethylene Diamine Tetraacetic Acid) solution followed by another wash in IPA/hexanes to remove unreacted monomers, low molecular weight byproducts, and catalyst residues to yield compound 5 as a white amorphous powder. As described above, the couplings were carried out in the presence of bismuth carboxylate catalyst and dried under vacuum prior to use. The theoretical chemical structure of compound 5 is shown in FIG. 3A.

Compound 6

Figure 3B:
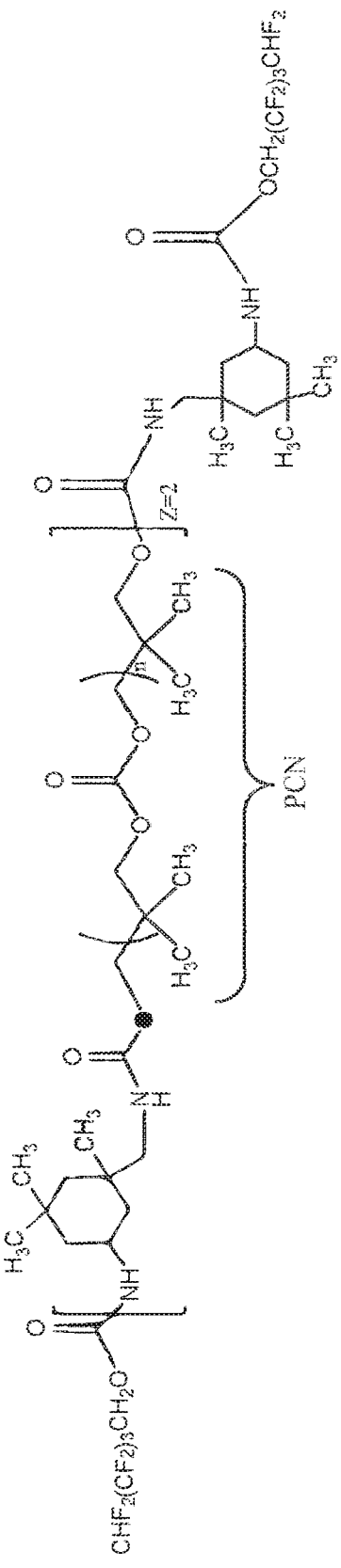
FIG. 3B shows a structure of compound 6.

The reaction was carried out as described for compound 5 using 6.0 g (6.0 mmol) poly(2,2 dimethyl-1,3-propylenecarbonate) diol (MW 1000) and 1.90 g (8.5 mmol) of isophorone diisocyanate (IPDI) to form the prepolymer. The prepolymer was end-capped with 1.4 g (6.0 mmol) of 1H,1H,5H-perfluoro-1-pentanol (C5-FOH) to form compound 6 as a white amorphous solid. As described above, the couplings were carried out in the presence of bismuth carboxylate catalyst, and compound 6 was washed similarly to compound 5 and dried prior to use. The theoretical chemical structure of compound 6 is shown in FIG. 3B.

Compound 7

Figure 4A:
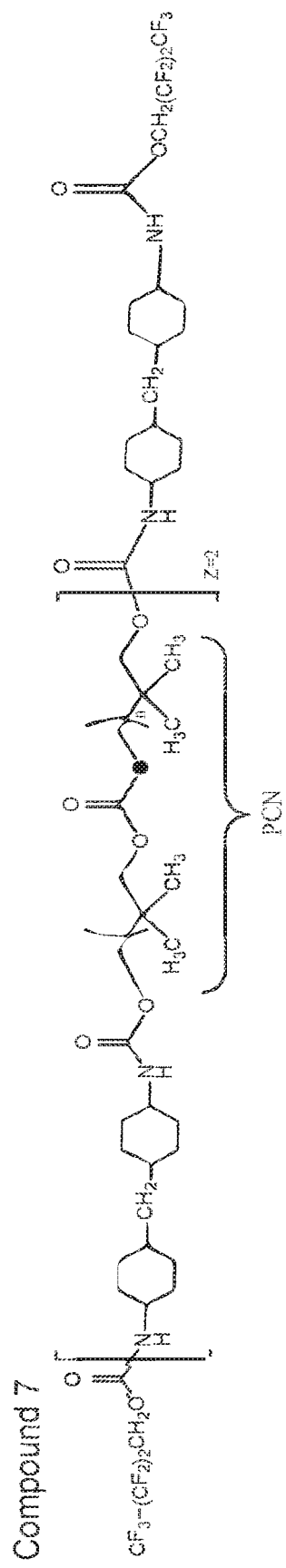
FIG. 4A shows a structure of compound 7.

The reaction was carried out as described for compound 5 using 10.0 g (10.0 mmol) poly(2,2-dimethyl-1,3-propylenecarbonate) diol (MW 1000) and 4.07 g (15.5 mmol) of 4,4'-methylene-bis(cyclohexyl isocyanate) (HMDI) to form the prepolymer. The prepolymer was capped with 2.5 g (12.5 mmol) of 1H, 1H-Perfluoro-1-butanol (C4-FOH) to form compound 8 as a white amorphous solid. As described above, the couplings were carried out in the presence of bismuth carboxylate catalyst, and compound 7 was washed similar to compound 5 and dried prior to use. The theoretical chemical structure of compound 7 is shown in FIG. 4A.

Compound 8

Figure 4B:
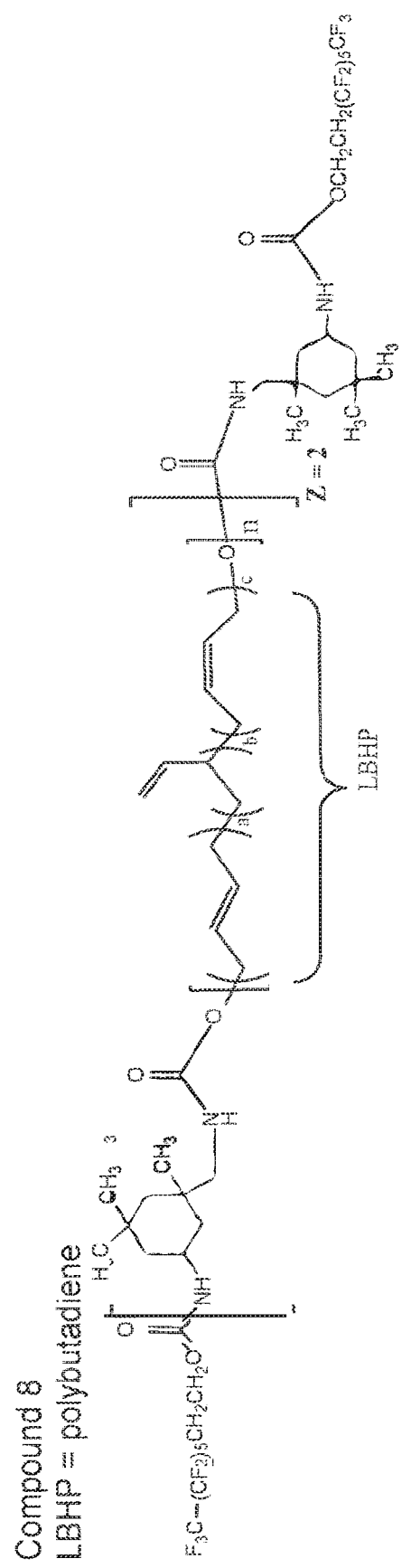
FIG. 4B shows a structure of compound 8.

The reaction was carried out as described for compound 5 using 180 g (84.8 mmol) hydroxyl-terminated polybutadiene (LBHP polyol, MW=2000) and 29.21 g (131.42 mmol) of isophorone diisocyanate (IPDI) to form the prepolymer. The prepolymer was capped with 46.31 g (127.18 mmol) of 1H,1H,2H,2H-perfluoro-1-octanol (C8-FOH) to form compound 8 as an off-white opaque viscous liquid. As described above, the couplings were carried out in the presence of bismuth carboxylate catalyst, and compound 8 was washed similarly to compound 5 and dried prior to use. The theoretical chemical structure of compound 8 is shown in FIG. 4B.

Compound 9

Figure 5A:
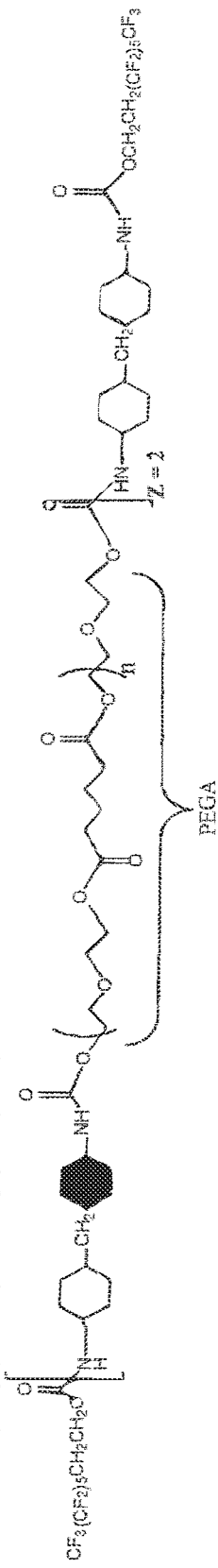
FIG. 5A shows a structure of compound 9.

The reaction was carried out as described for compound 5 using 10 g (3.92 mmol) poly(diethyhlene glycol adipate) (PEGA polyol, MW=2500) and 1.59 g (6.08 mmol) of 4,4'-methylene-bis(cyclohexyl isocyanate) (HMDI) to form a prepolymer. The prepolymer was capped with 2.14 g (5.88 mmol) of 1H,1H,2H,2H-perfluoro-1-octanol (C8-FOH) to form compound 9 as an off-white opaque viscous liquid. As described above, the couplings were carried out in the presence of bismuth carboxylate catalyst, and compound 9 was washed similarly to compound 5 and dried prior to use. The theoretical chemical structure of compound 9 is shown in FIG. 5A.

Compound 10

Figure 5B:
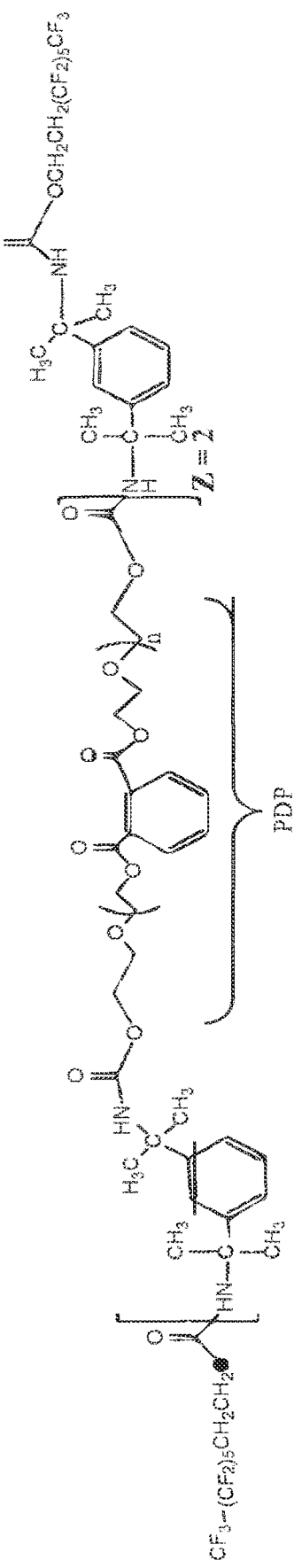
FIG. 5B shows a structure of compound 10.

The reaction was carried out as described for compound 5 using 10 g (5.06 mmol), ortho phthalate-diethylene glycol-based polyester polyol (PDP polyol, MW=2000) and 1.92 g (7.85 mmol) of m-tetramethylenexylene diisocyanate (TMXDI) to form a prepolymer. The prepolymer was capped with 2.76 g (7.59 mmol) of 1H,1H,2H,2H-perfluoro-1-octanol (C8-FOH) to form compound 10 as a colorless solid. As described above, the couplings were carried out in the presence of bismuth carboxylate catalyst, and compound 10 was washed similarly to compound 5 and dried prior to use. The theoretical chemical structure of compound 10 is shown in FIG. 5B.

Compound 11

Figure 6A:
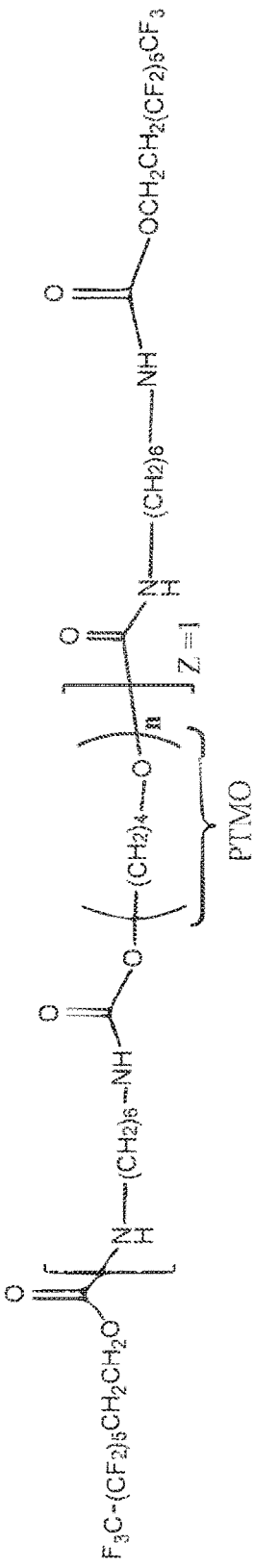
FIG. 6A shows a structure of compound 11.
Figure 6B:
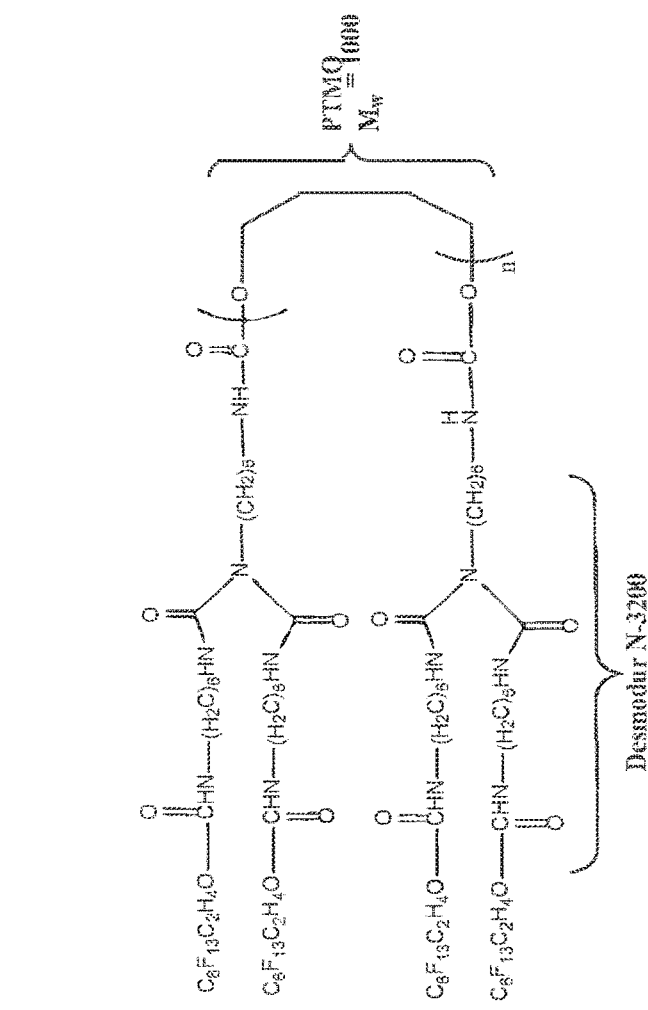
FIG. 6B shows a structure of compound 12.

Compound 11 was synthesized with PTMO diol of molecular weight 1000, 1,6-hexamethylene diisocyanate (HDI), and the low boiling fraction of the fluoroalcohol (BA-L). The conditions of the synthesis were as follows: 10 grams of PTMO were reacted with 3.36 grams of HDI for two hours and then 9 grams of BA-L (low boiling fraction) were added to the reaction. The mixture was reacted with 60 mL of the catalyst, dibutyltin dilaurate, in 70 mL of dimethyl-acetamide (DMAc), and the reaction temperature for the prepolymer step was maintained within 60-70° C. The polystyrene equivalent weight average molecular weight is $3.0 \times 10^4$ and its total fluorine content is 7.98% by weight. The theoretical chemical structure of compound 11 is shown in FIG. 6A.

Compounds 12-26

Figure 9:
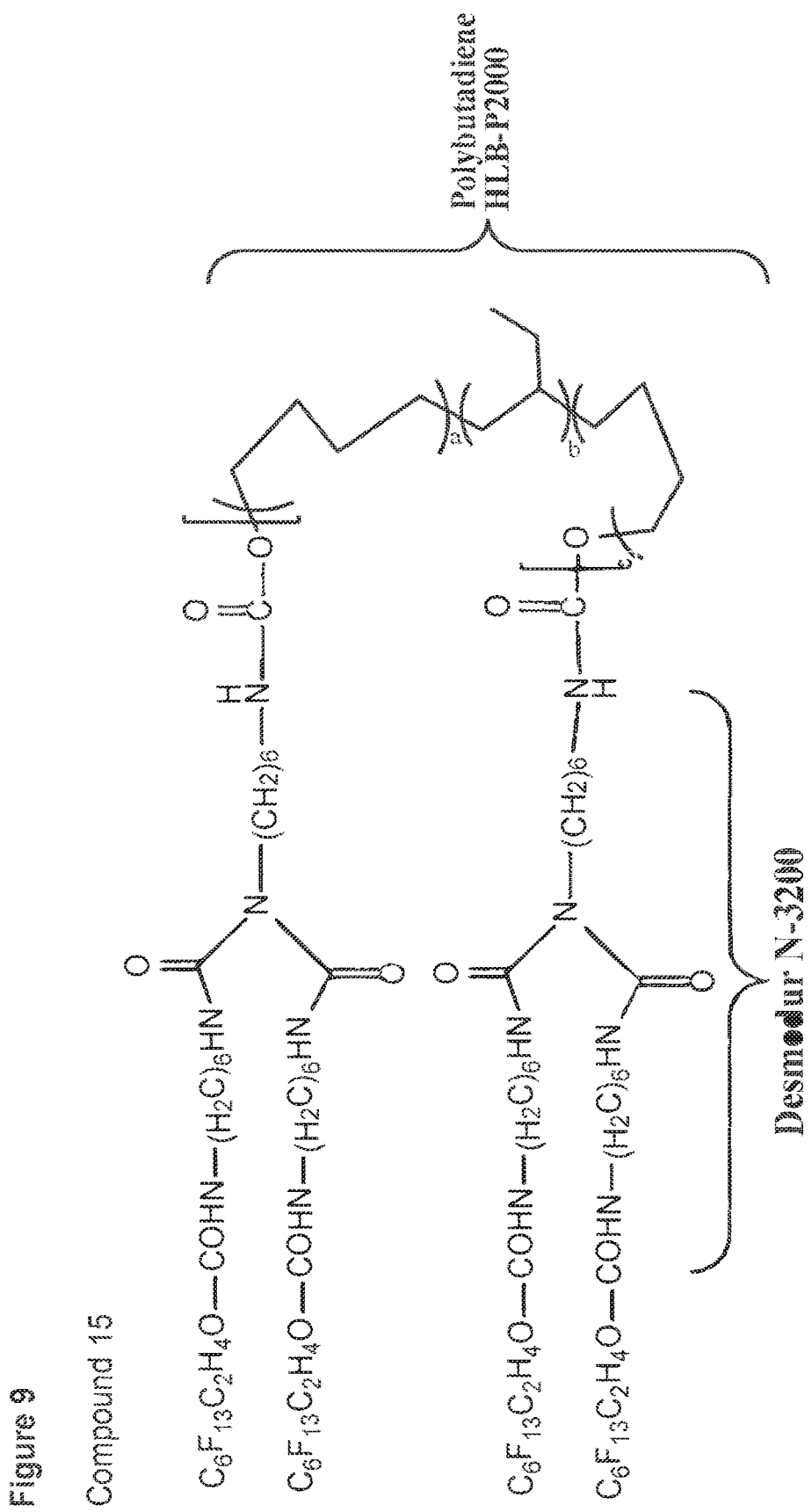
FIG. 9 shows a structure of compound 15.
Figure 11:
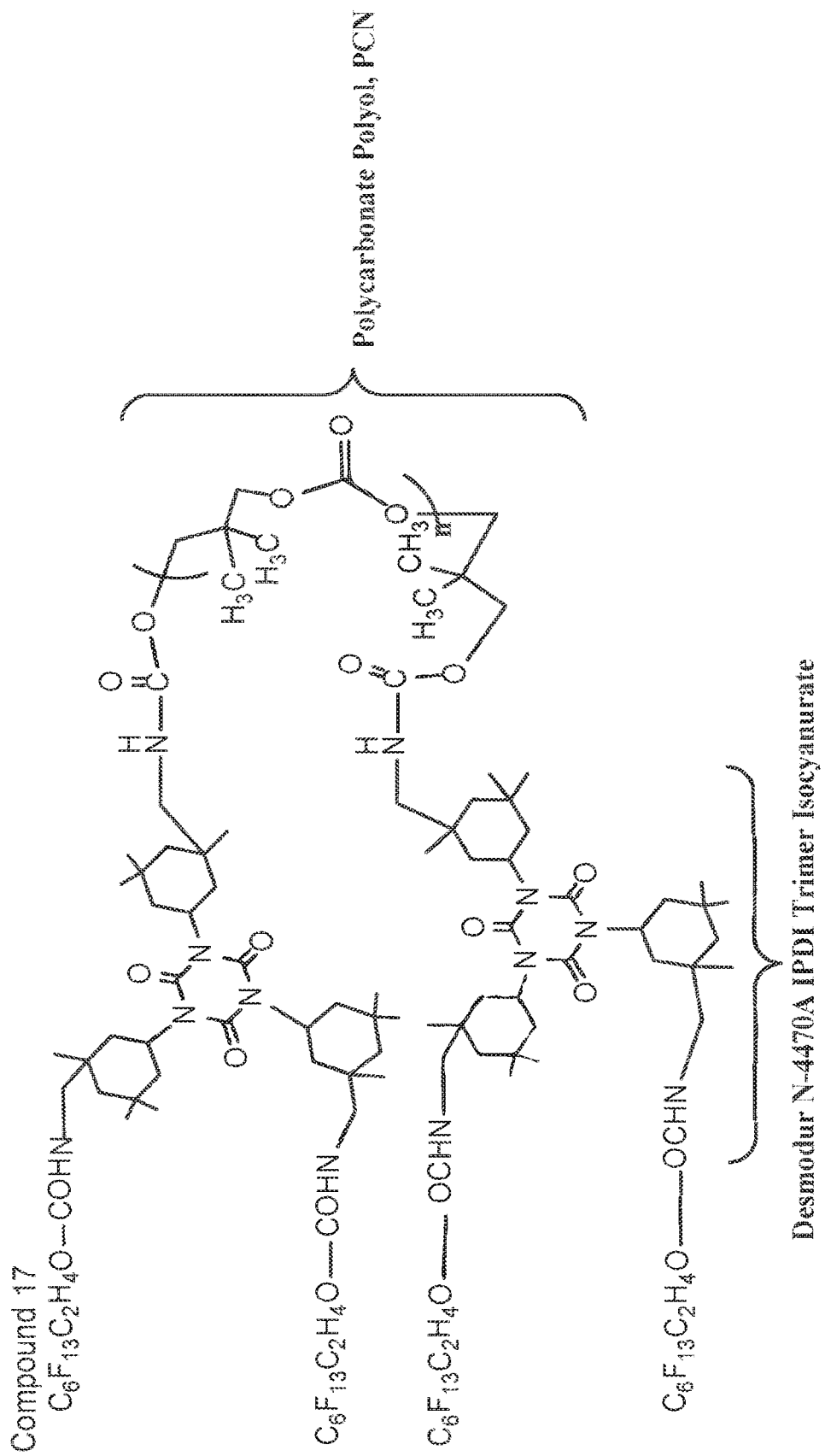
FIG. 11 shows a structure of compound 17.
Figure 12:
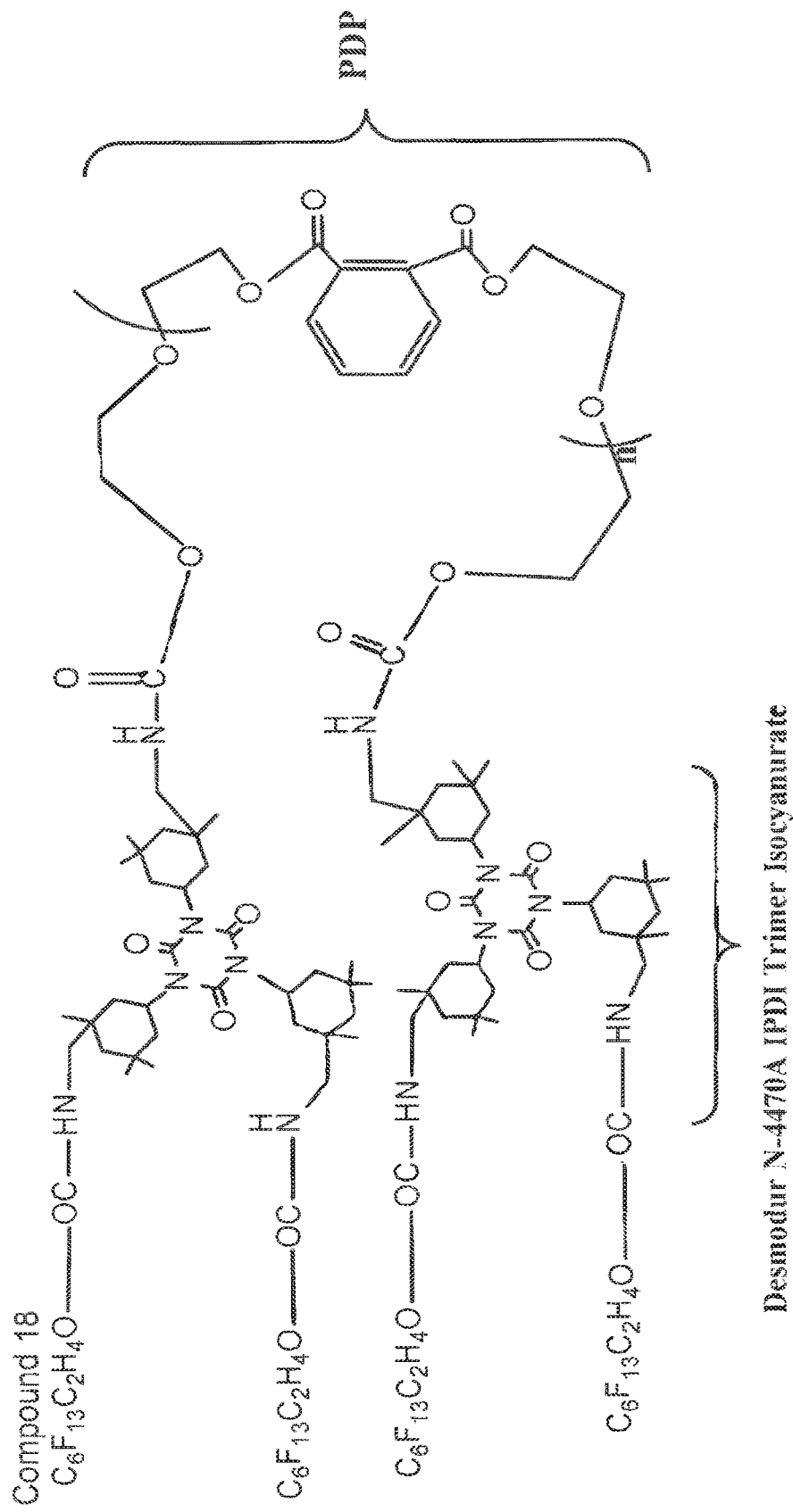
FIG. 12 shows a structure of compound 18.
Figure 13:
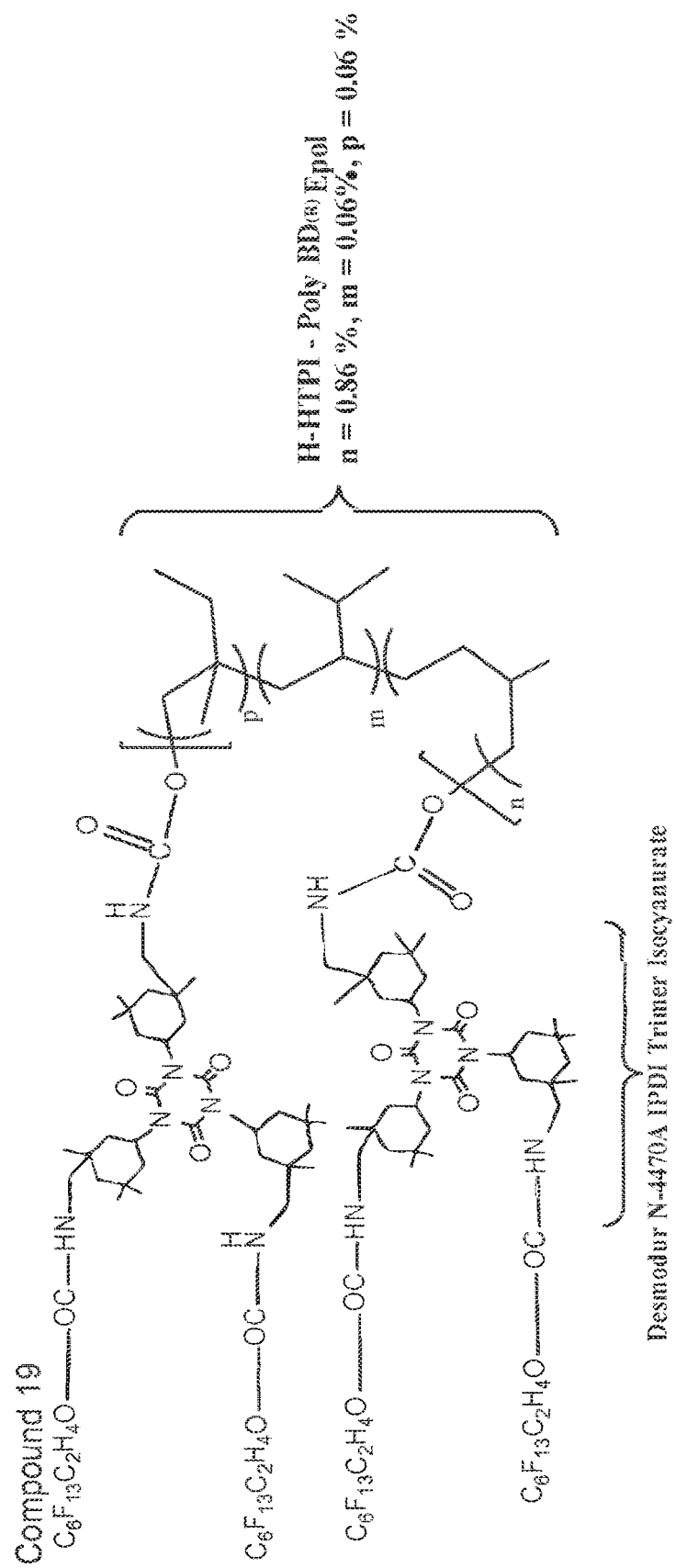
FIG. 13 shows a structure of compound 19.
Figure 14:
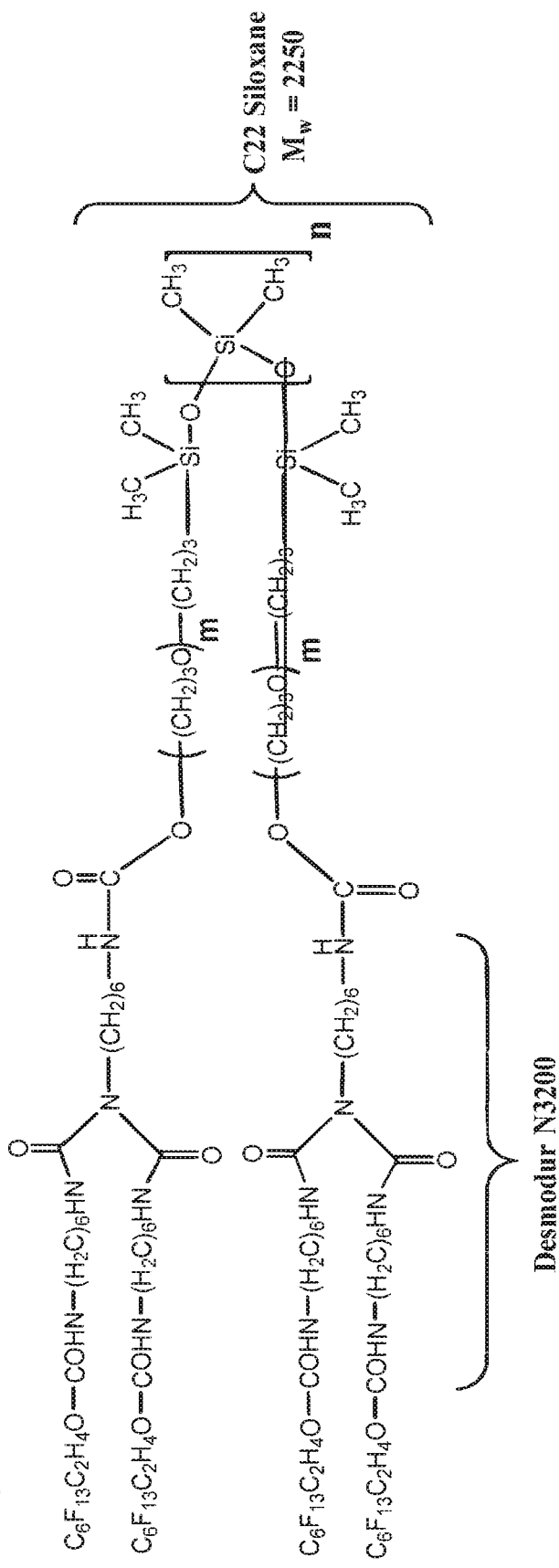
FIG. 14 shows a structure of compound 20.
Figure 15:
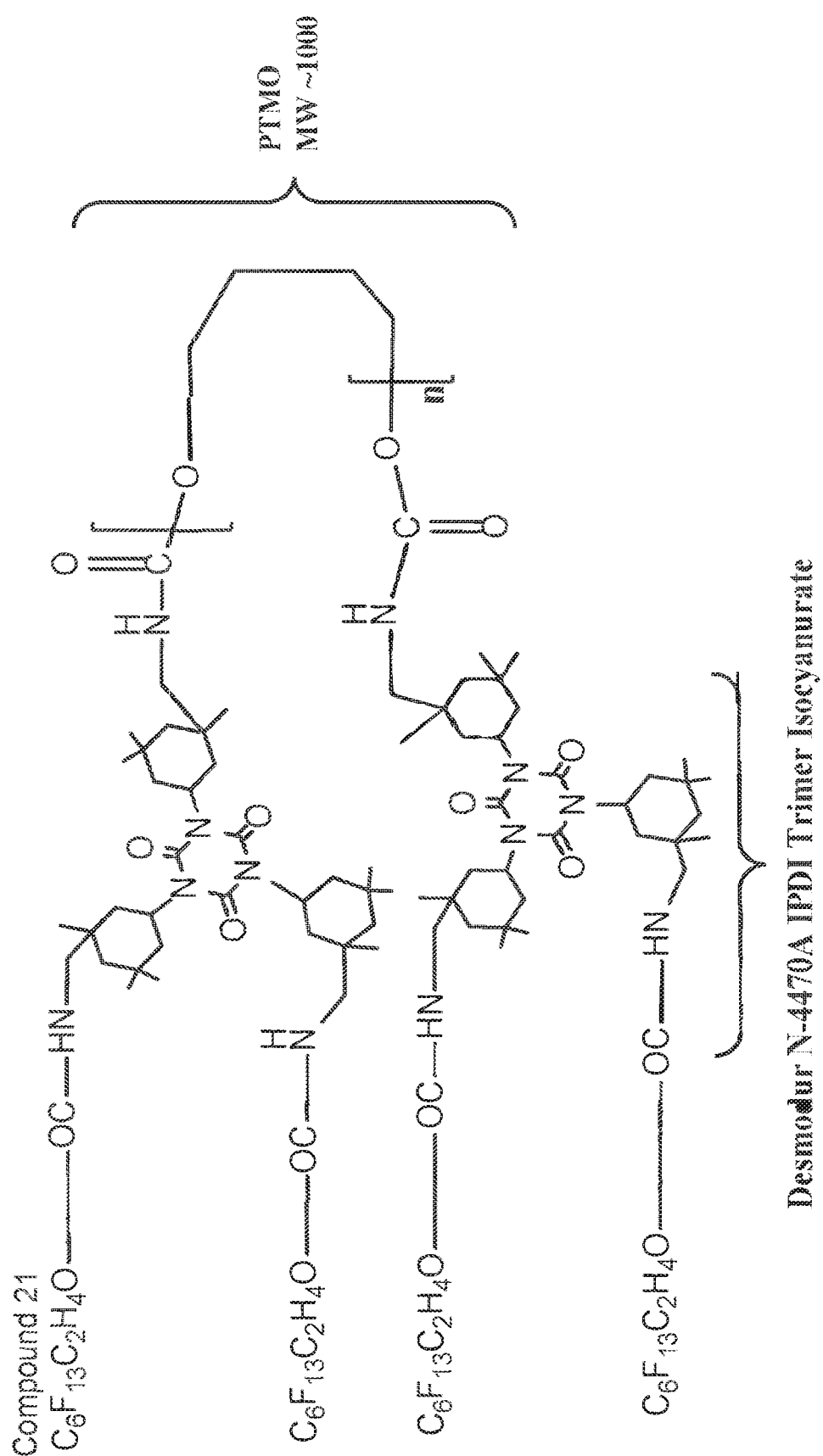
FIG. 15 shows a structure of compound 21.
Figure 16:
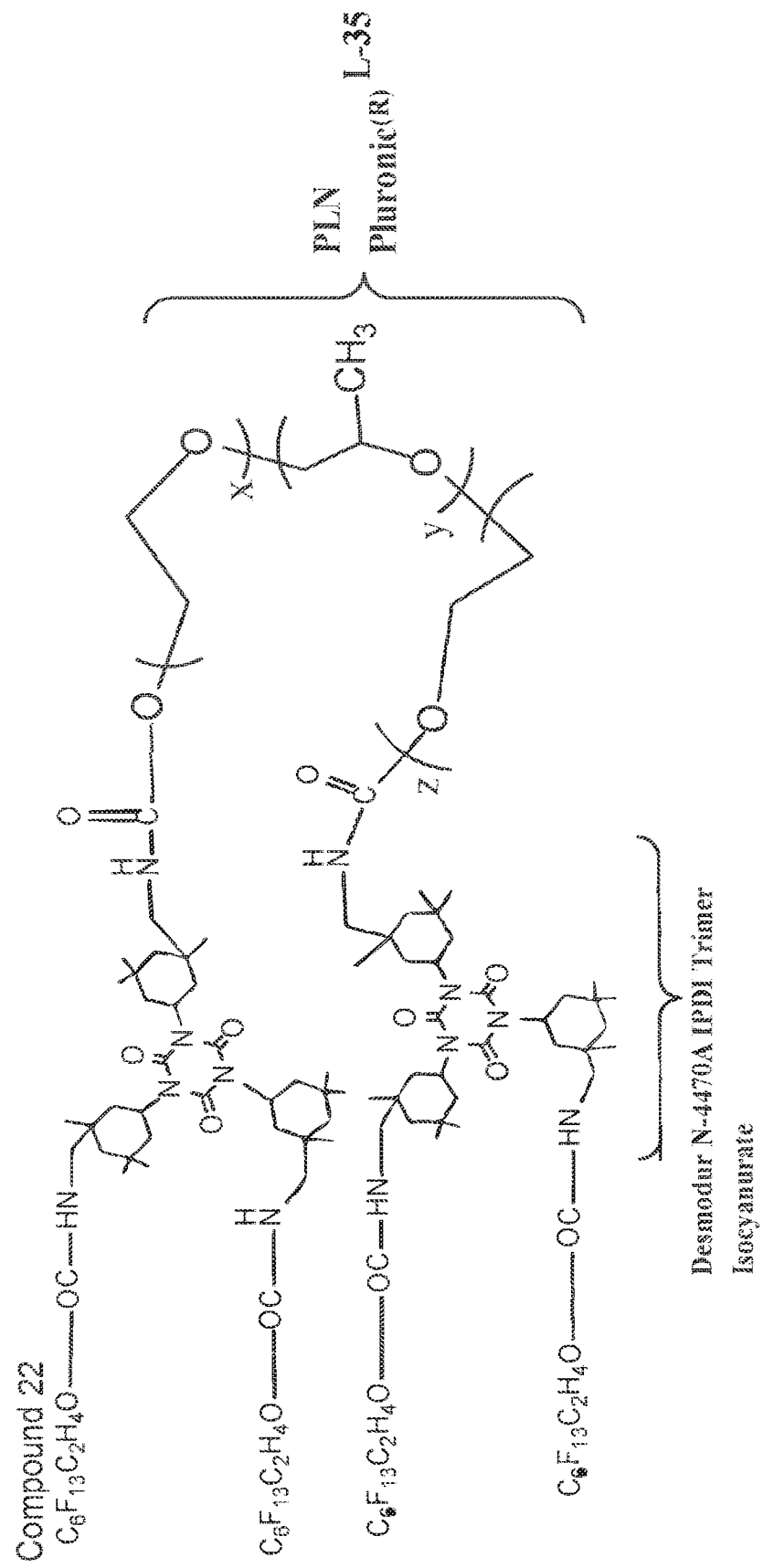
FIG. 16 shows a structure of compound 22.
Figure 17:
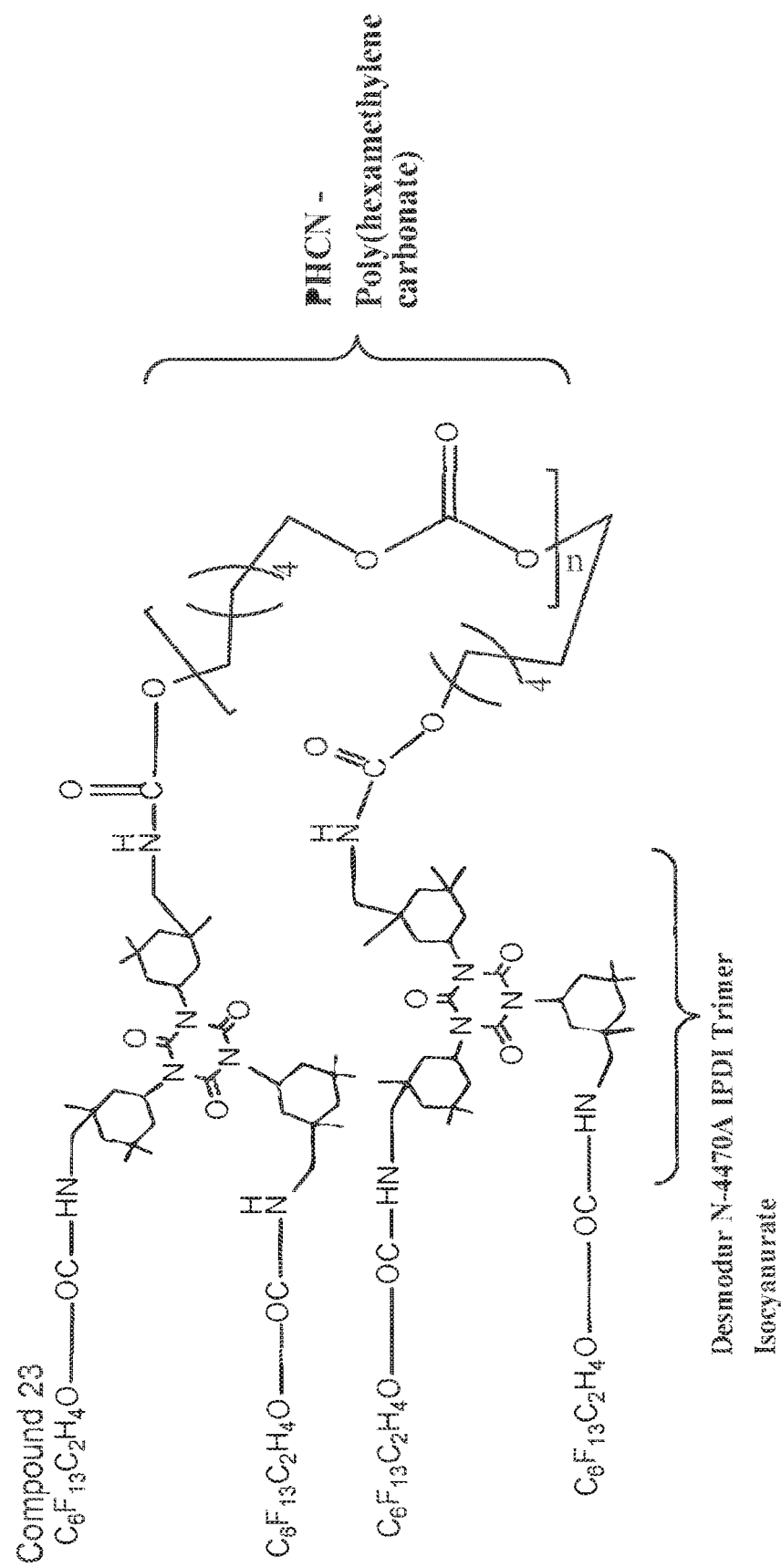
FIG. 17 shows a structure of compound 23.
Figure 18:
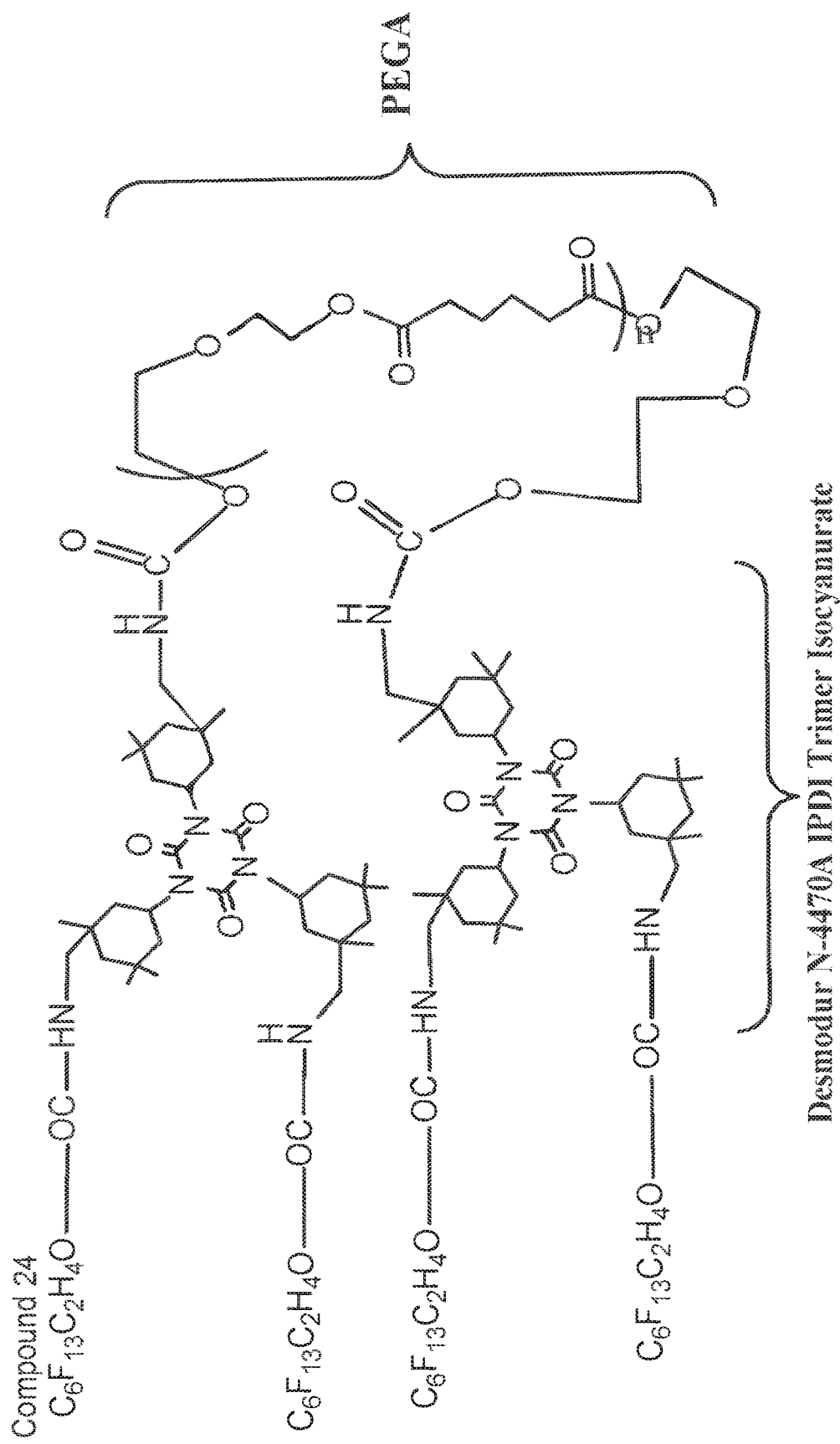
FIG. 18 shows a structure of compound 24.
Figure 19:
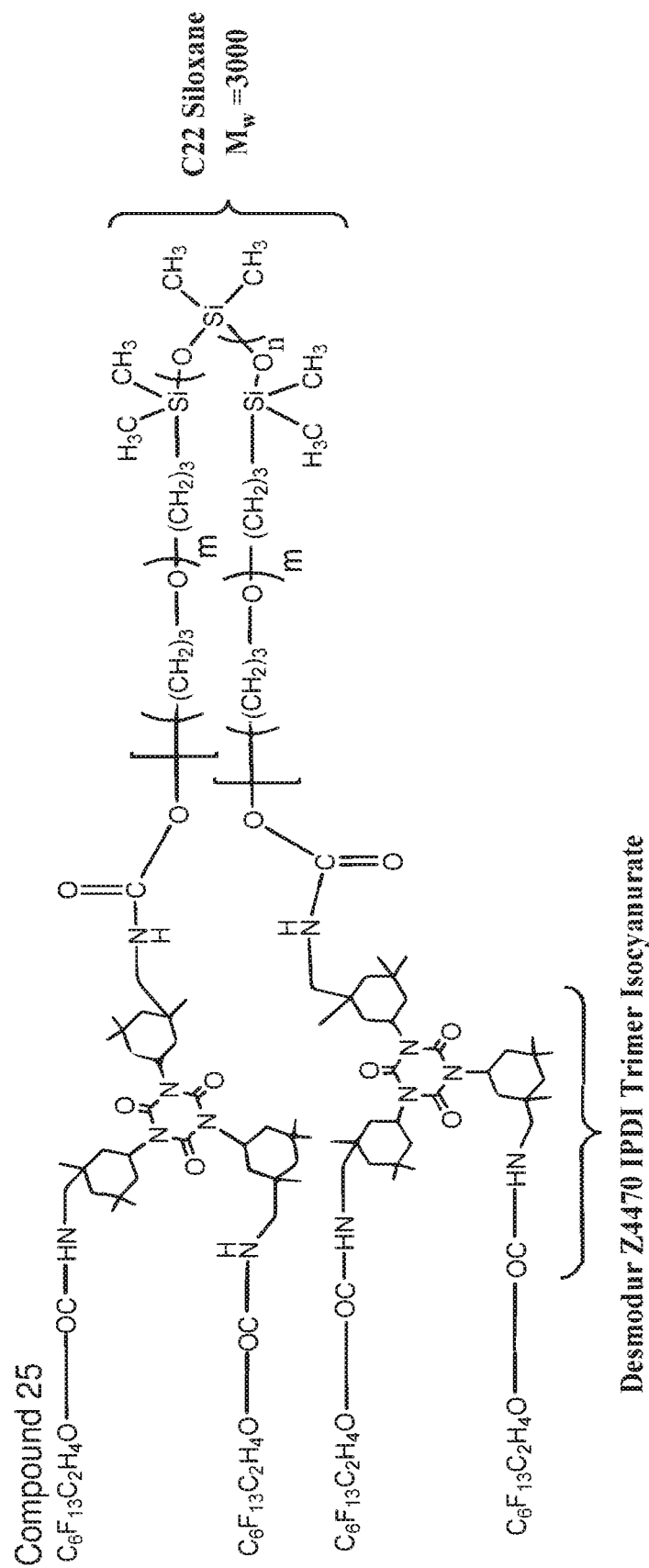
FIG. 19 shows a structure of compound 25.
Figure 20:
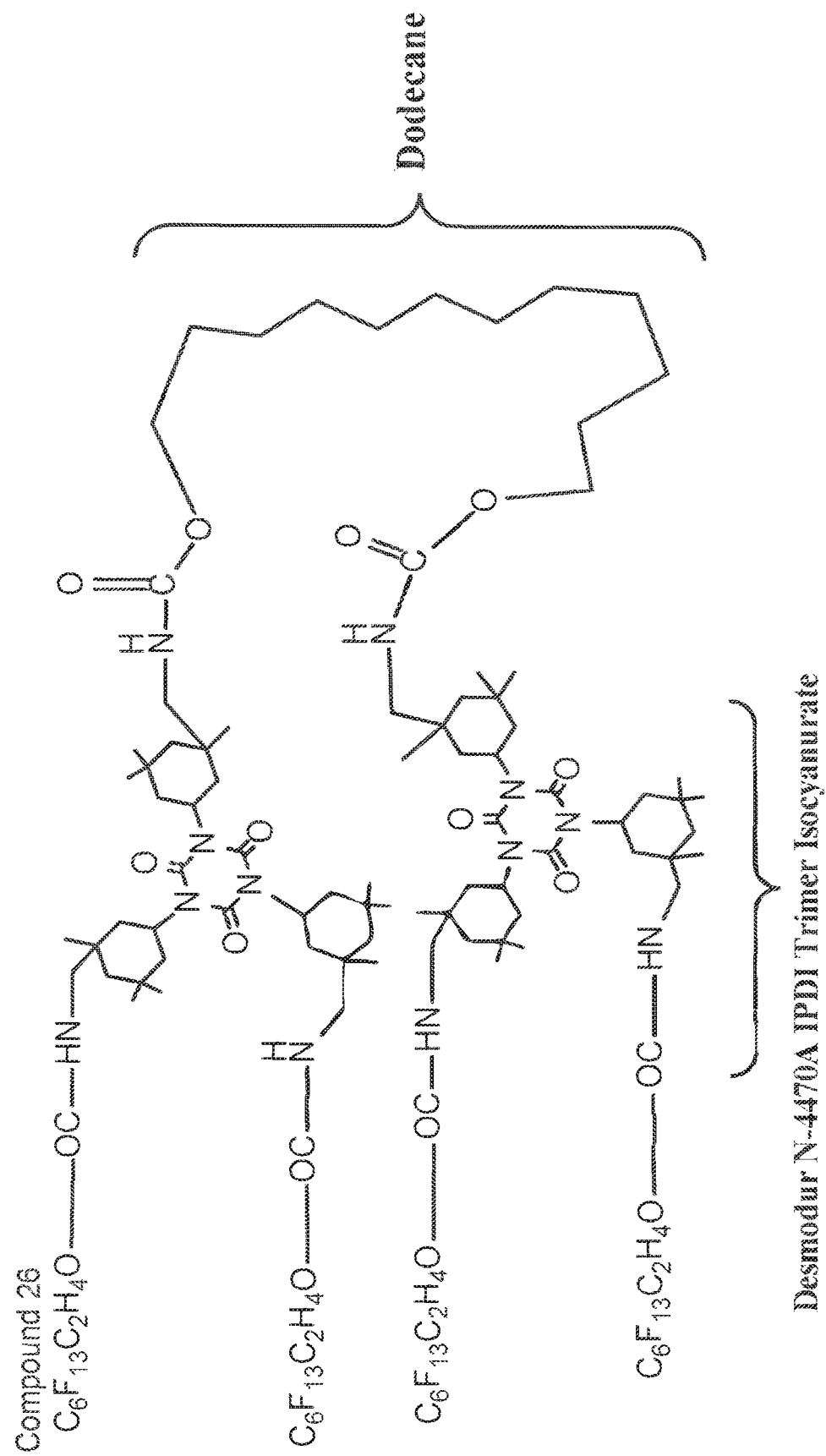
FIG. 20 shows a structure of compound 26.

Surface modifiers of the invention such as compound 15 and compound 17 may be synthesized by a 2-step convergent method according to the schemes depicted in schemes 1 and 2. Briefly, the polyisocyanate such as Desmodur N3200 or Desmodur 4470 is reacted dropwise with the surface-active group (e.g., a fluoroalcohol) in an organic solvent (e.g. anhydrous THF or dimethylacetamide (DMAc)) in the presence of a catalyst at 25° C. for 2 hours. After addition of the fluoroalcohol, stirring is continued for 1 hour at 50° C. and for a further 1 hour at 70° C. These steps lead to the formation of a partially fluorinated intermediate that is then coupled with the polyol (e.g., hydrogenated-hydroxyl terminated polybutadiene, or poly(2,2-dimethyl-1,3-propylenecarbonate)diol) at 70° C. over a period of 14 hours to provide the SMM. Because the reactions are moisture sensitive, they are carried out under an inert $N_2$ atmosphere and anhydrous conditions. The temperature profile is also maintained carefully, especially during the partial fluorination, to avoid unwanted side reactions. The reaction product is precipitated in MeOH and washed several times with additional MeOH. The catalyst residues are eliminated by first dissolving the SMM in hot THF or in hot IPA followed by reacting the SMM with EDTA solution, followed by precipitation in MeOH. Finally, the SMM is dried in a rotary evaporator at 120-140° C. prior to use. The theoretical chemical structure of compounds 15 and 17 is shown in FIGS. 9 and 11, respectively.

Scheme 1
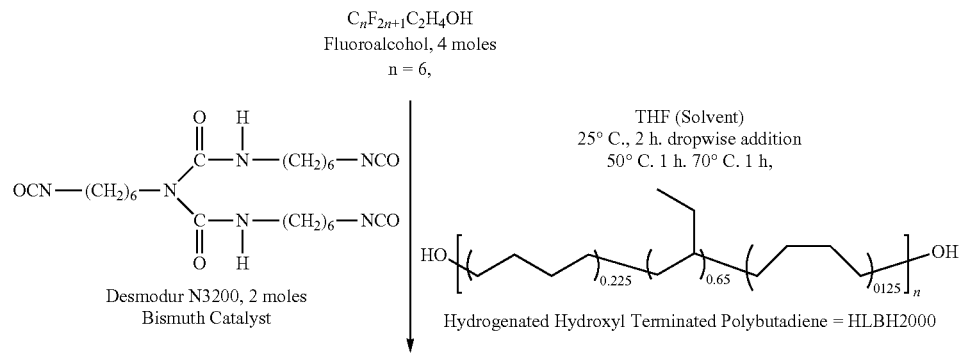
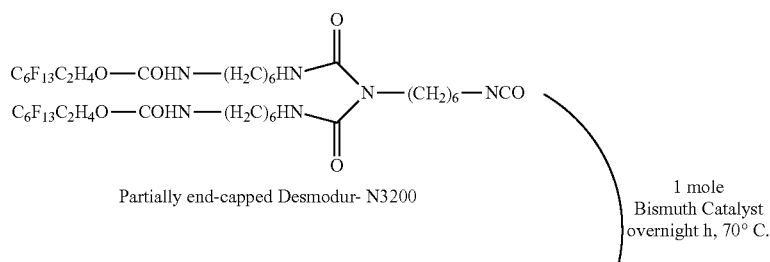
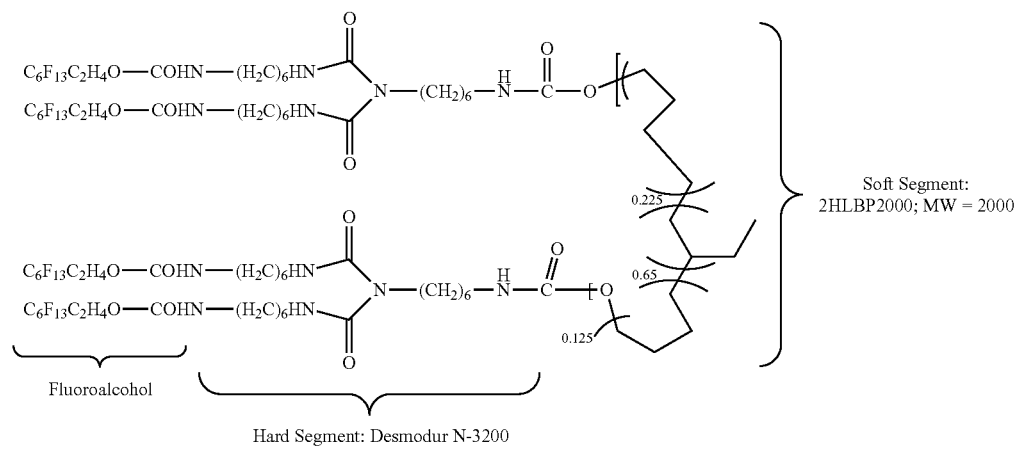

Scheme 2
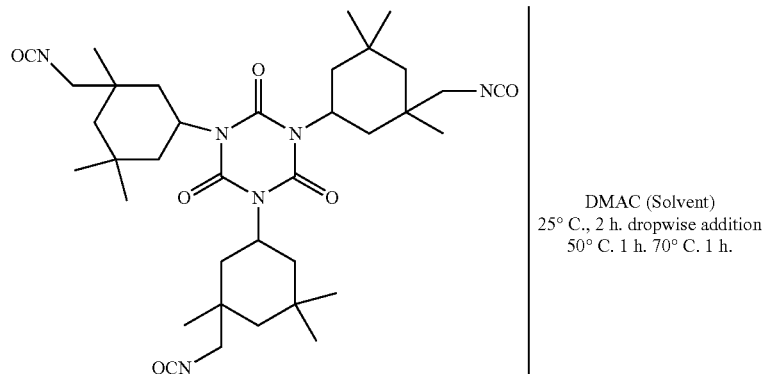
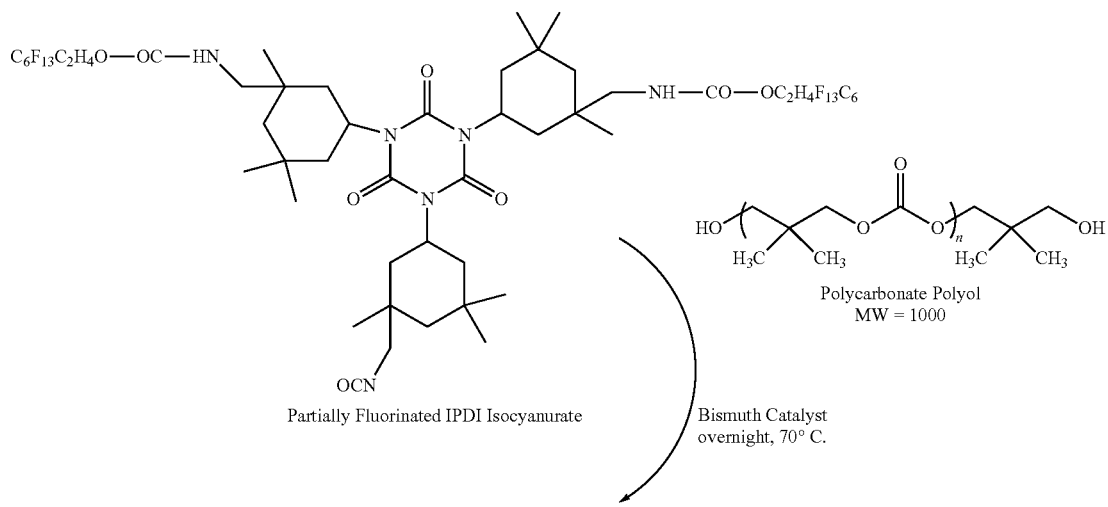

-continued

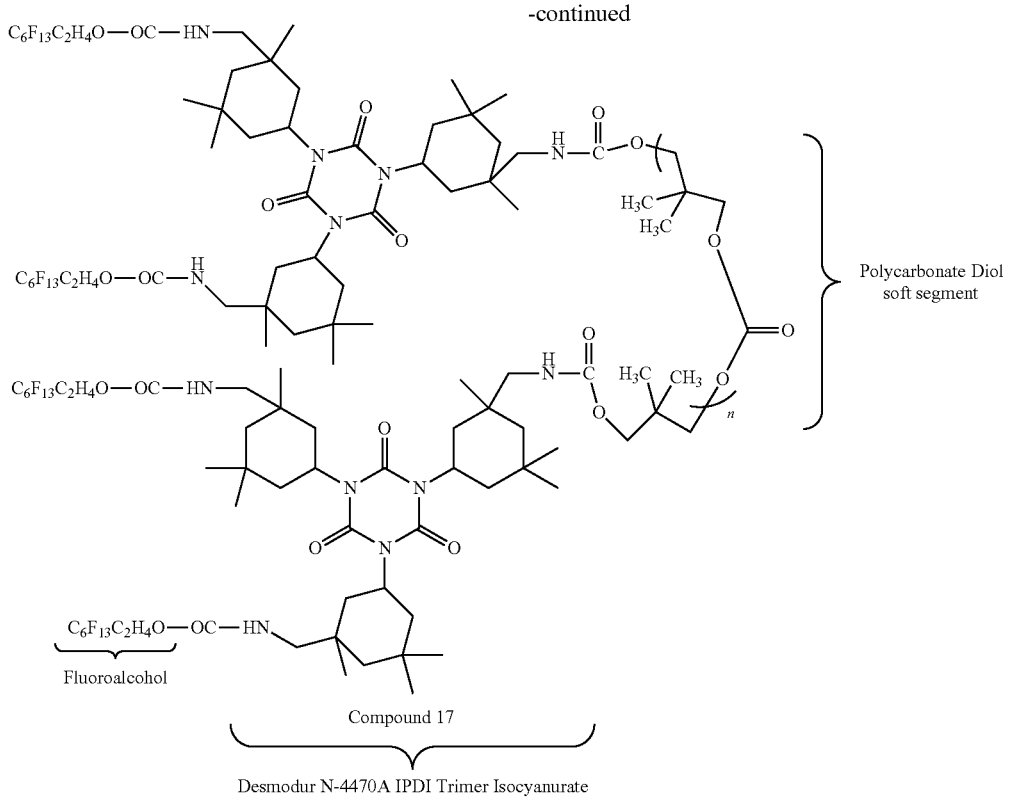

Compound 17

All glassware were dried in the oven overnight at 110° C. To a 3-necked 5000 mL reactor equipped with a stir bar and a reflux condenser was added 300 g (583 mmol) of Desmodur N3300. The mixture was degassed overnight at ambient temperature. Hydrogenated-hydroxyl terminated polybutadiene (HLBH polyol MW=2000) was measured into a 2000 mL flask and degassed at 60° C. overnight. The bismuth catalyst K-Kat 348 (a bismuth carboxylate; available from King Industries) was measured out into a 250 mL flask and degassed overnight at ambient temperature. The perfluorinated alcohol was measured into a 1000 mL flask and degassed for 30 minutes at ambient temperature. After degassing, all the vessels were purged with Nitrogen.

300 mL of THF (or DMAc) was then added to the Desmodur N3300 containing vessel, and the mixture was stirred to dissolve the polyisocyanate. Similarly, 622 mL of THF was added to the HLBH polyol, and the mixture was stirred to dissolve the polyol. Likewise, 428 mL of THF (or DMAC) was added to the perfluorinated alcohol and the mixture was stirred to dissolve. Similarly for K-Kat 348 which was dissolved in 77 mL of THF or DMAC. Stirring was continued to ensure all the reagents were dissolved in their respective vessels.

Figure 10:
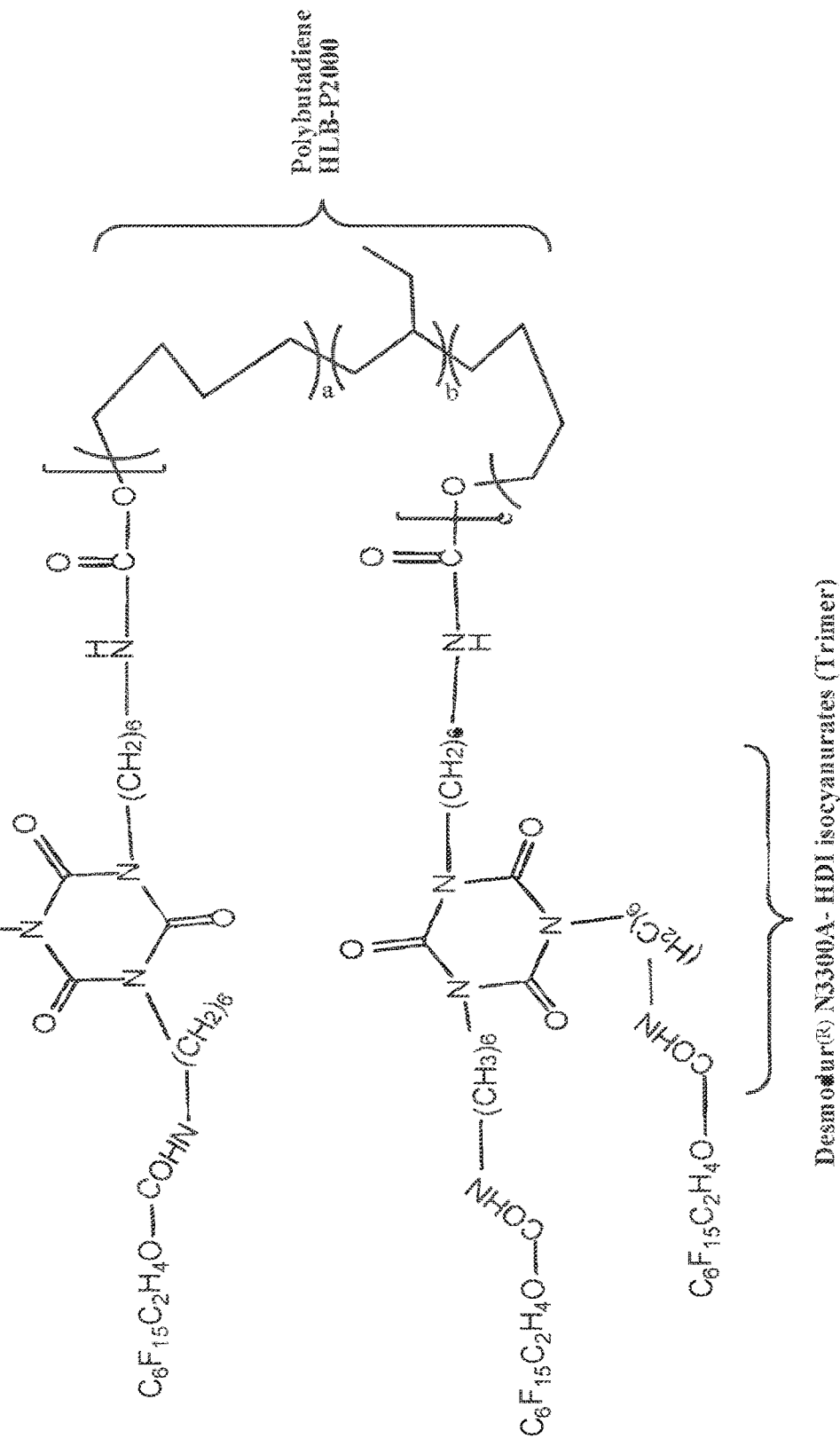
FIG. 10 shows a structure of compound 16.

Half the K-Kat solution was transferred to the perfluorinated solution which was stirred for 5 minutes. This solution was added to the reaction vessel containing the Desmodur N3300 solution dropwise over a period of 2 hours at ambient (25° C.) temperature through a cannula (double ended needle) under positive nitrogen pressure. After addition, the temperature was raised to 50° C. for 1 hour and 70° C. for another 1 hour. Proper stirring was maintained throughout. The remaining K-Kat 348 catalyst was transferred to the HLBH-2000 flask; after stirring to dissolve, this was added to the reactor containing the N3300. The reaction mixture was allowed to react overnight for 14 hours at 70° C. to produce compound 16 with four fluorinated end groups. The theoretical chemical structure of compound 16 is shown in FIG. 10.

Exemplary SMMs that can be prepared according to the procedures described for compounds 15-17 are illustrated in FIGS. 6B and 11-20.

General Synthesis Description for Ester-Based SMMs

A diol such as Ymer diol, hydroxyl terminated polydimethylsiloxane, or polyols such as trimethylolpropane ethoxylate or pentaerythritol ethoxylate are reacted in a one-step reaction with a surface-active group precursor (e.g., perfluoroheptanoyl chloride) at 40° C. in a chlorinated organic solvent e.g. chloroform or methylene chloride in the presence of an acid scavenger like pyridine or triethylamine for 24 h. This reaction end-caps the hydroxyl groups with polyfluoroorgano groups. Because the reactions are moisture sensitive, the reactions are carried out under a nitrogen atmosphere using anhydrous solvents. After the reaction the solvent is rotary evaporated and the product is dissolved in Tetrahydrofuran (THF) which dissolves the product and precipitates the pyridine salts which are filtered off and the filtrate rotary evaporated further to dryness. The product is then purified by dissolving in minimum THF and precipitating in hexanes. This is performed 3 times and after which the final product is again rotary evaporated and finally dried in a vacuum oven at 60° C. overnight.

Compound 27

Glassware used for the synthesis was dried in an oven at 110° C. overnight. To a 2-necked 1000 mL oven dried round bottom flask equipped with a stir bar was added 85 g (24 mmol) of C25-Diol (MW=3500). The flask with the diol was degassed overnight at 60° C. with gentle stirring and then purged with dry $N_2$ the following day. The heating was turned off. A 1000 mL graduated cylinder was charged with 320 mL anhydrous CHCl$_3$, sealed by a rubber septa and purged with dry N$_2$. The CHCl$_3$ was transferred to the 2-necked flask via a cannula and the diol stirred vigorously to dissolve in the solvent. Anhydrous pyridine (11.53 g, 146 mmol) was added to the C25-Diol solution using a plastic syringe, and the resulting mixture was stirred to dissolve all materials. Another oven dried 2-necked 1000 mL flask was charged with 32.51 g (85 mmol) of perfluoroheptanoyl chloride. The flask was sealed with rubber septa and degassed for 5 minutes, then purge with nitrogen. At this time 235 mL of anhydrous CHCl$_3$ were added via cannula to the 1000 mL 2-necked flask containing the perfluoroheptanoyl chloride. Stir at room temperature to dissolve the acid chloride. This flask was fitted with an addition funnel and the C25-Diol-pyridine solution in CHCl$_3$ was transferred via a cannula into the addition funnel. N$_2$ flow through the reactor was adjusted to a slow and steady rate. Continuous dropwise addition of C25-Diol-pyridine solution to the acid chloride solution was started at room temperature and was continued over a period of ~4 hours. Stirring was maintained at a sufficient speed to achieve good mixing of reagents. After completing addition of the C25-Diol-pyridine solution, the addition funnel was replaced with an air condenser, and the 2-neck flask was immerses in an oil bath placed on a heater fitted with a thermocouple unit. The temperature was raised to 40° C., and the reaction continued at this temperature under N$_2$ for 24 h.

Figure 21A:
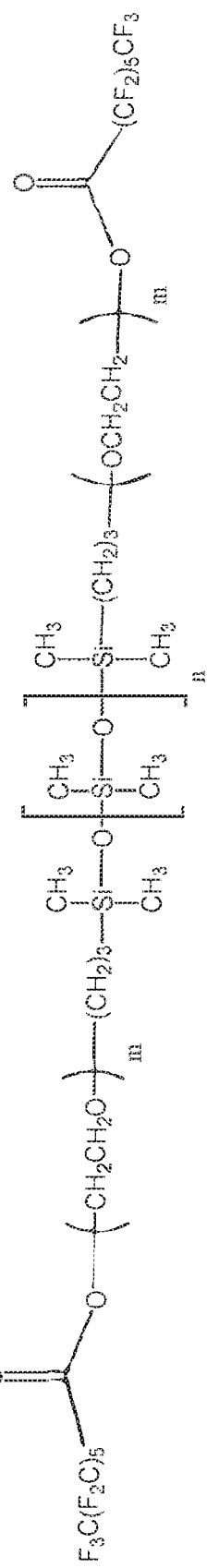
FIG. 21A shows a structure of compound 27.
Figure 21B:
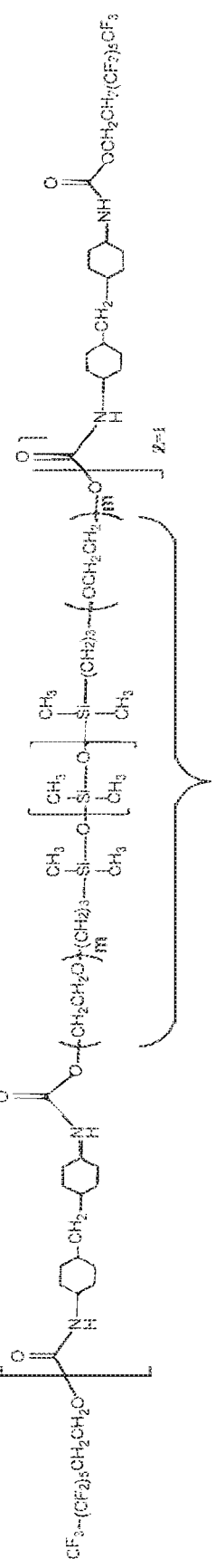
FIG. 21B shows a structure of compound 28.

The product was purified by evaporating CHCl$_3$ in a rotary evaporator and by filtering the pyridine salts after addition of THF. The crude product was then precipitated in isopropanol/hexanes mixture twice. The oil from the IPA/Hexane that precipitated was subjected to further washing with hot hexanes as follows. About 500 mL of Hexanes was added to the oil in a 1 L beaker with a stir bar. The mixture was stirred while the Hexanes was heated to boiling. The heating was turned off, and the mixture was allowed to cool for 5 minutes. The oil settles at the bottom at which point the Hexane top layer is decanted. The isolated oil is further dissolved in THF, transferred to a round bottom flask and then the solvents rotary evaporated. The oil is finally dried in a vacuum oven at 40° C. for 24 h. The purified product (a mixture of di- and mono-substituted products) was characterized by GPC (Molecular Weight based on Polystyrene Standards), elemental analysis for fluorine, $^{19}$F NMR, $^1$H NMR, FTIR, and TGA. Appearance: viscous oil. Weight Average molecular weight (polystyrene equivalent)=5791 g/mol. Polydispersity: 2.85. Elemental analysis: F: 7.15% (theory: 10.53%). $^{19}$F NMR (CDCl$_3$, 400 MHz. ppm): δ−80.78 (m, CF$_3$), −118.43 (m, CF$_2$), −121.85 (m, CF$_2$), −122.62 (m, CF$_2$), −126.14 (m, CF$_2$). $^1$H NMR (CDCl$_3$, 400 MHz): δ ppm=0.0 (m, CH$_3$Si), 0.3 (br m, CH$_2$Si), 1.4 (br m, CH$_2$), 3.30 (m, CH$_2$'s), 4.30 (m, CH$_2$COO—). FTIR, neat (cm$^{-1}$): 3392 (OH), 2868 (CH$_2$), 1781 (O—C=O, ester), 1241, 1212, 1141, 1087 (CF$_3$, CF$_2$). The theoretical chemical structure of compound 27 is shown in FIG. 21A.

Compound 29

Glassware used for the synthesis was dried in an oven at 110° C. overnight. To a 2-necked 100 mL oven dried round bottom flask equipped with a stir bar was added 10 g (5 mmol) of PDMS C22-Diol (C22 diol, MW=3000). The flask with the diol was degassed overnight at 60° C. with gentle stirring and then purged with dry N$_2$ the following day. Heating was turned off. A 100 mL graduated cylinder was filled with 50 mL anhydrous CHCl$_3$, sealed with a rubber septum, and purged with dry N$_2$. The CHCl$_3$ was transferred to the 2-necked flask via a cannula, and the diol was stirred vigorously to dissolve in the solvent. Anhydrous pyridine (0.53 g, 7 mmol) was then added to the C22-Diol solution using a plastic syringe, and the resulting mixture was stirred to dissolve all materials. Another oven-dried 2-necked 250 mL flask was charged with 3.19 g (8 mmol) perfluoroheptanoyl chloride. The flask was then sealed with a rubber septum, and the mixture in the flask was degassed for 5 minutes and purged with nitrogen. Then, 22 mL of anhydrous CHCl$_3$ were added using a graduated cylinder and a cannula to transfer the solvent to the 250 mL 2-necked flask containing the perfluoroheptanoyl chloride. The resulting mixture was stirred at room temperature to dissolve the acid chloride. The flask was then equipped with an addition funnel, and the C22 diol/pyridine solution in CHCl$_3$ was transferred to the addition funnel using a cannula. N$_2$ flow through the reactor was adjusted to a slow and steady rate. C22 diol/pyridine solution was then added continuously drop-wise to the acid chloride solution at room temperature over a period of ~4 hours. Stirring was maintained at a sufficient speed to achieve good mixing of reagents. After completing the addition of the C22 diol, the addition funnel was replaced with an air condenser, and the 2-necked flask was immersed in an oil bath placed on a heater fitted with a thermocouple unit. The temperature was raised to 50° C., and the reaction mixture was left at this temperature under N$_2$ for 24 h.

Figure 22:
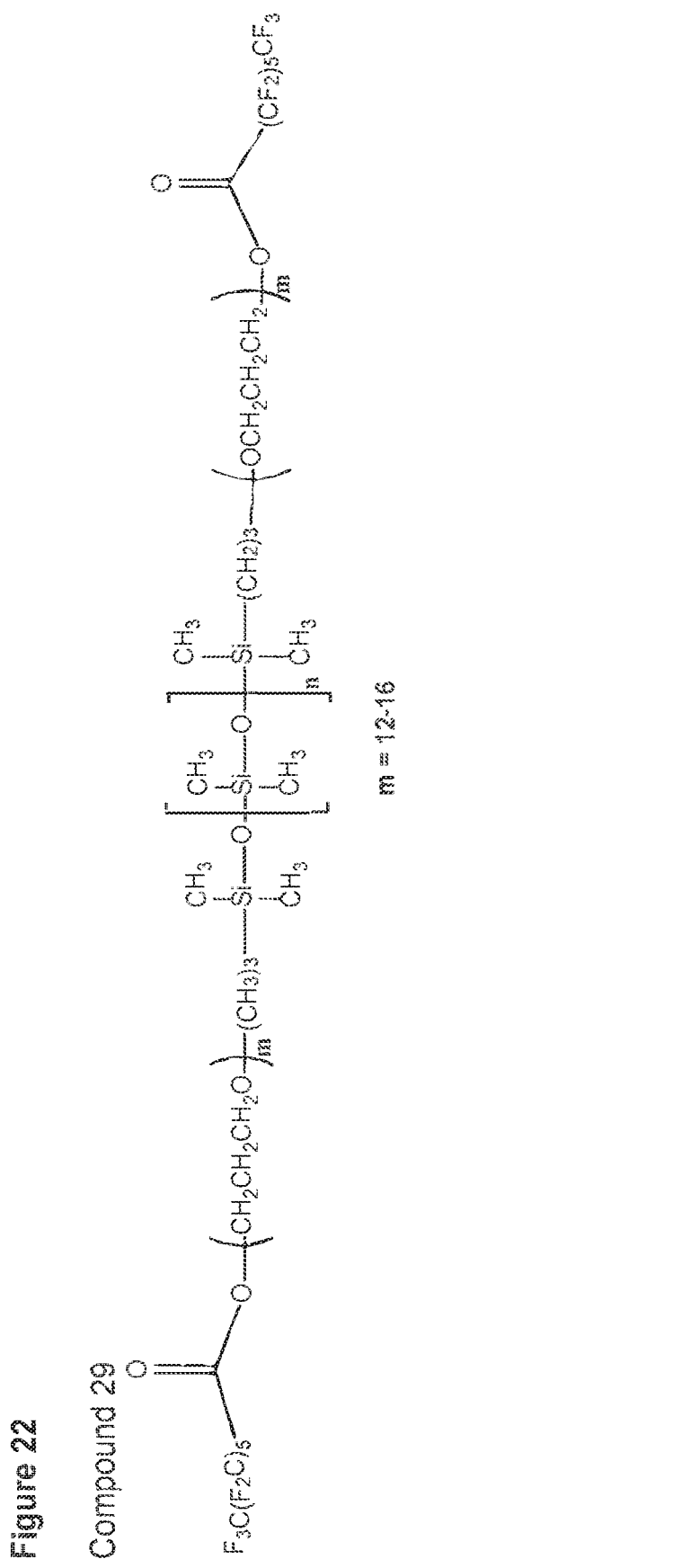
FIG. 22 shows a structure of compound 29.

Then, heating and stirring were turned off. The flask was removed and its contents were poured into a round bottom flask. Volatiles were removed by rotary evaporation. Upon concentration, a dense precipitate (pyridine salts) formed. THF was added to dissolve the product, and the precipitated pyridine salts were removed by filtration using a coarse Whatman Filter paper (No 4), as the pyridine salts are insoluble in THF. Volatiles were removed by rotary evaporation. The crude product was then dissolved in 100 mL of CHCl$_3$ and poured into a separatory funnel. 150 mL of water and 5 mL of 5N HCl were added to neutralize any remaining pyridine. The funnel was shaken, and the product was extracted into CHCl$_3$. The bottom CHCl$_3$ layer containing product was then washed in a separatory funnel sequentially with water, 5 mL of 5% (w/v) NaHCO$_3$ solution to neutralize any remaining HCl, and with distilled water. The CHCl$_3$ layer was separated and concentrated by rotary evaporation to obtain crude product, which was then dissolved in 10 mL of isopropanol. The resulting solution was added dropwise to a 1 L beaker containing 200 mL of DI Water with 1% (v/v) MeOH with continuous stirring. The product separated out as oil, at which time the solution was kept in an ice bath for 20 minutes, and the top aqueous layer was decanted. The oil was dissolved in THF and transferred into a 200 mL round bottom flask. The volatiles were removed by rotary evaporation at a maximum of 80° C. and 4 mbar to remove residual solvents. The resulting product was dried in a vacuum oven at 60° C. for 24 h to give a purified product as a light yellow, clear oil (~64% yield). The purified product was characterized by GPC (Molecular Weight based on Polystyrene Standards), and elemental analysis (for fluorine) . Appearance: Light Yellow clear oil. Weight Average Molecular Weight (Polystyrene equivalent) Mw=5589, Polydispersity PD=1.15. Elemental Analysis F: 12.86% (theory: 13.12%). The theoretical chemical structure of compound 29 is shown in FIG. 22.

Compound 30

Glassware used for the synthesis was dried in an oven at 110° C. overnight. To a 2-necked 250 mL oven dried round bottom flask equipped with a stir bar was added 20 g (8.0 mmol) of hydrogenated-hydroxyl terminated polybutadiene (HLBH diol, MW=2000). The flask with the diol was degassed overnight at 60° C. with gentle stirring and then purged with dry N$_2$ the following day. At this time, the heating was turned off. A 200 mL graduated cylinder was charged with 104 mL anhydrous CHCl$_3$, sealed by a rubber septa, and purged with dry N$_2$. The CHCl$_3$ was transferred to the 2-necked flask via a cannula, and the diol was stirred vigorously to dissolve in the solvent. At this time, anhydrous pyridine (3.82 g, 48 mmol) was added to the HLBH diol solution using a plastic syringe, and the resulting mixture was stirred to dissolve all materials. Another oven dried 2-necked 100 mL flask was charged with trans-5-norbornene-2,3-dicarbonyl chloride ("NCI"; 3.70 g, 17 mmol), sealed with rubber septa, and degassed for 5 minutes, and then purged with nitrogen. At this time, 52 mL of anhydrous CHCl$_3$ were added using a graduated cylinder and a cannula to transfer the solvent to the 100 mL 2-necked flask containing NCI. The resulting mixture was stirred to dissolve NCI. The 250 mL 2-necked flask was then fitted with an addition funnel, and the solution of NCI in CHCl$_3$ was transferred to the addition funnel using a cannula. N$_2$ flow was adjusted through the reactor to a slow and steady rate. The solution of NCI was added continuously drop-wise to the HLBH-pyridine solution at room temperature over a period of ~1 hour to form a pre-polymer. Stirring was maintained at a sufficient speed to achieve good mixing of reagents.

In parallel, another oven-dried 50 mL flask was charged with Capstone™ Al-62 perfluorinated reagent (5.45 g, 15 mmol). The flask was sealed with rubber septa, degassed for 15 minutes, and purged with N$_2$. Anhydrous CHCl$_3$ (17 mL) and anhydrous pyridine (1.9 g, 24 mmol) were added. The mixture was stirred to dissolve all reagents. After the addition of the NCI solution to the 250 mL 2-necked flask was complete, the Capstone™ Al-62 perfluorinated reagent solution was added to this flask using a cannula with stirring. The addition funnel was replaced with an air condenser, and the 250-mL 2-necked flask was immersed in an oil bath placed on a heater fitted with a thermocouple unit. The temperature was raised to 50° C., and the reaction continued at this temperature under N$_2$ for 24 h.

Figure 23A:
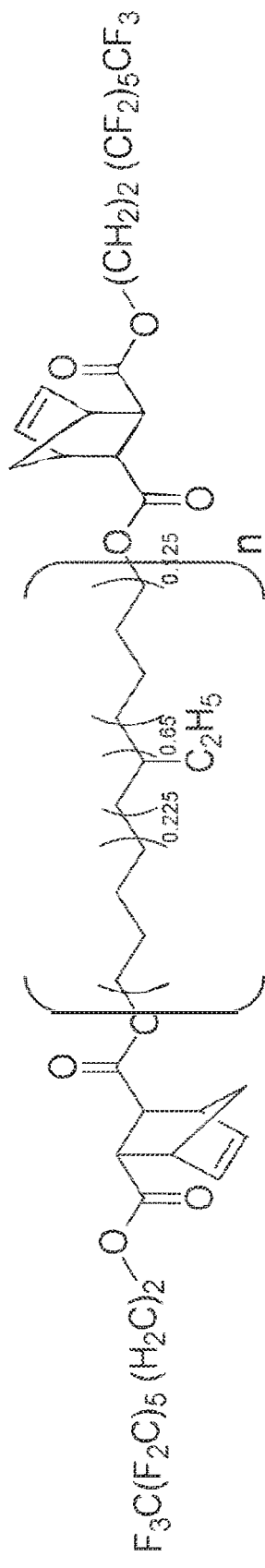
FIG. 23A shows a structure of compound 30.

After the reaction, heating and stirring were turned off. The reaction flask was removed, and its contents were poured into a round bottom flask. CHCl$_3$ was removed by rotary evaporation. Upon concentration, a dense precipitate (pyridine salts) formed. THF was added to dissolve the product, and the precipitated pyridine salts were removed by filtration using a coarse Whatman Filter paper (No 4). Pyridine salts are insoluble in THF. THF was removed by rotary evaporation. The crude product was dissolved in 100 mL of CHCl$_3$ and was poured into a separatory funnel. 100 mL of water were added, followed by the addition of 5 mL of (5N) HCl to neutralize any remaining pyridine. The funnel was shaken, and the product was extracted into CHCl$_3$. The bottom CHCl$_3$ layer containing product was isolated and washed in a separatory funnel with water (5 mL of 5% NaHCO$_3$ solution were added to neutralize any remaining HCl). The organic layer was then washed once more with plain distilled water. Isolated CHCl$_3$ layer was concentrated by rotary evaporation to obtain crude product. The crude product was dissolved in 10 mL of isopropanol (IPA) and was then added dropwise to a beaker containing 200 mL of deionized water containing 1% (v/v) MeOH with continuous stirring. Product separated out as an oil. The mixture was kept in ice bath for 20 minutes, and the top water layer was decanted. The oil was dissolved in THF and transferred into 200 mL round bottom flask. THF was removed by rotary evaporation at a maximum temperature of 80° C. and 4 mbar to remove all residual solvents. The resulting product was dried in a vacuum oven at 60° C. for 24 h to give a purified product as a viscous oil (~55% yield). The purified product (a mixture of di- and mono-substituted products) was characterized by GPC, elemental analysis, for fluorine, and Hi-Res TGA. Appearance: light yellow viscous liquid. Weight Average molecular weight (polystyrene equivalent)=12389 g/mol. Polydispersity, PD: 1.43. Elemental analysis: F: 10.6% (theory: 14.08%). The theoretical chemical structure of compound 30 is shown in FIG. 23A.

Compound 31

Compound 31 was prepared according to a procedure similar to compound 30. Glassware used for the synthesis was dried in an oven at 110° C. overnight. To a 2-necked 250 mL oven dried round bottom flask equipped with a stir bar was added 15 g (6.0 mmol) of hydrogenated-hydroxyl terminated polybutadiene (HLBH diol, MW=2000). The flask with the diol was degassed overnight at 60° C. with gentle stirring and then purged with dry N$_2$ the following day. At this time, the heating was turned off. A 100 mL graduated cylinder was charged with 12 mL anhydrous CHCl$_3$, sealed by a rubber septa, and purged with dry N$_2$. The CHCl$_3$ was transferred to the 2-necked flask via a cannula, and the diol was stirred vigorously to dissolve in the solvent. At this time, anhydrous pyridine (0.95 g, 12 mmol) was added to the HLBH diol solution using a plastic syringe, and the resulting mixture was stirred to dissolve all materials. Another oven dried 2-necked 100 mL flask was charged with terephthaloyl chloride (2.57 g, 13 mmol), sealed with rubber septa, and degassed for 5 minutes, and then purged with nitrogen. At this time, 85 mL of anhydrous CHCl$_3$ were added using a graduated cylinder and a cannula to transfer the solvent to the 100 mL 2-necked flask. The resulting mixture was stirred to dissolve terephthaloyl chloride. The 250 mL 2-necked flask was then fitted with an addition funnel, and the solution of terephthaloyl chloride in CHCl$_3$ was transferred to the addition funnel using a cannula. N$_2$ flow was adjusted through the reactor to a slow and steady rate. The solution of terephthaloyl chloride was added continuously drop-wise to the HLBH-pyridine solution at room temperature over a period of ~1 hour to form a pre-polymer. Stirring was maintained at a sufficient speed to achieve good mixing of reagents.

In parallel, another oven-dried 50 mL flask was charged with Capstone™ Al-62 perfluorinated reagent (5.45 g, 15 mmol). The flask was sealed with rubber septa, degassed for 15 minutes, and purged with N$_2$. Anhydrous CHCl$_3$ (12 mL) and anhydrous pyridine (0.95 g, 12 mmol) were added. The mixture was stirred to dissolve all reagents. After the addition of the terephthaloyl chloride solution to the 250 mL 2-necked flask was complete, the Capstone™ Al-62 perfluorinated reagent solution was added to this flask with stirring. The addition funnel was replaced with an air condenser, and the 250-mL 2-necked flask was immersed in an oil bath placed on a heater fitted with a thermocouple unit. The temperature was raised to 50° C., and the reaction continued at this temperature under N$_2$ for 24 h.

Figure 23B:
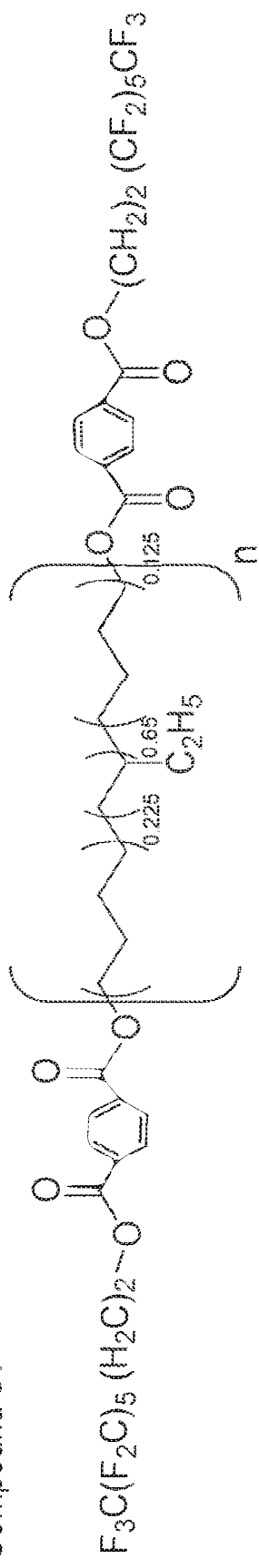
FIG. 23B shows a structure of compound 31.

After the reaction, heating and stirring were turned off. The reaction flask was removed, and its contents were poured into a round bottom flask. CHCl$_3$ was removed by rotary evaporation. Upon concentration, a dense precipitate (pyridine salts) formed. THF was added to dissolve the product, and the precipitated pyridine salts were removed by filtration using a coarse Whatman Filter paper (No 4). Pyridine salts are insoluble in THF. THF was removed by rotary evaporation. The crude product was dissolved in 100 mL of CHCl$_3$ and was poured into a separatory funnel. 100 mL of water were added, followed by the addition of 5 mL of (5N) HCl to neutralize any remaining pyridine. The funnel was shaken, and the product was extracted into CHCl$_3$. The bottom CHCl$_3$ layer containing product was isolated and washed in a separatory funnel with water (5 mL of 5% NaHCO$_3$ solution were added to neutralize any remaining HCl). The organic layer was then washed once more with plain distilled water. Isolated CHCl$_3$ layer was concentrated by rotary evaporation to obtain crude product. The crude product was dissolved in 10 mL of isopropanol (IPA) and was then added dropwise to a beaker containing 200 mL of deionized water containing 1% (v/v) MeOH with continuous stirring. Product separated out as an oil. The mixture was kept in ice bath for 20 minutes, and the top water layer was decanted. The oil was dissolved in THF and transferred into 200 mL round bottom flask. THF was removed by rotary evaporation at a maximum temperature of 80° C. and 4 mbar to remove all residual solvents. The resulting product was dried in a vacuum oven at 60° C. for 24 h to give a purified product as a viscous oil (~87% yield). The purified product (a mixture of di- and mono-substituted products) was characterized by GPC, elemental analysis, for fluorine, and Hi-Res TGA. Appearance: off-white viscous liquid. Weight Average molecular weight (polystyrene equivalent)=10757 g/mol. Polydispersity, PD: 1.33. Elemental analysis: F: 11.29% (theory: 14.21%). The theoretical chemical structure of compound 31 is shown in FIG. 23B.

Compound 33

Glassware used for the synthesis was dried in an oven at 110° C. overnight. To a 2-necked 100 mL oven dried round bottom flask equipped with a stir bar was added 10 g (5 mmol) of hydrogenated-hydroxyl terminated polyisoprene (HHTPI diol, MW=2000). The flask with the diol was degassed overnight at 60° C. with gentle stirring and then purged with dry N$_2$ the following day. At this time, the heating was turned off. A 100 mL graduated cylinder was charged with 50 mL anhydrous CHCl$_3$, sealed by a rubber septa, and purged with dry N$_2$. The CHCl$_3$ was transferred to the 2-necked flask via a cannula, and the diol was stirred vigorously to dissolve in the solvent. At this time, excess anhydrous pyridine (0.75 g, 9 mmol) was added to the HHTPI diol solution using a plastic syringe, and the resulting mixture was stirred to dissolve all materials. Another oven dried 2-necked 250 mL flask was charged with perfluoroheptanoyl chloride (4.51 g, 12 mmol), sealed with rubber septa, and degassed for 5 minutes, and then purged with nitrogen. At this time, 22 mL of anhydrous CHCl$_3$ was added using a graduated cylinder and a cannula to transfer the solvent to the 250 mL 2-necked flask containing the perfluoroheptanoyl chloride. The resulting mixture was stirred at room temperature to dissolve the acid chloride. An addition funnel was fitted to this flask, and the HHTPI-pyridine solution in CHCl$_3$ was added into the addition funnel. N$_2$ flow was adjusted through the reactor to a slow and steady rate. HHTPI-Pyridine solution was added continuously drop-wise to the acid chloride solution at room temperature over a period of ~4 hours. Stirring was maintained at a sufficient speed to achieve good mixing of reagents. After completing addition of the HHTPI diol, the addition funnel was replaced with an air condenser, and the 2-necked flask was immersed in an oil bath on a heater fitted with a thermocouple unit. The temperature was raised to 50° C., and the reaction continued at this temperature under N$_2$ for 24 h.

Figure 24A:
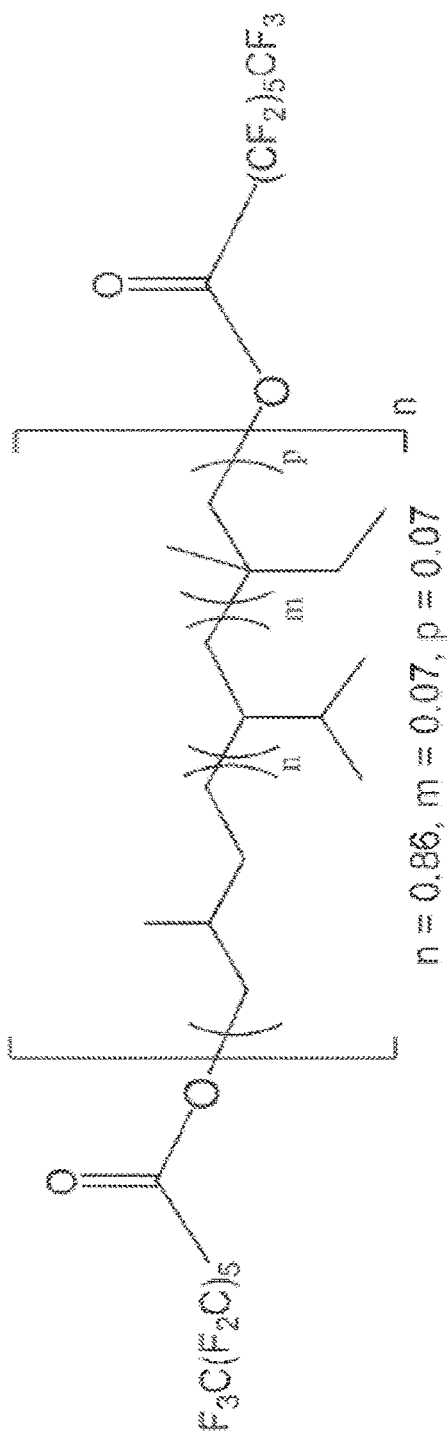
FIG. 24A shows a structure of compound 32.

After the reaction, heating and stirring were turned off. The reaction flask was removed, and its contents were poured into a round bottom flask. CHCl$_3$ was removed by rotary evaporation. Upon concentration, a dense precipitate (pyridine salts) formed. THF was added to dissolve the product, and the precipitated pyridine salts were removed by filtration using a coarse Whatman Filter paper (No 4). Pyridine salts are insoluble in THF. THF was removed by rotary evaporation. The crude product was dissolved in 100 mL of CHCl$_3$ and was poured into a separatory funnel. 150 mL of water were added, followed by the addition of 5 mL of (5N) HCl to neutralize any remaining pyridine. The funnel was shaken, and the product was extracted into CHCl$_3$. The bottom CHCl$_3$ layer containing product was isolated and washed in separatory funnel with water (5 mL of 5% NaHCO$_3$ solution were added to neutralize any remaining HCl). The organic layer was then washed once more with plain distilled water. Isolated CHCl$_3$ layer was concentrated by rotary evaporation to obtain crude product. The crude product was dissolved in 10 mL of isopropanol (IPA) and was added dropwise to a 1 L beaker containing 200 mL of deionized water containing 1% (v/v) MeOH with continuous stirring. Product separated out as an oil. The mixture was kept in ice bath for 20 minutes, and the top water layer was decanted. The oil was dissolved in THF and transferred into 200 mL round bottom flask. THF was removed by rotary evaporation at a maximum temperature of 80° C. and 4 mbar to remove all residual solvents. The resulting product was dried in a vacuum oven at 60° C. for 24 h to give a purified product as a colorless viscous oil (~99.9% yield). The purified product (a mixture of di- and mono-substituted products) was characterized by GPC, elemental analysis, for fluorine, and Hi-Res TGA. Appearance: colorless viscous liquid. Weight Average molecular weight (polystyrene equivalent)=12622 g/mol. Polydispersity, PD: 1.53. Elemental analysis: F: 13.50% (theory: 17.13%). The theoretical chemical structure of compound 32 is shown in FIG. 24A.

Compound 33

Glassware used for the synthesis was dried in an oven at 110° C. overnight. To a 2-necked 1000 mL oven dried round bottom flask equipped with a stir bar was added 100 g (40 mmol) of Hydrogenated-hydroxyl terminated polybutadiene (HLBH diol, MW=2000). The flask with the diol was degassed overnight at 60° C. with gentle stirring and then purged with dry N$_2$ the following day. At this time, the heating was turned off. A 1000 mL graduated cylinder was charged with 415 mL anhydrous CHCl$_3$, sealed by a rubber septa, and purged with dry N$_2$. The CHCl$_3$ was transferred to the 2-necked flask via a cannula, and the diol was stirred vigorously to dissolve in the solvent. Now excess anhydrous pyridine (19.08 g, 241 mmol) was added to the HLBH diol solution using a plastic syringe, and the resulting mixture was stirred to dissolve all materials. Another oven dried 2-necked 1000 mL flask was charged with 38.45 g, (101 mmol) perfluoroheptanoyl chloride, sealed with rubber septa, and degassed for 5 minutes, and then purged with nitrogen. At this time, 277 mL of anhydrous CHCl$_3$ was added using a graduated cylinder and a cannula to transfer the solvent to the 1000 mL 2-necked flask containing the perfluoroheptanoyl chloride. The resulting mixture was stirred at room temperature to dissolve the acid chloride. An addition funnel was fitted to this flask, and the HLBH-pyridine solution in CHCl$_3$ was added into the addition funnel using a cannula. N$_2$ flow was adjusted through the reactor to a slow and steady rate. Continuous drop-wise addition of HLBH-Pyridine solution to the acid chloride solution was started at room temperature over a period of ~4 hours. Stirring was maintained at a sufficient speed to achieve good mixing of reagents. After completing addition of the HLBH, the addition funnel was replaced with an air condenser, and the 2-necked flask was immersed in an oil bath on a heater fitted with a thermocouple unit. The temperature was raised to 50° C., and the reaction continued at this temperature under $N_2$ for 24 h.

Figure 24B:
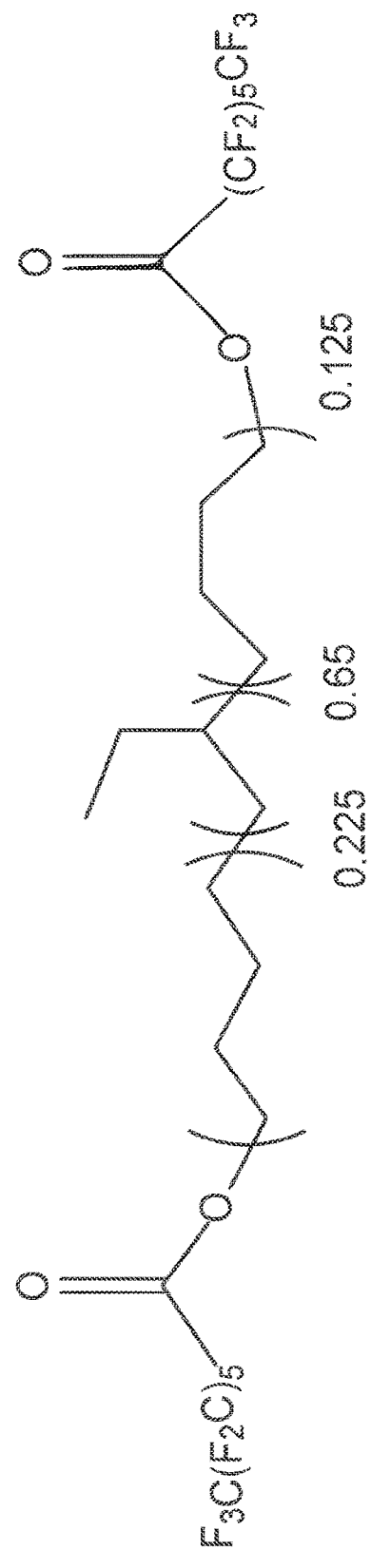
FIG. 24B shows a structure of compound 33.

After the reaction, heating and stirring were turned off. The reaction flask was removed, and its contents were poured into a round bottom flask. $CHCl_3$ was removed by rotary evaporation. Upon concentration, a dense precipitate (pyridine salts) formed. THF was added to dissolve the product, and the precipitated pyridine salts were removed by filtration using a coarse Whatman Filter paper (No 4). Pyridine salts are insoluble in THF. THF was removed by rotary evaporation. The crude product was dissolved in 400 mL of $CHCl_3$ and was poured into a separatory funnel. 500 mL of water were added, followed by the addition of 20 mL of (5N) HCl to neutralize any remaining pyridine. The funnel was shaken, and the product was extracted into $CHCl_3$. The bottom $CHCl_3$ layer containing product was isolated, and washed in a separatory funnel with water (20 mL of 5% $NaHCO_3$ solution were added to neutralize any remaining HCl). The organic layer was then washed once more with plain distilled water. Isolated $CHCl_3$ layer was concentrated by rotary evaporation to obtain crude product. The crude product was dissolved in 20 mL of THF and was then added dropwise to a 4 L beaker containing 1200 mL of deionized water containing 1% (v/v) MeOH with continuous stirring. Product separated out as an oil. The mixture was kept in ice bath for 20 minutes, and the top hexane layer was decanted. The oil was dissolved in THF and transferred into 500 mL round bottom flask. THF was removed by rotary evaporation at a maximum temperature of 80° C. and 4 mbar to remove all residual solvents. The resulting product was dried in a vacuum oven at 60° C. for 24 h to give a purified product as a yellow viscous oil (~80% yield). The purified product (a mixture of di- and mono-substituted products) was characterized by GPC, elemental analysis for fluorine and Hi-Res TGA. Appearance: light yellow viscous liquid. Weight Average molecular weight (polystyrene equivalent)= 6099 g/mol. Polydispersity, PD: 1.08. Elemental analysis: F: 12.84% (theory: 15.54%). The theoretical chemical structure of compound 33 is shown in FIG. 24B.

Compound 34

Glassware used for the synthesis was dried in an oven at 110° C. overnight. To a 2-necked 1000 mL oven dried round bottom flask equipped with a stir bar was added 65 g (63 mmol) of YMer-diol (MW=1000). The flask with the diol was degassed overnight at 60° C. with gentle stirring and then purged with dry $N_2$ the following day. At this time, heating was turned off. A 1000 mL graduated cylinder was charged with 374 mL anhydrous $CHCl_3$, sealed by rubber septa, and purged with dry $N_2$. The $CHCl_3$ was transferred to the 2-necked flask via a cannula, and the diol was stirred vigorously to dissolve in the solvent. Excess anhydrous pyridine (30 g, 375 mmol) was added to the YMer-diol solution using a plastic syringe, the resulting stir to dissolve all materials. Another oven dried 2-necked 1000 mL flask was charged with 59.82 g (156 mmol) of perfluoroheptanoyl chloride, sealed with rubber septa, and degassed for 5 minutes, then purged with nitrogen. At this time 250 mL of anhydrous $CHCl_3$ were added using a graduated cylinder and cannula to transfer the solvent to the 1000 mL 2-necked flask containing the perfluoroheptanoyl chloride. The resulting mixture was stirred at room temperature to dissolve the acid chloride. An addition funnel was fitted to this flask and using a cannula transfer the YMer-diol-pyridine solution in $CHCl_3$ into the addition funnel. $N_2$ flow through the reactor was adjusted to a slow and steady rate. YMer-diol-pyridine solution was added drop-wise, continuously to the acid chloride solution at room temperature over a period of ~4 hours. Stirring was maintained at a sufficient speed to achieve good mixing of reagents. After completing the addition of the YMer-diol-pyridine solution, the addition funnel was replaced with an air condenser, and the 2-necked flask was immersed in an oil bath placed on a heater fitted with a thermocouple unit. The temperature was raised to 40° C., and the reaction continued at this temperature under $N_2$ for 24 h.

Figure 25:
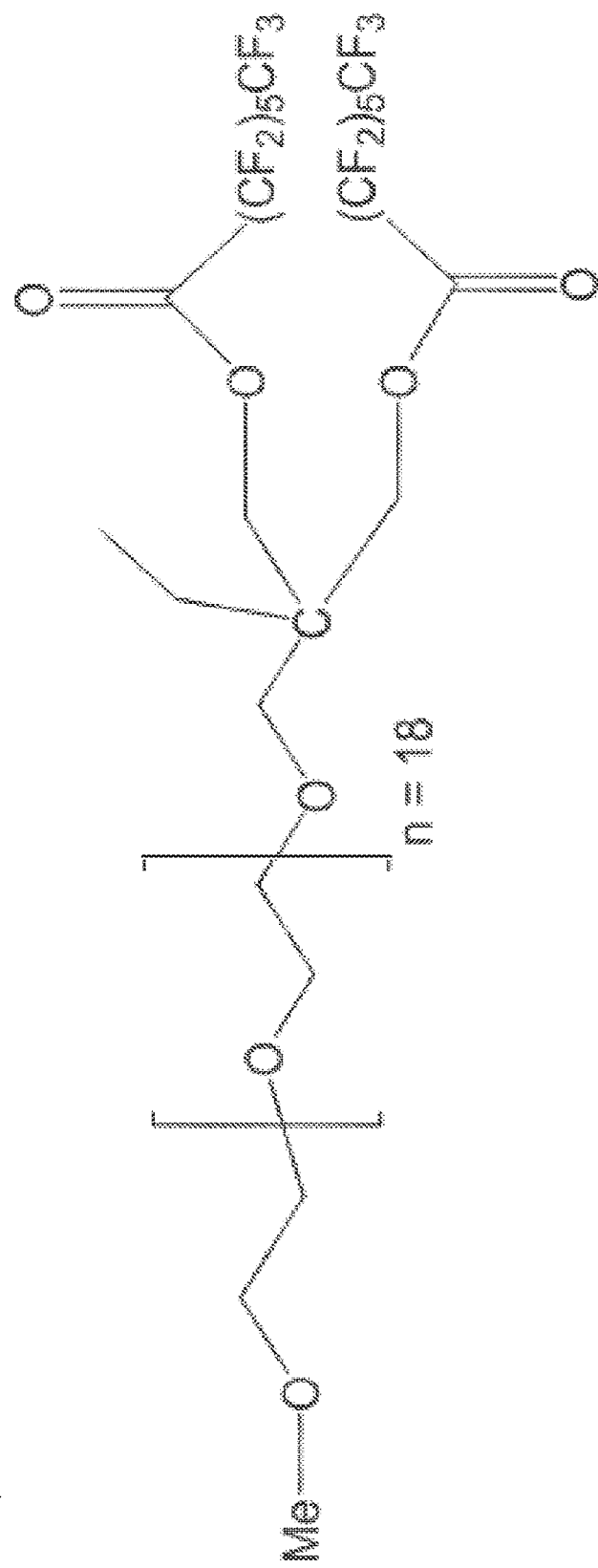
FIG. 25 shows a structure of compound 34.

After the reaction, heating and stirring were turned off. The reaction flask was removed, and the contents were poured into a round bottom flask. $CHCl_3$ was removed by rotary evaporation. Upon concentration, a dense precipitate (pyridine salts) formed. THF was added to dissolve the product. The flask was cooled in an ice bath for 20 minutes, at which time, the precipitated pyridine salts were removed by gravity filtration using a coarse Whatman Filter paper (No 4). Pyridine salts are insoluble in THF. THF was removed by rotary evaporation. The resulting crude product was dissolved in a minimum quantity of Isopropanol (IPA), and this solution was added to 700 mL of hexanes in a beaker with a stir bar. An oil separated out. The top layer was decanted and washed once with 200 mL of hexanes. The residue was then dissolved in 200 mL of THF and transferred to a 500 mL round bottom flask. Rotary evaporation of the solvents at a maximum temperature of 75° C. and 4 mbar vacuum furnished an oil, which was then transferred to a wide mouth jar and further dried for 24 h at 60° C. under vacuum to yield the pure product which solidifies upon cooling at room temperature to an off white waxy semi-solid (Yield 82%). The purified product was characterized by GPC (Molecular Weight based on Polystyrene Standards), elemental analysis for fluorine, $^{19}F$ NMR, $^1H$ NMR, FTIR and TGA. Appearance: waxy semi-solid. Weight Average molecular weight (polystyrene equivalent)=2498 g/mol. Polydispersity: 1.04. Elemental Analysis: F: 27.79% (theory: 28.54%). $^{19}F$ NMR ($CDCl_3$, 400 MHz): δ ppm −81.3 (m, $CF_3$), −118.88 (m, $CF_2$), −122.37 (m, $CF_2$), −123.28 (m, $CF_2$), −126 (m, $CF_2$). $^1H$ NMR ($CDCl_3$, 400 MHz): δ ppm 0.83 (t, $CH_3CH_2$), 1.44 (q, $CH_2CH_3$), 3.34 (m, $CH_2$), 3.51 (m, $CH_2$), 3.54 (m, $CH_2$), 4.30 (m, $CH_2COO-$). FTIR, neat (cm$^{-1}$): 2882 ($CH_2$), 1783 (O—C=O, ester), 1235, 1203, 1143, 1104 ($CF_3$, $CF_2$). The theoretical chemical structure of compound 34 is shown in FIG. 25.

Compound 35

Compound 35 was prepared according to a procedure similar to that used for the preparation of compound 34.

Glassware used for the synthesis was dried in an oven at 110° C. overnight. To a 2-necked 1000 mL oven dried round bottom flask equipped with a stir bar was added 60 g (59 mmol) of YMerOH-triol (MW=1014). The flask with the triol was degassed overnight at 60° C. with gentle stirring and then purged with dry $N_2$ the following day. Heating was turned off. A 1000 mL graduated cylinder was charged with 435 mL anhydrous $CHCl_3$, sealed with rubber septa, and purged with dry $N_2$. The $CHCl_3$ liquid was transferred to the 2-necked flask via a cannula, and the triol was stirred vigorously to dissolve in the solvent. Excess anhydrous pyridine (37 g, 473 mmol) was added to the YMer-triol solution using a plastic syringe, the resulting mixture was stirred to dissolve all materials. Another oven dried 2-necked 1000 mL flask was charged with 84.88 g (222 mmol) of perfluoroheptanoyl chloride, sealed with rubber septa, and degassed for 5 minutes, then purged with nitrogen. 290 mL of anhydrous $CHCl_3$ were added using a graduated cylinder and cannula to transfer the solvent to the 1000 mL 2-necked flask containing the perfluoroheptanoyl chloride. The mixture was stirred at room temperature to dissolve the acid chloride. An addition funnel was fitted to this flask, and the YMerOH-triol-pyridine solution in $CHCl_3$ was transferred to the addition funnel using a cannula. $N_2$ flow through the reactor was adjusted to a slow and steady rate. YMerOH-triol-pyridine solution was added continuously drop-wise to the acid chloride solution at room temperature over a period of ~4 hours. Stirring was maintained at a sufficient speed to achieve good mixing of reagents. After completing the addition of the YMer-triol-pyridine solution, the addition funnel was replaced with an air condenser, and the 2-necked flask was immersed in an oil bath placed on a heater fitted with a thermocouple unit. The temperature was raised to 40° C., and the reaction was continued at this temperature under $N_2$ for 24 h.

Figure 26:
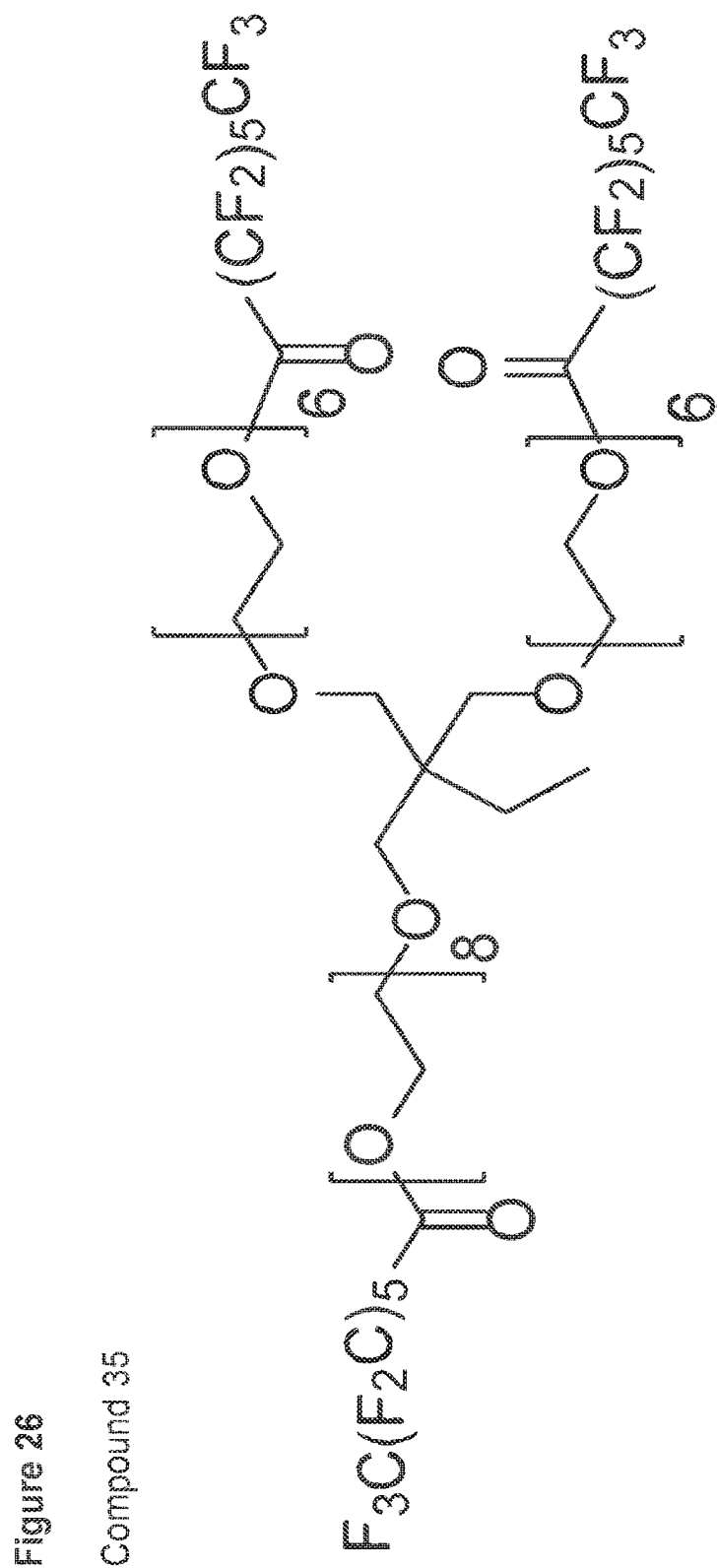
FIG. 26 shows a structure of compound 35.

The resulting product was purified in a similar manner to compound 7 described above. The purification involved rotary evaporation of $CHCl_3$, addition of THF, and separation of the pyridine salts by filtration. The product was then precipitated in isopropanol (IPA)/Hexanes, washed as described above for compound 7, and dried at 75° C. and 4 mbar. Final drying was also done under vacuum at 60° C. for 24 h to yield an oil (Yield 78.2%). The purified product was characterized by GPC (Molecular Weight based on Polystyrene Standards), elemental analysis for fluorine, $^{19}F$ NMR, $^1H$ NMR, FTIR, and TGA. Appearance: light yellow, viscous oil. Weight Average molecular weight (polystyrene equivalent)=2321 g/mol. Polydispersity: 1.06. Elemental Analysis: F: 35.13% (theory: 36.11%). $^{19}F$ NMR ($CDCl_3$, 400 MHz): δ ppm −81.30 (m, $CF_3$), −118.90 (m, $CF_2$), −122.27 (m, $CF_2$), −123.07 (m, $CF_2$), −126.62 (m, $CF_2$). $^1H$ NMR ($CDCl_3$, 400 MHz): δ ppm 0.83 (t, $CH_3CH_2$), 1.44 (q, $CH_2CH_3$), 3.34 (m, $CH_2O$), 3.41 (m, $CH_2$'s), 3.74 (m, $CH_2$), 4.30 (m, $CH_2COO$—). FTIR, neat ($cm^{-1}$): 2870 ($CH_2$), 1780 (O—C=O, ester), 1235, 1202, 1141, 1103 ($CF_3$, $CF_2$). The theoretical chemical structure of compound 35 is shown in FIG. 26.

Compound 36

Compound 36 was prepared according to a procedure similar to that used for the preparation of compound 34.

Glassware used for the synthesis was dried in an oven at 110° C. overnight. To a 2-necked 1000 mL oven dried round bottom flask equipped with a stir bar was added 50 g (65 mmol) of XMer-Tetraol (MW=771). The flask with the tetraol was degassed overnight at 60° C. with gentle stirring and then purged with dry $N_2$ the following day. Heating was turned off. A 1000 mL graduated cylinder was charged with 400 mL anhydrous $CHCl_3$, sealed with rubber septa, and purged with dry $N_2$. $CHCl_3$ was transferred to the 2-necked flask via a cannula, and the tetraol was stirred vigorously to dissolve in the solvent. Excess anhydrous pyridine (51.30 g, 649 mmol) was added to the XMer-Tetraol solution using a plastic syringe, and the resulting mixture was stirred to dissolve all materials. Another oven dried 2-necked 1000 mL flask was charged with 111.63 g (292 mmol) of perfluoroheptanoyl chloride, sealed with rubber septa, and degassed for 5 minutes, and then purged with nitrogen. 300 mL of anhydrous $CHCl_3$ were added using a graduated cylinder and cannula to transfer the solvent to the 1000 mL 2-necked flask containing perfluoroheptanoyl chloride. The resulting mixture was stirred at room temperature to dissolve the acid chloride. An addition funnel was attached to this flask, and the XMer-tetraol-pyridine solution in $CHCl_3$ was transferred into the addition funnel via a cannula. $N_2$ flow through the reactor was adjusted to a slow and steady rate. XMer-tetraol-pyridine solution was added continuously drop-wise to the acid chloride solution at room temperature over a period of ~4 hours. Stirring was maintained at a sufficient speed to achieve good mixing of reagents. After completing addition of the XMer-tetraol-pyridine solution, the addition funnel was replaced with an air condenser, and the 2-necked flask was immersed in an oil bath placed on a heater fitted with a thermocouple unit. The temperature was raised to 40° C., and the reaction continued at this temperature under $N_2$ for 24 h.

Figure 27:
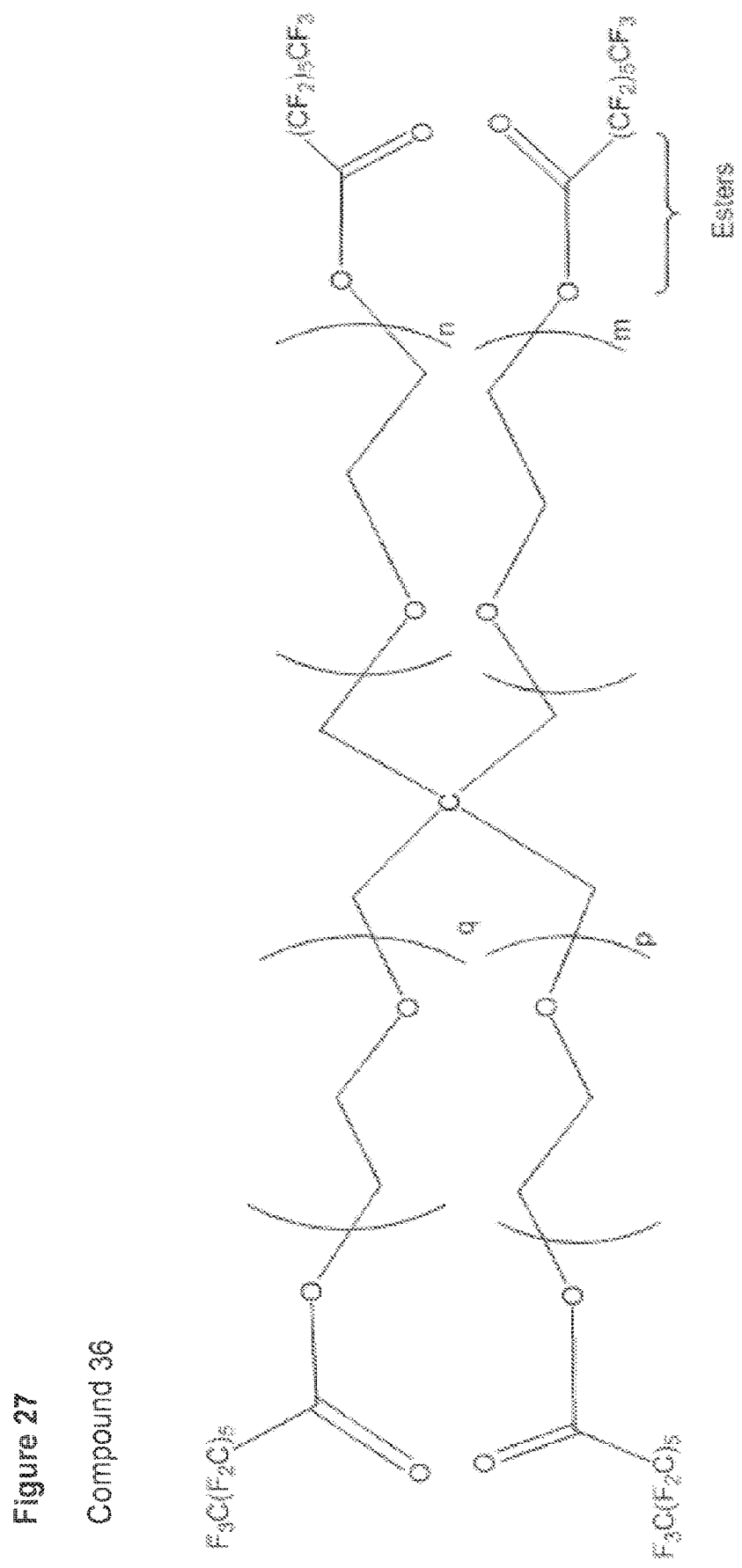
FIG. 27 shows a structure of compound 36.

The resulting product was purified in a similar manner to compound 7 described above, where the $CHCl_3$ was removed by rotary evaporation, addition of THF, and the separation of pyridine salts by filtration after adding THF. The product was then precipitated in isopropanol (IPA)/ hexanes, washed as described for compound 7, and dried at 75° C. and 4 mbar. Final drying was also done under vacuum at 60° C. for 24 h to yield an oil (Yield 80.9%). The purified product was characterized by GPC (Molecular Weight based on Polystyrene Standards), elemental analysis for fluorine, $^{19}F$ NMR, $^1H$ NMR, FTIR, and TGA. Appearance: light yellow, viscous oil. Weight Average molecular weight (polystyrene equivalent)=2410 g/mol. Polydispersity: 1.04. Elemental Analysis: F: 44.07% (theory: 45.85%). $^{19}F$ NMR ($CDCl_3$, 400 MHz): δ ppm −81.37 (m, $CF_3$), −118.89 (m, $CF_2$), −122.27 (m, $CF_2$), −123.06 (m, $CF_2$), −26.64 (m, $CF_2$). $^1H$ NMR ($CDCl_3$, 400 MHz): δ ppm 3.36 (m, $CH_2$'s), 3.75 (m, $CH_2O$), 4.39 (m, $CH_2O$), 4.49 (m, $CH_2COO$—). FTIR, neat ($cm^{-1}$): 2870 ($CH_2$), 1780 (O—C=O, ester), 1235, 1202, 1141, 1103 ($CF_3$, $CF_2$). Thermal decomposition temperature (TGA), $N_2$, at ca. 10% (w/w) loss=327° C. The theoretical chemical structure of compound 36 is shown in FIG. 27.

Compounds 37 and 38

Figure 28A:
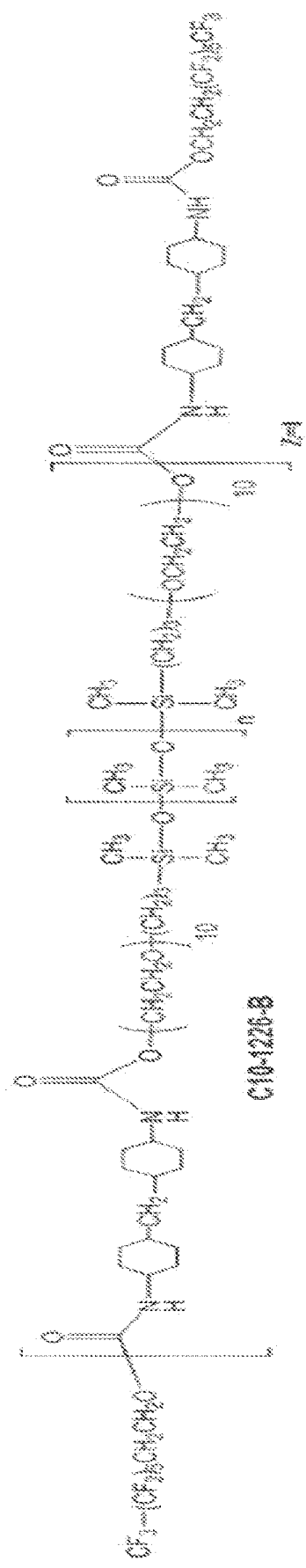
FIG. 28A shows a structure of compound 37.

Glassware used for the synthesis was dried in an oven at 110° C. overnight. 25.04 g (9.7 mmol) of pegylated polydimethylsiloxane diol (C10-Diol) was weighed out in a 250 mL 2-necked flask, heated to 50° C., and degassed overnight with stirring. The diol was then purged with nitrogen and dissolved in 25 mL of anhydrous THF. To the resulting mixture was added 36 mg of bismuth carboxylate catalyst in THF (concentration of 0.02 g/mL) followed by a solution of HMDI diisocyanate in THF (5.34 g, 20.4 mmol) which was previously degassed for 30 minutes followed by nitrogen purge. The addition was performed using a syringe. The reaction vessel was fitted with an air condenser, and the mixture was allowed to react at 60° C. with stirring for 4 h. While the pre-polymer reaction was under way, capstone C6-FOH (fluoroalcohol) (8.82 g, 24.2 mmol) was degassed for 15 minutes in a separate flask and then purged with nitrogen. The fluoroalcohol was dissolved in THF, and a further 24 mg of bismuth carboxylate catalyst in THF was added to it. This mixture was then added to the prepolymer reaction vessel via syringe. After the addition was completed, the reaction mixture was allowed to react overnight at 45° C. under a nitrogen atmosphere. After the reaction, the THF solvent was removed on a rotary evaporator, and the crude residue was dissolved in chloroform. The bismuth catalyst residues were extracted using EDTA solution (pH~9). The solution containing EDTA was washed with DI water in a separatory funnel, and the organic layer was concentrated in a rotary evaporator to give the product as an amber viscous liquid. Final drying was done under vacuum at 60° C. for 24 h to yield a viscous oil (Yield 74%). The purified product was characterized by GPC (Molecular Weight based on Polystyrene Standards), elemental analysis for fluorine, and TGA. Appearance: amber, viscous oil. Weight Average molecular weight (polystyrene equivalent)= 13583 g/mol. Polydispersity: 1.73. Elemental Analysis: F: 12.20% (theory: 12.88%). Thermal decomposition temperature (TGA), $N_2$, at ca. <5% (w/w) loss=231° C. The theoretical chemical structure of compound 37 is shown in FIG. 28A.

Compound 38

Figure 28B:
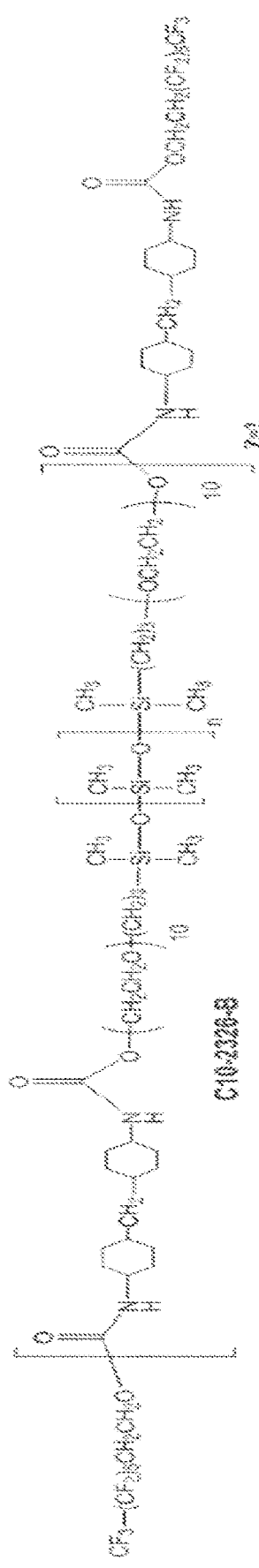
FIG. 28B shows a structure of compound 38.

Compound 38 is synthesized following a procedure similar to that which was used in the preparation of compound 37. Thus, 25.01 g (9.7 mmol) of C10-Diol was reacted with 4.07 g (15.5 mmol) of HMDI in THF in the presence of Bismuth Carboxylate catalyst to form the prepolymer. The prepolymer was then endcapped with 5.29 g (14.5 mmol) Capstone C6-FOH (fluoroalcohol) to yield the product as a viscous oil (Yield, 59%). The purified product was characterized by GPC (Molecular Weight based on Polystyrene Standards), elemental analysis for fluorine, and TGA. Appearance: amber, viscous oil. Weight Average molecular weight (polystyrene equivalent)=19279 g/mol. Polydispersity: 1.79. Elemental Analysis: F: 6.51% (theory: 7.39%). Thermal decomposition temperature (TGA), $N_2$, at ca. <5% (w/w) loss=244° C. The theoretical chemical structure of compound 38 is shown in FIG. 28B.

Compound 39

Compound 39 was synthesized by a 2-step convergent method according to scheme 2. Briefly, the polyisocyanate desmodur 4470 (11.45 g, 11 mmol) was reacted with capstone C6-FOH (7.65 g, 21 mmol) in anhydrous THF in the presence of Bismuth Carboxylate catalyst at 25° C. for 10 minutes. After the dropwise addition of the fluoroalcohol to the polyisocyanate, stirring was continued for 4 hour at 40° C. These steps lead to the formation of a partially fluorinated intermediate that is then coupled with the PLN8K diol (40 g, 5 mmol) at 70° C. over a period of 14 hours to provide compound 39. Because the reactions are moisture sensitive, they are carried out under an inert atmosphere ($N_2$) and anhydrous conditions. The temperature profile is also maintained carefully, especially during the partial fluorination, to avoid unwanted side reactions. Over the course of the reaction, the reaction mixture becomes very viscous, and continuous stirring must be maintained to prevent localized heating.

Figure 29:
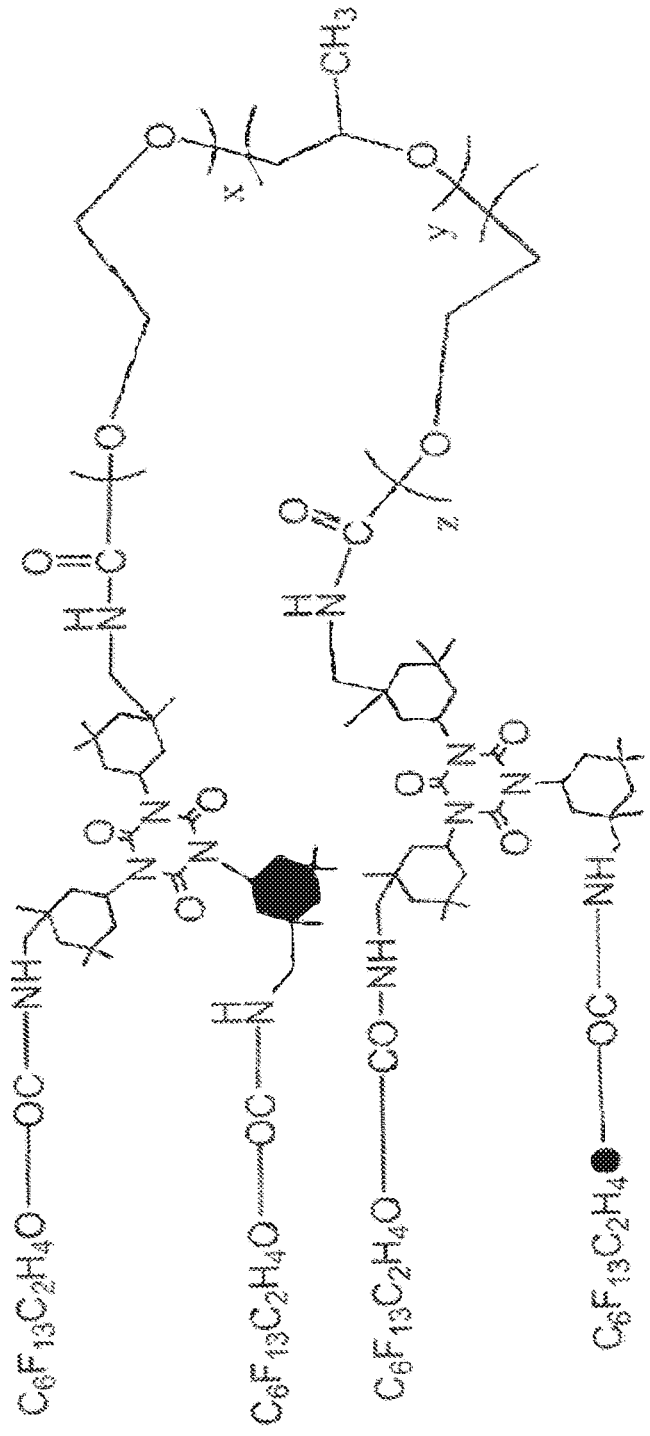
FIG. 29 shows a structure of compound 39.

After the reaction, the THF solvent was evaporated on a rotary evaporator to yield the crude product. The product was purified by dissolving in chloroform and adding the EDTA solution (pH~9.0). The mixture was then transferred to a separatory funnel, and the catalyst residues were separated with the aqueous layer. The organic layer was concentrated, and the product was dissolved in isopropanol and precipitated in hexanes to yield a white chunky solid which was dried under vacuum (yield: 66%). The purified product was characterized by GPC (Molecular Weight based on Polystyrene Standards), elemental analysis for fluorine, and TGA. Appearance: White chunky solid. Weight Average molecular weight (polystyrene equivalent)=31806 g/mol. Polydispersity: 1.32. Elemental Analysis: F: 3.6% (theory: 8.0%). Thermal decomposition temperature (TGA), $N_2$, at ca. <5% (w/w) loss=295° C. The theoretical chemical structure of compound 39 is shown in FIG. 29.

Compound 40

Figure 30:
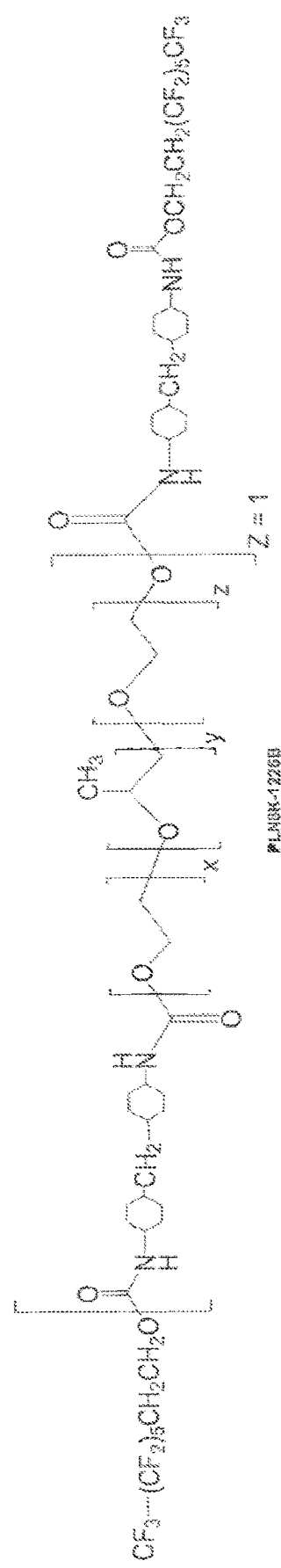
FIG. 30 shows a structure of compound 40.

Compound 40 was synthesized following a procedure similar to that which was used in the preparation of compound 37. Thus, 50.0 g (5.7 mmol) of PLN8K diol were reacted with 4.5 g (17.1 mmol) of HMDI in THF in the presence of bismuth carboxylate catalyst to form the prepolymer. The prepolymer was then endcapped with 7.28 g (20 mmol) capstone C6-FOH (fluoroalcohol) to yield the crude product. The EDTA washes to eliminate the catalyst residues were similar. Final purification was performed by dissolving in isopropanol and precipitating with hexanes to yield a white solid (Yield, 86%). The purified product was characterized by GPC (Molecular Weight based on Polystyrene Standards), elemental analysis for fluorine, and TGA. Appearance: While solid, Weight Average molecular weight (polystyrene equivalent)=9253 g/mol. Polydispersity: 1.28. Elemental Analysis: F: 3.14% (theory: 4.94%). Thermal decomposition temperature (TGA), $N_2$, at ca. <5% (w/w) loss=303° C. The theoretical chemical structure of compound 40 is shown in FIG. 30.

Compound 41

Compound 41 was synthesized following a procedure similar to that which was used in the preparation of compound 27. The theoretical chemical structure of compound 41 is shown in FIG. 21A, with the exception that the middle triblock copolymer is formed from a $C_{10}$-Diol.

The purified product was characterized by GPC (Molecular Weight based on Polystyrene Standards), elemental analysis for fluorine, and TGA. Appearance: colorless viscous liquid, Weight Average molecular weight (polystyrene equivalent)=5858 g/mol. Polydispersity: 1.21. Elemental Analysis: F: 18.39% (theory: 15.08%). Thermal decomposition temperature (TGA), $N_2$, at ca. <10% (w/w) loss=310° C.

Example 2: Evaluation of DEHP Leaching in Modified Resins

The following prophetic examples are illustrative of aspects and embodiments of the present invention.

Compounding

The admixtures and articles of the present invention can be prepared according to the following prophetic example.

PVC plasticized with DEHP may be acquired from numerous manufacturers, and may, for example, have 30 wt. % DEHP. SMMs may be selected to provide good clarity and translucency. For example, plasticized PVC rods may be admixed with SMMs, in varying concentrations and solutions, and the resulting modified resins may undergo x-ray photoelectron spectroscopy (XPS) to evaluate the modified surface. XPS surface analysis may be used to confirm that the SMMs migrated well to the surface of the plasticized PVC. For example, the concentration of fluorine at the surface of the rods may be measured, and in the case of good migration, the surface concentration of fluorine may be from about 5% to about 35%, depending on the selection on SMM and grade of plasticized PVC.

DEHP Leaching Analysis

Modified resins having suitable SMM migration, as determined by XPS surface analysis, are selected for DEHP leaching study.

A variety of solvents may be selected to evaluate leaching. For example, hexane may be selected as the solvent for the preliminary incubations study due to its low polarity index, which makes it a good solvent for DEHP, and due to the fact that the SMMs and PVC are not soluble in hexane. Though hexane extraction may not be a good model to simulate real in-vivo exposure to blood and other bodily fluids, it is a good model to predict the behavior of lipophilic mediums that some plasticized PVC medical devices are usually exposed to, such as intravenous lipid emulsions and total parenteral nutrition solutions.

Two 4.5 cm PVC rod pieces having 30 wt. % DEHP, a control of unmodified plasticized PVC and a modified resin, may be cut and incubated in 7 ml of hexane in 7.5 ml borosilicate glass vials and kept at room temperature under mechanical agitation using a magnetic stir bar. In addition, a blank sample with pure solvent may be prepared.

20 µl aliquots may be withdrawn at different time points; and an equal volume of fresh solvent may be replaced immediately after.

Samples may then be diluted to 1:50 with fresh solvent. A UV-vis spectrophotometer may be blanked before running an analysis, and the absorbance of each solution may then be measured spectrophotometrically, at for example, the maximum absorbance of DEHP.

To determine maximum absorbance, the absorbance spectrum of DEHP in hexane may be analyzed at different concentrations, for example, as shown in FIG. 31. From the absorbance spectrum, it can be seen that the absorbance of DEHP reaches a saturation point at high concentrations of DEHP. From the spectrum, a calibration table and calibration curve can be built, as shown in FIGS. 32A and 32B, respectively.

Figure 7:
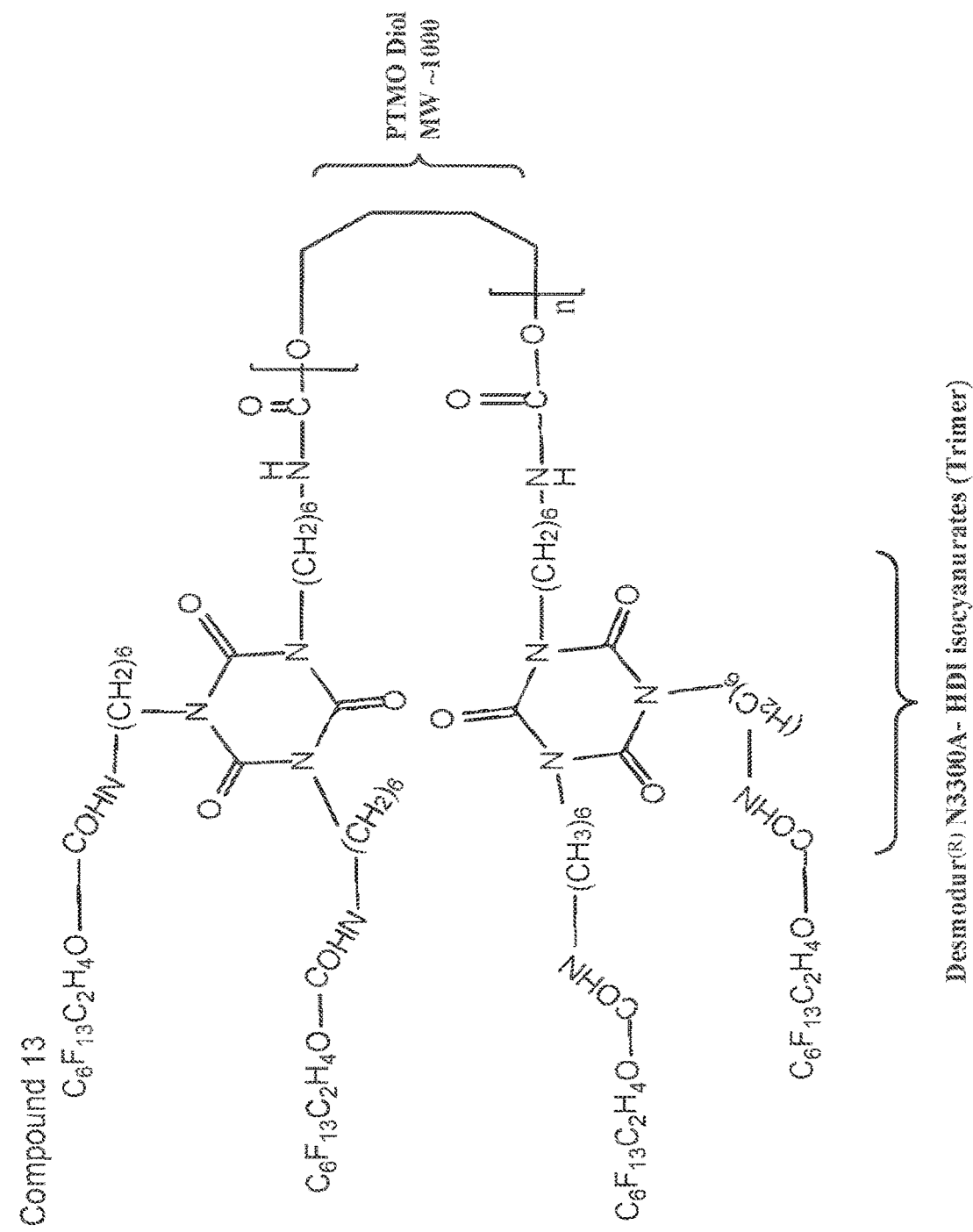
FIG. 7 shows a structure of compound 13.
Figure 8:
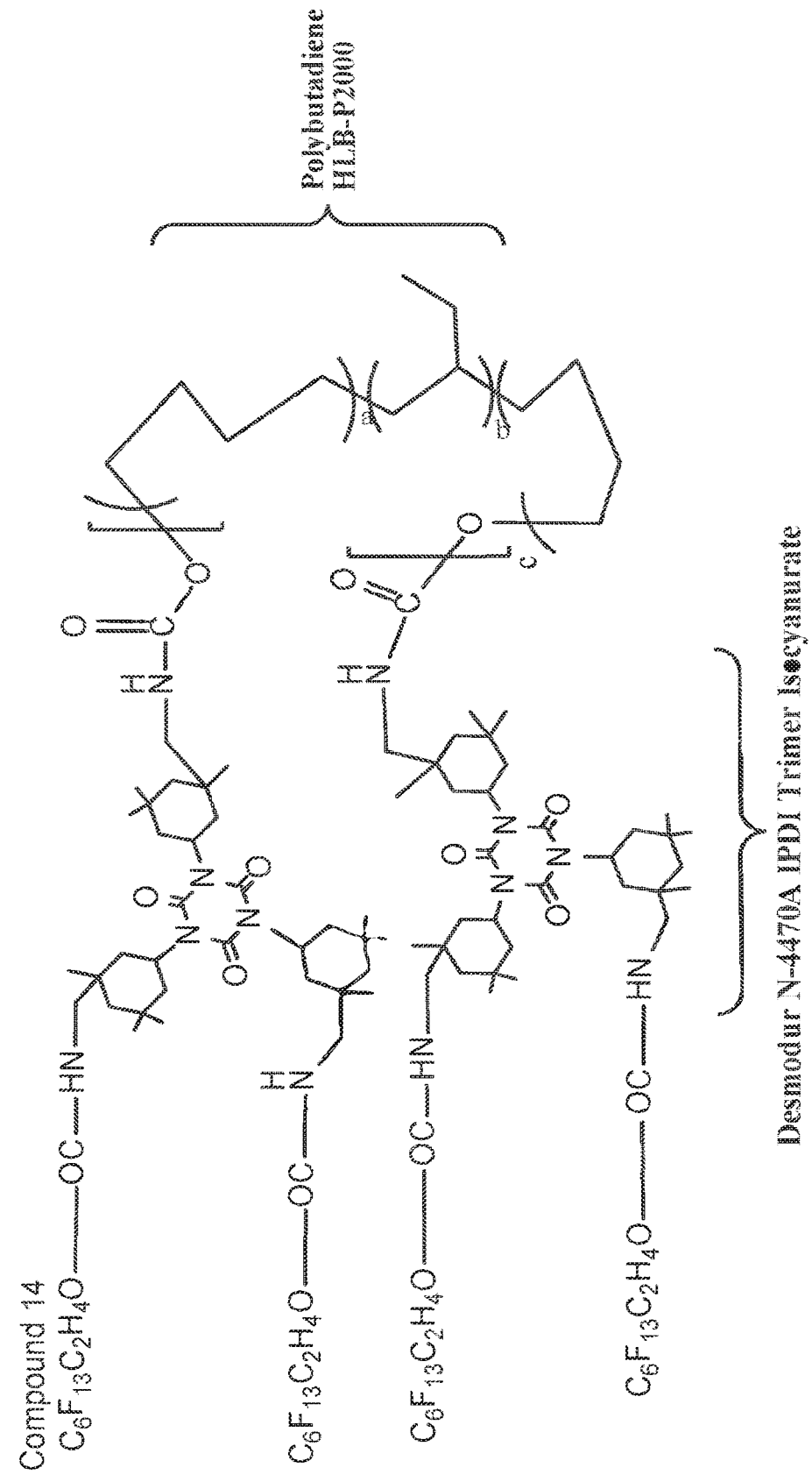
FIG. 8 shows a structure of compound 14.

The amount of DEHP that leached out of the rods may then be calculated from the calibration curve of DEHP in hexane, as shown in FIG. 7. The amount leached can be compared to a control to demonstrate a significant percentage reduction in the amount of DEHP leached in modified resins as compared to the control, and may, for example, show up to a 20% reduction in leaching, and more specifically, a 9%-20% reduction in leaching.

The above analysis can be repeated with other solvent systems and under different conditions to simulate in-vivo conditions. For example, an ethanol solution in water may be used as the extraction medium to simulate extraction of DEHP in blood, and may be chosen in accordance to ISO standards.

Example 3: Evaluation of Optical Properties of Articles of the Invention

The articles compounded in accordance with the procedure described above or by using molding (e.g., injection molding, such as reaction injection molding) or extrusion (e.g., heat extrusion or melt extrusion) instead of extrusion can be used to determine the optical properties, e.g., parallel optical transmittance. The methods for measurement of parallel optical transmittance are known in the art. For example, Japanese Pharmacopeia 15 and Japanese Pharmacopeia 16 describe exemplary procedures for determining parallel optical transmittance. Thus, parallel optical transmittance of an article of uniform thickness of about 0.5 mm (e.g., about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, or about 2.0 mm) can be determined according the methods known in the art for determining parallel optical transmittance of a plastic article (see e.g., general tests described in Japanese Pharmacopeia 15 or Japanese Pharmacopeia 16). An article having a parallel optical transmittance of at least 55% can be deemed as useful for preparation of articles of the invention, such as PVC tubing. Also acceptable is a decrease of less than 50% in the value of parallel optical transmittance of an article containing a surface-modifying macromolecule relative to another article that differs only in that it lacks a surface-modifying macromolecule.

Other Embodiments

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

The invention claimed is:

1. A blended composition comprising from 50% to 99.9% (w/w) of a polyvinyl chloride base polymer, from 0.1% to 80% (w/w) of a plasticizer, and from 0.01% to 20% (w/w) of a surface modifying macromolecule (SMM) described by the formula:

where
(i) A comprises poly(diethylene glycol)adipate, (neopentyl glycol-ortho phthalic anhydride) polyester, (diethylene glycol-ortho phthalic anhydride) polyester, (1,6-hexanediol-ortho phthalic anhydride) polyester, polypropylene oxide, polyethylene oxide, or polytetramethylene oxide;
(ii) B comprises a urethane;
(iii) $F_T$ is a polyfluoroorgano group, and
(iv) n is an integer from 1 to 10; and
wherein the plasticizer is selected from trimellitates, adipates, dioctyl terephthalate and orthophthalates selected from n-octyl n-decyl phthalate, di(2-propyl heptyl) phthalate, diundecyl phthalate, diisononyl phthalate, diisodecyl phthalate, diisoundecyl phthalate, di-n-propyl phthalate, din-butyl phthalate, butyl cyclohexyl phthalate, di-n-pentyl phthalate, di-n-hexyl phthalate, butyl decyl phthalate, diisohexyl phthalate, diisoheptyl phthalate, diisooctyl phthalate, diisotridecyl phthalate, ditridecyl phthalate, dimethyl phthalate, diethyl phthalate, diisobutyl phthalate, dicyclohexyl phthalate, di-isotridecyl phthalate, di-C16-18 alkyl phthalate, benzyl 3-isobutyryloxy-1-isopropyl-2,2-dimethylpropyl phthalate, benzyl C7-9-branched and linear alkyl phthalate, and di-(2-ethylhexyl) phthalate.

2. The composition of claim 1, wherein the plasticizer is 10% to 50% (w/w).

3. The composition of claim 2, wherein the plasticizer is 20% to 45% (w/w).

4. The composition of claim 1, wherein the amounts of said polyvinyl chloride base polymer, said plasticizer, and SMM provide a miscible admixture.

5. The composition of claim 1, wherein said trimellitate is tri-(2-ethylhexyl)trimellitate (TOTM).

6. The composition of claim 4, wherein said plasticizer is dioctyl terepthalate (DEHT).

7. The composition of claim 1, wherein said composition comprises from 60% to 80% (w/w) of said polyvinyl chloride base polymer, from 20% to 40% (w/w) of said plasticizer, and from 0.5% to 5% (w/w) of said SMM.

8. The composition of claim 1, further comprising one or more additives selected from the group consisting of a heat stabilizer, an impact modifier, a process aid, a lubricant, a filler, a flame retardant, a pigment, a blowing agent, a biocide, a viscosity modifier, an antistatic agent, an antioxidant, a UV absorber, an antifogging agent, and a bonding agent.

9. An article comprising the composition of claim 1.

10. The article of claim 9, wherein said article is transparent.

11. The article of claim 10, wherein said article is an implantable device.

12. The article of claim 11, wherein said implantable device contacts body fluids.

13. The article of claim 11, wherein said implantable device is in contact with fluids that enter the body.

14. The article of claim 10, wherein said article is PVC tubing or a PVC bag.

15. The article of claim 9, wherein said article exhibits reduced leaching of said plasticizing agent.

16. The article of claim 15, wherein said article has a hardness value on the shore A scale or the shore D scale.

17. The article of claim 16, wherein said article has a hardness value of between 60A and 85D.

18. A method for making an article comprising the steps of:
  (a) preparing said blended composition of claim 1; and
  (b) processing said composition to form or to coat said article.

19. The method of claim 18, wherein said processing comprises one or more of extruding, injection molding, calendaring, mixing, spraying, dipping, or casting said composition.

20. The method of claim 18, wherein said article is transparent.

21. The method of claim 18, wherein said article exhibits reduced leaching of said plasticizing agent.

* * * * *